United States Patent
Nozulak et al.

(10) Patent No.: US 9,067,881 B2
(45) Date of Patent: Jun. 30, 2015

(54) 4-TOLYL-ETHYNYL-OCTAHYDRO-INDOLE-1-ESTER DERIVATIVES

(75) Inventors: Joachim Nozulak, Heitersheim (DE); Dieter Oser, Laufen (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 13/979,987

(22) PCT Filed: Jan. 20, 2012

(86) PCT No.: PCT/EP2012/050889
§ 371 (c)(1),
(2), (4) Date: Jul. 16, 2013

(87) PCT Pub. No.: WO2012/101058
PCT Pub. Date: Aug. 2, 2012

(65) Prior Publication Data
US 2013/0303538 A1    Nov. 14, 2013

Related U.S. Application Data

(60) Provisional application No. 61/435,601, filed on Jan. 24, 2011.

(51) Int. Cl.
| C07D 209/08 | (2006.01) |
| A61K 31/404 | (2006.01) |
| A61K 31/4178 | (2006.01) |
| A61K 31/4439 | (2006.01) |
| A61K 31/5377 | (2006.01) |
| A61K 45/06 | (2006.01) |
| C07D 401/12 | (2006.01) |
| C07D 403/12 | (2006.01) |

(52) U.S. Cl.
CPC ............ *C07D 209/08* (2013.01); *A61K 31/404* (2013.01); *A61K 31/4178* (2013.01); *A61K 31/4439* (2013.01); *A61K 31/5377* (2013.01); *A61K 45/06* (2013.01); *C07D 401/12* (2013.01); *C07D 403/12* (2013.01)

(58) Field of Classification Search
CPC ........................ C07D 209/14; C07D 209/34
USPC ......................................................... 548/452
See application file for complete search history.

(56) References Cited

FOREIGN PATENT DOCUMENTS

| WO | 03/047581 | 6/2003 |
| WO | 2010/018154 | 2/2010 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:llwww.cnn.com120031HEALTHIconditions/091241alzheimers.drug.aplindexhtml>.*
Stella et al., Prodrugs Challenges and Rewards Part 1, pp. 225-281 (2007).
Stella et al., Advanced Drug Delivery Reviews, pp. 677-694 (2007).

* cited by examiner

Primary Examiner — Shawquia Jackson
(74) Attorney, Agent, or Firm — Laura Madden

(57) ABSTRACT

The invention relates to compounds of the formula (I) in which the substituents are as defined in the specification; in free form or in salt form; to their preparation, to their use as medicament and to medicaments comprising them.

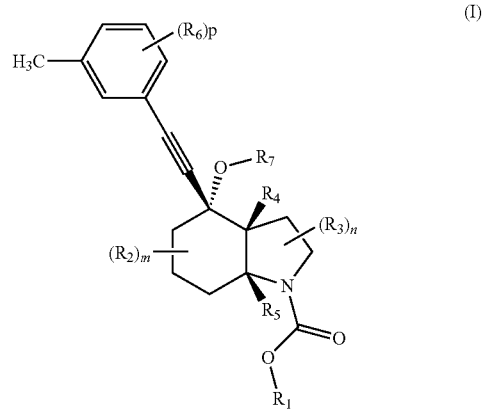

6 Claims, No Drawings

4-TOLYL-ETHYNYL-OCTAHYDRO-INDOLE-1-ESTER DERIVATIVES

This application is a U.S. National Phase filing of International Application No. PCT/EP2012/050889 filed 20 Jan. 2012, which claims priority to U.S. Application No. 61/435,601 filed 24 Jan. 2011, the contents of which are incorporated herein by reference in their entirety.

The invention relates to 4-tolyl-ethynyl-octahydro-indole-1-ester derivatives, to their preparation, to their use as medicaments and to medicaments comprising them.

Some mGluR5 antagonists are described e.g. in WO2003047581 and WO2010018154.

mGluR5 antagonists are considered to be useful in the treatment of a wide range of disorders, in particular fragile X syndrome (FXS), L-dopa induced dyskinesias in Parkinsons Disease (PD-LID) and Gastro-Esophageal Reflux Disease (GERD).

There is a need to provide drugs or prodrugs that act in-vivo as mGluR5 antagonists and are good drug candidates.

In a first aspect, the invention provides prodrugs of mGluR5 antagonists which are potentially useful in the treatment of a wide range of disorders, particularly FXS, PD-LID and/or GERD.

In said first aspect, the invention relates to a 4-tolyl-ethynyl-octahydro-indole-1-ester derivative being a compound of the formula I

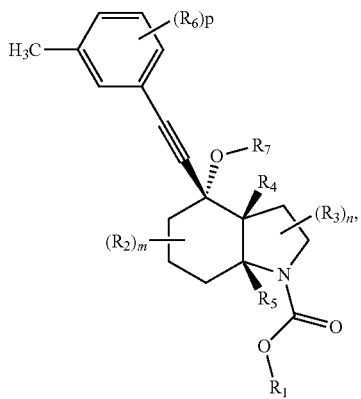

(I)

wherein
$R_1$ is $C_{1-4}$alkyl, $C_{3-6}$cycloalkyl or $C_{3-8}$cycloalkyl-$C_{1-4}$alkyl;
$R_2$ and $R_3$ independently are halogen, cyano, hydroxy, amino, $C_{1-4}$ alkyl; $C_{1-4}$halogenalkyl; $C_{1-4}$hydroxyalkyl; $C_{1-4}$aminoalkyl $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;
m is 0, 1, 2, 3, 4, 5 or 6;
n is 0, 1, 2, 3 or 4;
$R_4$ and $R_5$ independently are hydrogen, halogen or methyl;
$R_6$ is halogen, hydroxy, amino, cyano, methyl or methoxy;
p is 0, 1, 2, 3 or 4;
$R_7$ is —C(O)$R_8$; —$R_9$; —P(O$R_{10}$)(O$R_{11}$), —Z, —C(O)—(CH$_2$)$_q$—O—Z, —(CH$_2$)$_r$—O—Z or —(CH$_2$)$_s$—O—(CH$_2$)$_t$—O—Z;

$R_8$ is $C_{1-20}$alkyl which may be substituted once or more than once by $R_{12}$; $C_{2-20}$alkenyl which may be substituted once or more than once by $R_{13}$; $C_{2-20}$alkinyl which may be substituted once or more than once by $R_{14}$; or a three- to seven-membered monocyclic ring system which may be aromatic, saturated or unsaturated non-aromatic, which may contain from 1 to 4 hetero atoms selected from nitrogen, oxygen and sulfur, and which may be substituted once or more than once by $R_{15}$;
$R_9$ is $C_{1-10}$alkyl which may be substituted once or more than once by $R_{16}$; $C_{2-10}$alkenyl which may be substituted once or more than once by $R_{17}$; $C_{2-10}$alkinyl which may be substituted once or more than once by $R_{18}$; or a three- to seven-membered monocyclic ring system which may be aromatic, saturated or unsaturated non-aromatic, which may contain from 1 to 4 hetero atoms selected from nitrogen, oxygen and sulfur, and which may be substituted once or more than once by $R_{19}$;
$R_{10}$ and $R_{11}$ independently are $C_{1-6}$alkyl;
each $R_{12}$, $R_{13}$, $R_{14}$, $R_{16}$, $R_{17}$ and $R_{18}$ independently is halogen, cyano, hydroxy, —SH, amino, $C_{1-6}$alkoxy, $C_{1-4}$alkoxy-$C_{1-4}$alkoxy, $C_{1-4}$alkoxy-$C_{1-4}$alkoxy-$C_{1-4}$alkoxy, $C_{1-6}$alkylthio, —C(O)OH, $C_{1-6}$alkylamino, di($C_{1-6}$alkyl)amino, aminocarbonyl, $C_{1-6}$alkylaminocarbonyl, di($C_{1-6}$alkyl)aminocarbonyl, $C_{1-6}$alkylcarbonylamino, ($C_{1-6}$alkyl)($C_{1-5}$alkylcarbonyl)amino, —N(H)—C(NH)(NH$_2$), $C_{1-6}$alkylcarbonyloxy, $C_{1-6}$alkoxycarbonyl, or a three- to seven-membered monocyclic ring system which may be aromatic, saturated or unsaturated non-aromatic, which may contain from 1 to 4 hetero atoms selected from nitrogen, oxygen and sulfur, which may be attached directly or via bivalent oxygen or carbonyl, and which may in turn be substituted once or more than once by halogen, cyano, hydroxy, $C_{1-4}$alkyl, $C_{1-4}$alkoxy or $C_{1-4}$halogenalkyl;
each $R_{15}$ and $R_{19}$ independently is halogen, cyano, hydroxy, —SH, amino, $C_{1-6}$alkoxy, $C_{1-4}$alkoxy-$C_{1-4}$alkoxy, $C_{1-4}$alkoxy-$C_{1-4}$alkoxy-$C_{1-4}$alkoxy, $C_{1-6}$alkylthio, —C(O)OH, $C_{1-6}$alkylamino, di($C_{1-6}$alkyl)amino, $C_{1-6}$alkylaminocarbonyl, di($C_{1-6}$alkyl)aminocarbonyl, $C_{1-6}$alkylcarbonylamino, ($C_{1-6}$alkyl)($C_{1-6}$alkylcarbonyl)amino, $C_{1-6}$alkylcarbonyloxy, $C_{1-6}$alkoxycarbonyl; $C_{1-6}$alkyl, $C_{1-6}$halogenalkyl, $C_{1-6}$cyanoalkyl, $C_{1-6}$hydroxyalkyl, $C_{1-4}$alkoxy-$C_{1-4}$alkyl;
q is an integer from 1 to 10;
r is an integer from 1 to 10;
s is an integer from 1 to 6;
t is an integer from 1 to 6;
Z is a saccharide moiety selected from the group consisting of a monosaccharide moiety and an oligosaccharide moiety, wherein Z is attached through a hydroxyl oxygen atom of Z; in free form or in salt form.

The terms "compounds of the invention" or "prodrugs of the invention" comprise compounds of formula (I).

In particular, preferred prodrugs of the invention should be well absorbed from the gastrointestinal tract, be transformed into the parent compound (or active principle, being the compound that in-vivo acts as mGluR5 antagonist), the parent compound should be sufficiently metabolically stable and possess favorable pharmacokinetic properties.

Further preferred prodrugs of the invention lead to an oral bioavailability of the parent compound which is comparable to the use of the parent compound as administered drug Further preferred prodrugs of the invention increase the oral bioavailability of the parent compound compared to the use of the parent compound as administered drug. Said increased oral bioavailability may manifest itself in different ways: (i) a biological effect may be achieved after oral administration when the parent compound is ineffective upon oral administration, (ii) an earlier onset of action upon oral administration, (iii) a lower dose needed to achieve the same effect, (iv) a higher effect achieved by the same dose or (v) a prolonged action at the same dose.

Further preferred prodrugs of the invention are transformed into parent compounds which in-vivo bind potently to mGluR5 whilst showing little affinity for other receptors.

Further preferred prodrugs of the invention—when the active principle is targeted against receptors in the central nervous system—are transformed into parent compounds that cross the blood brain barrier freely.

Further preferred prodrugs of the invention—when the active principle is targeted selectively against receptors in the peripheral nervous system—are transformed into parent compounds that do not cross the blood brain barrier.

Prodrugs, parent compounds and released pro-moieties should be non-toxic and demonstrate few side-effects.

Furthermore, the ideal prodrug of the invention will be able to exist in a physical form that is stable, non-hygroscopic and easily formulated.

Especially suitable prodrugs for pediatric uses (e.g. with infant FXS patients) have a good solubility in water; this facilitates manufacture of products being liquid drinking formulations and/or solid formulations for making liquid drinking products.

Unless indicated otherwise, the expressions used in this invention have the following meaning:

"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl represents e.g. a straight-chain or branched-chain $C_{1-4}$alkyl, e.g. methyl, ethyl, n-propyl, iso-propyl and tert-butyl.

Each alkyl part of "alkoxy", "halogenalkyl" and so on shall have the same meaning as described in the above-mentioned definition of "alkyl", especially regarding linearity and size.

"Alkenyl" represents a straight-chain or branched-chain alkenyl group which contains one or more, e.g. 2 to 4, double bonds between adjacent carbon atoms, for example, ethenyl.

"Alkinyl" represents a straight-chain or branched-chain alkinyl group which contains one or more, e.g. 2 to 4, triple bonds between adjacent carbon atoms, for example, ethinyl.

"$C_{3-6}$cycloalkyl" represents a saturated alicyclic moiety having from three to six carbon atoms. This term refers to groups such as cyclopropyl, cyclobutyl, cyclopentyl and cyclohexyl.

A substituent being substituted "once or more than once", for example as defined for $R_8$, is preferably substituted by one to three substituents.

Halogen is generally fluorine, chlorine, bromine or iodine e.g. fluorine, chlorine or bromine. Halogenalkyl groups are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl.

In the context of the invention, the definition of e.g. $R_8$ as a "three- to seven-membered monocyclic ring system which may be aromatic, saturated or unsaturated non-aromatic and which may contain from 1 to 4 hetero atoms selected from nitrogen, oxygen and sulfur" encompasses a $C_6$-aromatic hydrocarbon group; a five- to six-membered heterocyclic aromatic ring system; a three- to seven-membered monocyclic non-aromatic hydrocarbon group and a non-aromatic heterocyclic ring system of the same size.

Preferably, but also depending on substituent definition, "five- to six-membered heterocyclic aromatic ring systems" consist of 5 to 6 ring atoms of which 1-3 ring atoms are hetero atoms.

Examples of heterocyclic ring systems are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine or morpholine. Further examples of heterocycles are: oxazole, isoxazole, thiazole, isothiazole triazole, pyrrole, furane, tetrahydrofurane, pyridine, pyrimidine, imidazole or pyrazole.

"Oligosaccharide moiety" represents a saccharide moiety wherein from 2 to 10 monosaccharide moieties are linked together. The constituent monosaccharide moieties may be different from each other, e.g. a hexose monosaccharide or a pseudosugar.

"Monosaccharide moiety" represents monosaccharides and derivatives thereof, wherein (i) the ring oxygen atom of the monosaccharide is replaced by carbon ("pseudosugars" or "carba-sugars"), nitrogen or sulfur, (e.g. nojirimycin), (ii) a hydroxyl substituent of the monosaccharide is replaced by an amino group ("amino sugars"), (e.g. D-galactopyranosylamine), (iii) the monosaccharide has a double bond between two adjacent ring carbon atoms, (e.g. D-galactal), (iv) a hydroxyl substituent of the monosaccharide is replaced with hydrogen, $C_{1-6}$alkoxy, $C_{1-6}$alkylcarbonyloxy, or halogen, (e.g. 2-O-methyl-D-fructose), (v) the derivative is a sulfate derivative (e.g. D-mannose-6-sulfate) and/or (vi) the derivative is a phosphate derivative (e.g. D-glucose-6-phosphate).

The term "monosaccharide" includes monosaccharides differing from each other in a multitude of ways. For examples, they can exist in the open chain, pyranose or furanose form to differing degrees. Certain monosaccharides, such as glucose or ribose, exist predominantly in the cyclic form. In solution fructose, for example, can exist mostly in a 6-membered pyranose form and/or its 5-membered furanose form, each of these forms can exist in alpha- or beta-configuration. Therefore, fructose can exist in its alpha-fructopyranose, beta-fructopyranose, alpha-fructofuranose, beta-fructofuranose or open chain forms. For making prodrugs of the invention, fructose can be attached to in any of these configurations. In its 6-membered pyranose form, fructose is more likely to form a bond, for example, through the single primary alcohol that is present at the 1 position in the pyranose form. In its 5-membered furanose form, fructose has two primary alcohols which are at the 1 and 6 position. In the furanose form, bonds are likely through either of these primary alcohols at the 1 or the 6 position. Suitable monosaccharides include, but are not limited to, any of several simple open or closed chain sugars (in the L or D configuration), typically having 5 or 6 carbon atoms (a pentose monosaccharide or a hexose monosaccharide), as well as 7 carbons (heptose monosaccharide). Examples of monosaccharides are D-glucose, L-glucose, D-fructose, L-fructose, D-ribose or L-ribose.

Depending on further substituent definitions, the compounds of formula I may exist in optically active form or in form of mixtures of optical isomers, e.g. in form of diastereomeric mixtures. In particular, further asymmetrical carbon atom(s) may be present in the compounds of formula I and their salts. Unless otherwise provided herein, all such optical isomers and their mixtures are embraced by the invention. In this context it is noted that for all compounds of formula I, the asymmetrical carbon atoms in the 3a-, 4- and 7a-position of the octahydro-indole-moiety have the fixed configuration as shown in the image for compounds of formula I. For example, compounds of formula I, wherein $R_4$ and $R_5$ are both hydrogen, have a (3aR,4S,7aR)-configuration.

As used herein, the term "isomers" refers to different compounds that have the same molecular formula but differ in arrangement and configuration of the atoms.

Also as used herein, the term "an optical isomer" or "a stereoisomer" refers to any of the various stereo isomeric configurations which may exist for a given compound of the invention.

It is understood that a substituent may be attached at a chiral center of a carbon atom. The term "chiral" refers to molecules which have the property of non-superimposability on their mirror image partner, while the term "achiral" refers to molecules which are superimposable on their mirror image partner.

"Enantiomers" are a pair of stereoisomers that are non-superimposable mirror images of each other.

A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system.

When a compound ispure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line.

The compounds described herein may contain—besides the three centers depicted for compounds of formula I—one or more further asymmetric centers and may thus give rise to diastereomers, and other stereoisomeric forms that may be defined, in terms of absolute stereochemistry, as (R)- or (S)-. Unless otherwise provided herein, the invention is meant to include all such possible isomers, including mixtures and optically pure forms.

Optically active (R)- and (S)-isomers may be prepared using chiral synthons or chiral reagents, or resolved using conventional techniques.

If the compound contains a double bond, substituent(s) may have an E or Z configuration.

Unless provided otherwise herein, any asymmetric atom (e.g. carbon or the like) of the compound(s) of the invention may be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Substituents at atoms with unsaturated bonds may, if possible, be present in cis-(Z)- or trans-(E)-form.

Accordingly, as used herein and unless provided otherwise herein, a compound of the invention can be in the form of one of the possible isomers, rotamers, atropisomers, tautomers or mixtures thereof, for example, as substantially pure geometric (cis or trans) isomers, diastereomers, optical isomers (antipodes) or mixtures thereof.

Unless provided otherwise herein, any resulting mixtures of isomers can be separated on the basis of the physicochemical differences of the constituents, into the pure or substantially pure geometric or optical isomers, diastereomers, for example, by chromatography and/or fractional crystallization.

Unless provided otherwise herein, any resulting mixtures of isomers of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Mixtures of isomers can also be resolved by chiral chromatography, e.g., high pressure liquid chromatography (HPLC) using a chiral adsorbent.

Depending on substituent definition, compounds of formula I may occur in various tautomeric forms. All tautomeric forms of the compounds of formula I are embraced by the invention.

Compounds of the invention may exist in free form or as a salt. In this specification, unless otherwise indicated, language such as "compound of formula I" is to be understood as embracing the compounds in any form, for example free or acid addition salt form. Salts which are unsuitable for pharmaceutical uses but which can be employed, for example, for the isolation or purification of free compounds of the invention, such as picrates or perchlorates, are also included. For therapeutic use, only pharmaceutically acceptable salts or free compounds are employed (where applicable in the form of pharmaceutical preparations), and are therefore preferred. Salts are preferably physiologically acceptable salts, formed by the addition of an acid.

As used herein, the term "pharmaceutically acceptable salts" refers to salts that retain the biological effectiveness and properties of the compounds of this invention and, which typically are not biologically or otherwise undesirable. The compounds of the invention may be capable of forming acid salts by virtue of the presence of suitable groups, such as amino groups.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, glucaptate, gluconate, glucuronate, hippurate, hydroiodideliodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the invention can be synthesized from a parent compound by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The invention includes all pharmaceutically acceptable isotopically-labeled compounds of the invention, e.g. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio. Examples of isotopes suitable for inclusion in the compounds of the invention comprises isotopes of hydrogen, such as $^2$H. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of the invention with the co-crystal former under crystallization conditions and isolating co-crystals thereby formed. Suitable co-crystal formers include those described in WO 2004/078163. Hence the invention further provides co-crystals comprising a compound of formula (I).

Compounds of the invention are either obtained in the free form or as a salt thereof.

Furthermore, the compounds of the invention, including their salts, can also be obtained in the form of their hydrates, or include other solvents used for their crystallization.

Preferred substituents, preferred ranges of numerical values or preferred ranges of the radicals present in compounds of the formula I and the corresponding intermediate compounds are defined below. The definition of the substituents applies to the end-products as well as to the corresponding intermediates. The definitions of the substituents may be combined at will, e.g. preferred substituents $R_1$ and particularly preferred substituents $R_2$.

In especially preferred embodiments, the invention relates to one or more than one of the compounds of the formula I mentioned in the Examples hereinafter, in free form or in salt form.

In one embodiment, the invention provides a compound of formula I, wherein $R_1$ is $C_{1-4}$alkyl, $C_{3-6}$cycloalkyl or $C_{3-8}$cycloalkyl-$C_{1-4}$alkyl;

$R_2$ and $R_3$ independently are halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_4$alkyl; di-($C_{1-4}$alkyl)amino-$C_{1-4}$alkyl; $C_{1-4}$alkoxy-$C_{1-4}$alkyl; $C_{2-4}$alkenyl; $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;

m is 0, 1, 2, 3, 4, 5 or 6;

n is 0, 1, 2, 3 or 4;

$R_4$ and $R_5$ independently are hydrogen, halogen or methyl;

$R_6$ is halogen, hydroxy, amino, cyano, methyl or methoxy;

p is 0, 1, 2, 3 or 4;

$R_7$ is —C(O)$R_8$; —$R_9$; —P(O$R_{10}$)(O$R_{11}$), —Z, —C(O)—(CH$_2$)$_q$—O—Z, —(CH$_2$)$_r$—O—Z or —(CH$_2$)$_s$—O—(CH$_2$)$_t$—O—Z;

$R_8$ is $C_{1-20}$alkyl which may be substituted once or more than once by $R_{12}$; $C_{2-20}$alkenyl which may be substituted once or more than once by $R_{13}$; $C_{2-20}$alkinyl which may be substituted once or more than once by $R_{14}$; or a three- to seven-membered monocyclic ring system which may be aromatic, saturated or unsaturated non-aromatic, which may contain from 1 to 4 hetero atoms selected from nitrogen, oxygen and sulfur, and which may be substituted once or more than once by $R_{15}$;

$R_9$ is $C_{1-10}$alkyl which may be substituted once or more than once by $R_{16}$; $C_{2-10}$alkenyl which may be substituted once or more than once by $R_{17}$; $C_{2-10}$alkinyl which may be substituted once or more than once by $R_{18}$; or a three- to seven-membered monocyclic ring system which may be aromatic, saturated or unsaturated non-aromatic, which may contain from 1 to 4 hetero atoms selected from nitrogen, oxygen and sulfur, and which may be substituted once or more than once by $R_{19}$;

$R_{10}$ and $R_{11}$ independently are $C_{1-6}$alkyl;

each $R_{12}$, $R_{13}$, $R_{14}$, $R_{16}$, $R_{17}$ and $R_{18}$ independently is halogen, cyano, hydroxy, —SH, amino, $C_{1-6}$alkoxy, $C_{1-4}$alkoxy-$C_{1-4}$alkoxy, $C_{1-4}$alkoxy-$C_{1-4}$alkoxy-$C_{1-4}$alkoxy, $C_{1-6}$alkylthio, —C(O)OH, $C_{1-6}$alkylamino, di($C_{1-6}$alkyl)amino, $C_{1-6}$alkylaminocarbonyl, di($C_{1-6}$alkyl)aminocarbonyl, $C_{1-6}$alkylcarbonylamino, ($C_{1-6}$alkyl)($C_{1-6}$alkylcarbonyl)amino, —N(H)—C(NH)(NH$_2$), $C_{1-6}$alkylcarbonyloxy, $C_{1-6}$alkoxycarbonyl, or a three- to seven-membered monocyclic ring system which may be aromatic, saturated or unsaturated non-aromatic, which may contain from 1 to 4 hetero atoms selected from nitrogen, oxygen and sulfur, which may be attached directly or via bivalent oxygen or carbonyl, and which may in turn be substituted once or more than once by halogen, cyano, hydroxy, $C_{1-4}$alkyl, $C_{1-4}$alkoxy or $C_{1-4}$halogenalkyl; each $R_{15}$ and $R_{19}$ independently is halogen, cyano, hydroxy, —SH, amino, $C_{1-6}$alkoxy, $C_{1-4}$alkoxy-$C_{1-4}$alkoxy, $C_{1-4}$alkoxy-$C_{1-4}$alkoxy-$C_{1-4}$alkoxy, $C_{1-6}$alkylthio, —C(O)OH, $C_{1-6}$alkylamino, di($C_{1-6}$alkyl)amino, $C_{1-6}$alkylaminocarbonyl, di($C_{1-6}$alkyl)aminocarbonyl, $C_{1-6}$alkylcarbonylamino, ($C_{1-6}$alkyl)($C_{1-6}$alkylcarbonyl)amino, $C_{1-6}$alkylcarbonyloxy, $C_{1-6}$alkoxycarbonyl; $C_{1-6}$alkyl, $C_{1-6}$halogenalkyl, $C_{1-6}$cyanoalkyl, $C_{1-6}$hydroxyalkyl, $C_{1-4}$alkoxy-$C_{1-4}$alkyl;

q is an integer from 1 to 10;
r is an integer from 1 to 10;
s is an integer from 1 to 6;
t is an integer from 1 to 6;
Z is a saccharide moiety selected from the group consisting of a monosaccharide moiety and an oligosaccharide moiety, wherein Z is attached through a hydroxyl oxygen atom of Z; in free form or in salt form.

In one embodiment, the invention provides a compound of formula I, wherein $R_1$ is $C_{1-4}$alkyl.

In one embodiment, the invention provides a compound of formula I, wherein $R_1$ is methyl or ethyl.

In one embodiment, the invention provides a compound of formula I, wherein $R_1$ is methyl.

In one embodiment, the invention provides a compound of formula I, wherein m is 0, 1, 2 or 3; and n is 0, 1 or 2.

In one embodiment, the invention provides a compound of formula I, wherein $R_2$ and $R_3$ independently are halogen, cyano, hydroxy, amino, $C_{1-4}$alkyl; $C_{1-4}$halogenalkyl or $C_{1-4}$alkoxy;
m is 0, 1, 2 or 3; and
n is 0, 1 or 2.

In one embodiment, the invention provides a compound of formula I, wherein m and n are both 0.

In one embodiment, the invention provides a compound of formula I, wherein $R_4$ and $R_5$ are both hydrogen.

In one embodiment, the invention provides a compound of formula I, wherein $R_6$ is fluoro and is 0, 1 or 2.

In one embodiment, the invention provides a compound of formula I, wherein p is 0.

In one embodiment, the invention provides a compound of formula I, wherein $R_7$ is —$C(O)R_8$.

In one embodiment, the invention provides a compound of formula I, wherein $R_7$ is —$C(O)R_8$; and $R_8$ is $C_{1-20}$alkyl which may be substituted once or more than once by $R_{12}$.

In one embodiment, the invention provides a compound of formula I, wherein $R_7$ is —$C(O)R_8$; and $R_8$ is $C_{1-20}$alkyl.

In one embodiment, the invention provides a compound of formula I, wherein $R_7$ is —$C(O)R_8$; and $R_8$ is a natural amino acid, wherein said natural amino acid is attached through a —C(O)OH carbonyl of said natural amino acid.

In one embodiment, the invention provides a compound of formula I, wherein $R_7$ is —$C(O)R_8$; and $R_8$ is a three- to seven-membered monocyclic ring system which may be aromatic, saturated or unsaturated non-aromatic, which may contain from 1 to 4 hetero atoms selected from nitrogen, oxygen and sulfur, and which may be substituted once or more than once by $R_{15}$.

In one embodiment, the invention provides a compound of formula I, wherein each $R_{12}$ independently is hydroxy, amino, $C_{1-6}$alkoxy, $C_{1-4}$alkoxy-$C_{1-4}$alkoxy, $C_{1-4}$alkoxy-$C_{1-4}$alkoxy-$C_{1-4}$alkoxy, —C(O)OH, $C_{1-6}$alkylamino, di($C_{1-6}$alkyl)amino, aminocarbonyl, $C_{1-4}$alkylaminocarbonyl, di($C_{1-6}$alkyl)aminocarbonyl, $C_{1-6}$alkylcarbonylamino, ($C_{1-6}$alkyl)($C_{1-6}$alkylcarbonyl)amino, —N(H)—C(NH)(NH$_2$), $C_{1-6}$alkylcarbonyloxy, $C_{1-6}$alkoxycarbonyl, or a three- to seven-membered monocyclic ring system which may be aromatic, saturated or unsaturated non-aromatic, which may contain from 1 to 4 hetero atoms selected from nitrogen, oxygen and sulfur, which may be attached directly or via bivalent oxygen or carbonyl, and which may in turn be substituted once or more than once by halogen, cyano, hydroxy, $C_{1-4}$alkyl, $C_{1-4}$alkoxy or $C_{1-4}$halogenalkyl.

In one embodiment, the invention provides a compound of formula I, wherein each $R_{12}$ independently is hydroxy, amino, $C_{1-6}$alkoxy, $C_{1-4}$alkoxy-$C_{1-4}$alkoxy, $C_{1-4}$alkoxy-$C_{1-4}$alkoxy-$C_{1-4}$alkoxy, —C(O)OH, $C_{1-6}$alkylamino, di($C_{1-6}$alkyl)amino, $C_{1-6}$alkylaminocarbonyl, di($C_{1-6}$alkyl)aminocarbonyl, $C_{1-6}$alkylcarbonylamino, ($C_{1-6}$alkyl)($C_{1-6}$alkylcarbonyl)amino, —N(H)—C(NH)(NH$_2$), $C_{1-6}$alkylcarbonyloxy, $C_{1-6}$alkoxycarbonyl, or a three- to seven-membered monocyclic ring system which may be aromatic, saturated or unsaturated non-aromatic, which may contain from 1 to 4 hetero atoms selected from nitrogen, oxygen and sulfur, which may be attached directly or via bivalent oxygen or carbonyl, and which may in turn be substituted once or more than once by halogen, cyano, hydroxy, $C_{1-4}$alkyl, $C_{1-4}$alkoxy or $C_{1-4}$halogenalkyl.

In one embodiment, the invention provides a compound of formula I, wherein $R_7$ is —$C(O)R_8$; $R_8$ is $C_{1-6}$alkyl which is substituted once or more than once by $R_{12}$; and wherein each $R_{12}$ is amino, morpholino, pyrrolidino, $C_{1-6}$alkylamino, aminocarbonyl, $C_{1-6}$alkylaminocarbonyl or $C_{1-6}$alkylcarbonyloxy.

In one embodiment, the invention provides a compound of formula I, wherein $R_7$ is —$C(O)R_8$; $R_8$ is $C_{1-6}$alkyl which is substituted once or more than once by $R_{12}$; and wherein each $R_{12}$ is amino, $C_{1-6}$alkylaminocarbonyl or $C_{1-6}$alkylcarbonyloxy.

In one embodiment, the invention provides a compound of formula I, wherein $R_7$ is —$C(O)R_8$; $R_8$ is $C_{1-6}$alkyl which is substituted once or more than once by $R_{12}$; and wherein each $R_{12}$ is amino or $C_{1-6}$alkylcarbonyloxy.

In one embodiment, the invention provides a compound of formula I, wherein $R_7$ is —$R_9$.

In one embodiment, the invention provides a compound of formula I, wherein $R_7$ is —$R_9$; and $R_9$ is $C_{1-10}$alkyl.

In one embodiment, the invention provides a compound of formula I, wherein $R_7$ is —$P(OR_{10})(OR_{11})$.

In one embodiment, the invention provides a compound of formula I, wherein $R_7$ is —$P(OR_{10})(OR_{11})$; and $R_{10}$ and $R_{11}$ independently are both ethyl.

In one embodiment, the invention provides a compound of formula I, wherein $R_7$ is —Z, —C(O)—(CH)$_q$—O—Z, —(CH$_2$)$_r$—O—Z or —(CH$_2$)$_s$—O—(CH$_2$)$_t$—O—Z.

In one embodiment, the invention provides a compound of formula I, wherein $R_7$ is —Z.

In one embodiment, the invention provides a compound of formula I, wherein $R_7$ is —Z; and Z is a monosaccharide moiety, wherein Z is attached through a hydroxyl oxygen atom of Z.

In one embodiment, the invention provides a compound of formula I, wherein $R_7$ is D-glucose, wherein said D-glucose is attached through a hydroxyl oxygen atom.

In one embodiment, the invention provides a compound of formula I, wherein $R_7$ is —C(O)—(CH$_2$)$_q$—O—Z.

In one embodiment, the invention provides a compound of formula I, wherein $R_7$ is —C(O)—(CH$_2$)$_q$—O—Z; q is an integer from 1 to 10, e.g. 1 to 6, e.g. 1 to 4; and is a monosaccharide moiety, wherein Z is attached through a hydroxyl oxygen atom of Z.

In one embodiment, the invention provides a compound of formula I, wherein $R_7$ is —(CH$_2$)$_r$—O—Z.

In one embodiment, the invention provides a compound of formula I, wherein $R_7$ is —(CH$_2$)$_r$—O—Z; r is an integer from 1 to 10, e.g. 1 to 6, e.g. 1 to 4; and is a monosaccharide moiety, wherein Z is attached through a hydroxyl oxygen atom of Z.

In a further aspect, the invention also provides a process ("Process 1") for the production of a compound of the formula Ia

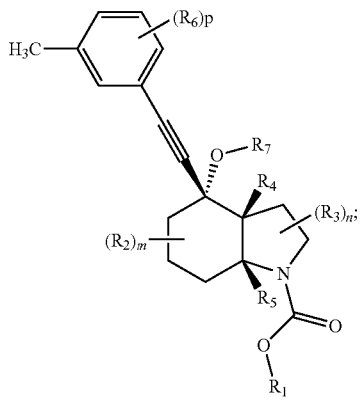

(Ia)

in which $R_1$, $R_2$, $R_3$, $R_4$, $R_5$, $R_6$, m, n and p are as defined under formula I, and $R_7$ is —C(O)$R_8$,
in which $R_8$ is as defined under formula I,
or a salt thereof,
which comprises reacting a compound of formula IIa

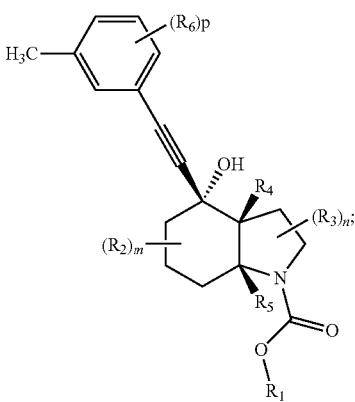

(IIa)

in which $R_1$, $R_2$, $R_3$, $R_4$, $R_5$, $R_6$, m, n and p are as defined under formula I,
or a salt thereof,
with a compound of formula IIIa

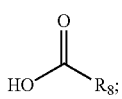

(IIIa)

in which $R_8$ is as defined under formula I,
or a salt thereof,
in the presence of dicyclohexylcarbodiimide or 1-ethyl-3-(3-dimethylaminopropyl)carbodiimide (e.g. dicyclohexylcarbodiimide), and a dialkyl-amino-pyridine (e.g. 4-dimethylaminopyridine), and a suitable solvent (e.g. dichlormethane), to form the compound of formula Ia; and optionally converting the compound of formula Ia to a salt thereof.

In a further aspect, the invention also provides a process ("Process 2") for the production of compound of the formula I wherein $R_7$ is —Z by condensation of a compound of formula IIa (said compound being described in the definition of Process 1 above) with an oxygen protected thioglycoside donor with subsequent cleavage of oxygen protecting groups in a second step.

To give an example, more specifically, in a first step, 1 mol equivalent of the compound described in Example 1.0 and 1.2 mol equivalents of ethyl-tetra-O-(4-methoxybenzyl)-β-D thioglucopyranoside are dissolved in methylenehloride in the presence of 4 Å-molecular sieves (5 g/10 mmol of Example 1.0). The mixture is stirred at room temperature under argon for 30 minutes. Subsequently, the mixture is cooled to −30° C. and 1.5 mol equivalents of N-iodosuccinimide and trifluoromethane sulfonate (30 μL/10 mmol of Example 1.0) are added. This mixture is stirred at the same temperature for 45 minutes, then filtered through Celite and washed with methylenehloride. The organic layer is washed, dried, evaporated and the crude mass subjected to product isolation by chromatography to yield (3aR,4S,7aR)-4-m-tolylethynyl-4-[4,5,6-tris-(4-methoxy-benzyloxy)-3-(4-methoxy-benzyloxymethyl)-tetrahydro-pyran-2-yloxy]-octahydro-indole-1-carboxylic acid methyl ester (alias (3aR,4S,7aR)-4-m-tolylethynyl-4-tetra-O-(4-methoxybenzyl)-β-D-glucopyranoside-2-oxy)-octahydro-indole-1-carboxylic acid methyl ester).

In a second step, this O-protected compound is deprotected e.g. by treatment in the presence of 1.3 mol equivalents of 2,3-dichloro-5,6-dicyano-p-benzoquinone (DDQ) in acetonitrile under photo irradiation using a long wavelength UV light (365 nm, 100 W) at room temperature for 12 hours. The desired product is purified by chromatography to yield (3aR, 4S,7aR)-4-m-tolylethynyl-4-((2R,3R,4S,5S,6R)-3,4,5-trihydroxy-6-hydroxymethyl-tetrahydro-pyran-2-yloxy)-octahydro-indole-1-carboxylic acid methyl ester (alias (3aR,4S, 7aR)-4-m-tolylethynyl-4-β-D-glucopyranosyl-2-oxy)-octahydro-indole-1-carboxylic acid methyl ester).

Further compounds of formula (I) may be obtainable from compounds of formula I prepared as described above (e.g. compounds of formula Ia prepared via Process 1) by reduction, oxidation and/or other functionalization of resulting compounds and/or by cleavage of any protecting group(s) optionally present, and of recovering the so obtainable compound of the formula (I).

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Compounds of the formula I can also be prepared by further conventional processes, e.g. as described in the Examples, which processes are further aspects of the invention.

The starting materials of Process 1 and/or Process 2 are known (e.g. compounds of formula IIa from WO02006108591 and WO2006010591, respectively) or may be prepared according to conventional procedures starting from known compounds, for example as described in the Examples.

In another aspect, the invention provides a pharmaceutical composition comprising a therapeutically effective amount of a compound of the invention and one or more pharmaceutically acceptable carriers.

The pharmaceutical composition can be formulated for particular routes of administration such as oral administration, parenteral administration, and rectal administration, etc. In addition, the pharmaceutical compositions of the invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by mGluR5 receptors, or (ii) associated with mGluR5 receptor activity, or (iii) characterized by abnormal activity of mGluR5 receptors; or (2) reducing or inhibiting the activity of mGluR5 receptors; or (3) reducing or inhibiting the expression of mGluR5 receptors. In another non-limiting embodiment, the term "a therapeutically effective amount" refers to the amount of the compound of the invention that, when administered to a cell, or a tissue, or a non-cellular biological material, or a medium, is effective to at least partially reducing or inhibiting the activity of mGluR5 receptors; or at least partially reducing or inhibiting the expression of mGluR5 receptors.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

The compounds of the invention in free form or in pharmaceutically acceptable salt form, exhibit valuable pharmacological properties, e.g. a mGluR5 antagonism is effected when administered to patients, e.g. as indicated in in-vitro and/or in-vivo tests as provided in the sections below. Therefore, the compounds of the invention in free form or in pharmaceutically acceptable salt form are indicated for therapy.

The compounds of the invention may be therefore useful in the prevention, treatment or delay of progression of disorders associated with irregularities of the glutamatergic signal transmission, of the gastro-intestinal and urinary tract and of nervous system disorders mediated full or in part by mGluR5.

Disorders associated with irregularities of the glutamatergic signal transmission are for example epileptogenesis including neuronal protection after status epilepticus, cerebral ischemias, especially acute ischemias, ischemic diseases of the eye, muscle spasms such as local or general spasticity, skin disorders, obesity disorders and, in particular, convulsions or pain.

Disorders of the gastro-intestinal tract include Gastro-Esophageal Reflux Disease (GERD), Functional Gastro-intestinal Disorders and Post-operative Ileus.

Functional Gastro-intestinal Disorders (FGIDs) are defined as chronic or recurrent conditions associated with abdominal symptoms without organic cause using conventional diagnostic measures. A cardinal symptom present in many FGIDs is visceral pain and/or discomfort. FGIDs include functional dyspepsia (FD), functional heartburn (a subset of GERD), irritable bowel syndrome (IBS), functional bloating, functional diarrhea, chronic constipation, functional disturbancies of the biliary tract as well as other conditions according to Gut 1999; Vol. 45 Suppl. II. A disorder of particular interest is GERD.

Post-operative leus is defined as failure of aboral passage of intestinal contents due to transient impairment of GI motility following abdominal surgery.

Disorders of the Urinary Tract comprise conditions associated with functional disturbancies and/or discomfort/pain of the urinary tract. Examples of disorders of the urinary tract include but are not limited to incontinence, benign prostatic hyperplasia, prostatitis, detrusor hyperreflexia, outlet obstruction, urinary frequency, nocturia, urinary urgency, overactive bladder (OAB), pelvic hypersensitivity, urge incontinence, urethritis, prostatodynia, cystitis, idiopathic bladder hypersensitivity and the like. OAB is a syndrome characterized by urgency, with or without urinary incontinence, and usually with increased voiding frequency and nocturia.

Nervous system disorders mediated full or in part by mGluR5 are for example acute, traumatic and chronic degenerative processes of the nervous system, such as Parkinson's disease, Parkinson's dyskinesia (e.g. L-dopa induced dyskinesia), dyskinesias induced by neuroleptics (e.g. tardive dyskenisia), Tic disorders, Tourette Syndrome, Restless Leg Syndrome, Periodic Limb Movement Syndromes, senile dementia, Alzheimer's disease, Huntington's chorea, amyotrophic lateral sclerosis, multiple sclerosis and fragile X syndrome, substance-related disorders, psychiatric diseases such as schizophrenia, affective and anxiety disorders, attention deficit disorders and cognitive dysfunction associated with these and other CNS disorders. Substance-related disorders include substance abuse, substance dependence and substance withdrawal disorders, e.g. nicotine withdrawal. Anxiety disorders includes panic disorder, social and specific phobias, anxiety, obsessive compulsive disorder (OCD), post traumatic stress disorder (PTSD) and generalized anxiety disorder (GAD). Affective disorders include depressive (major depression, dysthymia, depressive disorders NOS) and bipolar disorders (bipolar I and II disorders). Cognitive dysfunction associated with these and other CNS disorders include deficits and abnormalities in attention and vigilance, executive functions and memory (for instance working memory and episodic memory). Other disorders which are mediated fully or in part by mGluR5 are pain and itch.

A disorder of particular interest is L-dopa induced dyskinesia in Parkinsons Disease.

The compounds of the invention, especially the compounds as defined in group P under Embodiment 7, are useful in the treatment, prevention or delay of progression of dyskinesias in Parkinsons Disease, especially L-dopa induced dyskinesia in Parkinsons Disease.

Dyskinesia in Parkinsons Disease often, although not exclusively, occurs as a side-effect of treatment of Parkinson's Disease with levodopa (L-dopa), a precursor of dopamine. Characteristics of such dyskinesia include motor impairment, e.g. the appearance of slow and uncoordinated involuntary movements, shaking, stiffness and problems walking. Patients treated with L-dopa often have reduced symptoms of Parkinson's Disease but they experience increasing difficulties to remain standing or even sitting. After prolonged use of L-dopa, a majority of patients develop dyskinesia.

Dyskinesia can occur at any time during the cycle of treatment with L-dopa. In one embodiment, the compounds of the invention are for the treatment of dyskinesia which occurs at the time of peak L-dopa plasma concentrations in the patient. In one embodiment, the compounds of the invention are for the treatment of dyskinesia which occurs when the L-dopa plasma concentrations in a patient rise or fall (diphasic dyskinesia).

Dyskinesia can also develop in Parkinson's disease sufferers who do not take L-dopa. In one embodiment, the compounds of the invention are for the treatment of non-L-dopa induced Parkinson's dyskinesia.

Treatment with a compound of the invention, especially with a compound as defined in group P, may comprise a reduction in the characteristics associated with Parkinson's dyskinesia, including for example, although not limited to, a reduction in the scale of involuntary movements, a reduction in the number of involuntary movements, an improvement in the ability to carry out normal tasks, an improved ability to walk, increased period of time between episodes of dyskinesia.

In the case of prophylactic treatment, the compounds of the invention, especially the compounds as defined in group P may be used to delay or prevent the onset of Parkinson's dyskinesia.

For the above-mentioned indications (the conditions and disorders) the appropriate dosage will vary depending upon, for example, the compound employed, the host, the mode of administration and the nature and severity of the condition being treated. However, in general, satisfactory results in animals are indicated to be obtained at a daily dosage of from about 0.01 to about 100 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 1 to about 400 mg, most preferably from about 10 to about 100 mg of the compound of the invention conveniently administered, for example, in divided doses up to four times a day.

For use according to the invention, a compound of the invention, especially a compound as defined in group P, may be administered as single active agent or in combination with other active agents, in any usual manner, e.g. orally, for example in the form of tablets or capsules, or parenterally, for example in the form of injection solutions or suspensions. A combination comprising a compound of the invention and another active agent will be referred to as "combination of the invention".

In the case of Parkinson's dyskinesia induced by L-dopa, the compound of the invention, especially being a compound as defined in group P, will be combined with L-dopa and optionally with at least one active agent selected from the group consisting of a dopa decarboxylase inhibitor, a catechol-O-methyl transferase inhibitor, a dopamine agonist, a monoamine oxidase-B inhibitor, an adrenergic drug, a drug for obstructed airway disorders, a beta blocking agent, an alpha-adrenoreceptor antagonist, an angiotensin II antagonist, an anticholinergic, an anticholinesterase, an antidepressant, an anti-inflammatory agent, an anti-rheumatic agent, an antimigraine agent, an anxiolytic, a barbiturate, a barbiturate derivate, a belladonna alkaloid, a tertiary amine and a benzothiazepine derivative.

Dopa decarboxylase inhibitors are, for example, carbidopa or benserazide.

Catechol-O-methyl transferase inhibitors are, for example, tolcapone or entacapone.

Dopamine agonists are, for example, bromocriptine, pergolide, pramipexole, ropinirole, cabergoline, apomorphine or lisuride.

Monoamine oxidase-B inhibitors are, for example, selegiline, rasagiline.

Adrenergics and/or drugs for obstructed airway disorders are, for example, Budesonide with formoterol fumarate, Combivent, Sertide mite or Salbutamol.

Beta blocking agents are, for example, Acebutolol, Acebutolol hydrochloride, Atenolol, Betaxolol, Betaxolol hydrochloride, Bisoprolol, Bisoprolol fumarate, Bisoprolol hemifumarate, Carvedilol, Cosopt, Levobunolol hydrochloride, Metoprolol, Metoprolol succinate, Metoprolol tartrate, Propranolol, Propranolol hydrochloride, Sotalol, Sotalol hydrochloride, Tenoretic, Timolol, Timolol maleate or Timpilo.

Alpha-adrenoreceptor antagonists are, for example, Alfuzosin, Alfuzosin hydrochloride, Doxazosin, Doxazosin mesilate, Tamsulosin, Tamsulosin hydrochloride, Terazosin or Terazosin hydrochloride.

Angiotensin II antagonists are, for example, Candesartan cilexetil, Irbesartan, Losartan, Losartan potassium, Olmesartan medoxomil, Telmisartan or Valsartan.

Combinations of Angiotensin II antagonists are, for example, Blopress plus, Co-diovan, Hyzaar or Karvea hct.

Anticholinergics are, for example, Ibratropium bromide or Tiotropium bromide.

Anticholinesterases are, for example, Donepezil hydrochloride.

Antidepressants are, for example, Amitriptyline, Amitriptyline hydrochloride, Bupropion hydrochloride, Citalopram, Citalopram hydrobromide, Cyclobenzaprine, Cyclobenzaprine hydrochloride, Escitalopram, Escitalopram oxalate, Fluoxetine, Fluvoxamine maleate, Imipramine hydrochloride, Mirtazapine, Paroxetine, Paroxetine hydrochloride, Sertraline, Sertraline hydrochloride, Trazodone, Trazodone hydrochloride, Venlafaxine or Venlafaxine hydrochloride.

Antiepileptics are, for example, Carbamazepine, Clonazepam, Gabapentin, Phenobarbital, Phenyloin, Pregabalin or Topiramate.

Anti-inflammatory and/or anti-rheumatic agents are, for example, Betamethasone, Betamethasone valerate, Cortisone, Cortisone acetate, Desonide, Diclofenac, Diclofenac sodium, Flurbiprofen, Hydrocortisone, Indometacin, Salicylic acid, Triamcinolone acetonide, Aceclofenac, Aflexa, Arthrotec, Carbager-plus, Celecoxib, Glucosamine, Glucosamine sulfate, Glucosamine with chondroitin, Ibuprofen, Ketoprofen, Meloxicam, Naproxen, Naproxen sodium, Nimesulide, Osteo bi-flex or Sulindac.

Antimigraine preparations are, for example, Naratriptan hydrochloride, Rizatriptan or Sumatriptan.

Anxiolytics are, for example, Alprazolam, Bromazepam, Clonazepam, Clorazepate dipotassium, Diazepam, Ethyl loflazepate, Hydroxyzine, Hydroxyzine hydrochloride, Lorazepam, Oxazepam or Tetrazepam.

Barbiturates and/or barbiturate derivates are, for example, Phenobarbital or Phenobarbital.

Belladonna alkaloids and/or tertiary amines are, for example, Hyoscyamine sulfate Benzodiazepine derivatives and related drugs are, for example, Alprazolam, Bromazepam, Clonazepam, Clorazepate dipotassium, Diazepam, Ethyl loflazepate, Lorazepam, Lormetazepam, Oxazepam, Temazepam, Tetrazepam, Triazolam, Eszopiclone, Zolpidem, Zolpidem tartrate or Zopiclone.

Benzothiazepine derivatives are, for example, Diltiazem or Diltriazem hydrochloride.

In one embodiment of the invention a specific combination of the invention is used. Said combination comprises:

A compound of the invention, especially a compound as defined in group P; and L-dopa.

In one embodiment of the invention a specific combination of the invention is used. Said combination comprises:

A compound of the invention, especially a compound as defined in group P;
L-dopa; and
at least one active agent selected from the group consisting of:
carbidopa, benserazide, tolcapone, entacapone, bromocriptine, pergolide, pramipexole, ropinirole, cabergoline, apomorphine, lisuride, selegiline, rasagiline, Budesonide with formoterol fumarate, Combivent, Sertide mite, Salbutamol, Acebutolol, Acebutolol hydrochloride, Atenolol, Betaxolol, Betaxolol hydrochloride, Bisoprolol, Bisoprolol fumarate, Bisoprolol hemifumarate, Carvedilol, Cosopt, Levobunolol hydrochloride, Metoprolol, Metoprolol succinate, Metoprolol tartrate, Propranolol, Propranolol hydrochloride, Sotalol, Sotalol hydrochloride, Tenoretic, Timolol, Timolol maleate, Timpilo, Alfuzosin, Alfuzosin hydrochloride, Doxazosin, Doxazosin mesilate, Tamsulosin, Tamsulosin hydrochloride, Terazosin, Terazosin hydrochloride, Candesartan cilexetil, Irbesartan, Losartan, Losartan potassium, Olmesartan medoxomil, Telmisartan, Valsartan, Blopress plus, Co-diovan, Hyzaar, Karvea hct, Ibratropium bromide, Tiotropium bromide, Donepezil hydrochloride, Amitriptyline, Amitriptyline hydrochloride, Bupropion hydrochloride, Citalopram, Citalopram hydrobromide, Cyclobenzaprine, Cyclobenzaprine hydrochloride, Escitalopram, Escitalopram oxalate, Fluoxetine, Fluvoxamine maleate, Imipramine hydrochloride, Mirtazapine, Paroxetine, Paroxetine hydrochloride, Sertraline, Sertraline hydrochloride, Trazodone, Trazodone hydrochloride, Venlafaxine, Venlafaxine hydrochloride, Carbamazepine, Clonazepam, Gabapentin, Phenobarbital, Phenyloin, Pregabalin, Topiramate, Betamethasone, Betamethasone valerate, Cortisone, Cortisone acetate, Desonide, Diclofenac, Diclofenac sodium, Flurbiprofen, Hydrocortisone, Indometacin, Salicylic acid, Triamcinolone acetonide, Aceclofenac, Aflexa, Arthrotec, Carbager-plus, Celecoxib, Glucosamine, Glucosamine sulfate, Glucosamine with chondroitin, Ibuprofen, Ketoprofen, Meloxicam, Naproxen, Naproxen sodium, Nimesulide, Osteo bi-flex or Sulindac Antimigraine preparations are, for example, Naratriptan hydrochloride, Rizatriptan, Sumatriptan, Alprazolam, Bromazepam, Clonazepam, Clorazepate dipotassium, Diazepam, Ethyl loflazepate, Hydroxyzine, Hydroxyzine hydrochloride, Lorazepam, Oxazepam, Tetrazepam, Phenobarbital, Phenobarbital, Hyoscyamine sulfate, Alprazolam, Bromazepam, Clonazepam, Clorazepate dipotassium, Diazepam, Ethyl loflazepate, Lorazepam, Lormetazepam, Oxazepam, Temazepam, Tetrazepam, Triazolam, Eszopiclone, Zolpidem, Zolpidem tartrate, Zopiclone, Diltiazem and Diltriazem hydrochloride.

An example of a combination is a compound as defined in group P, L-dopa, and the dopa decarboxylase inhibitor carbidopa.

Another example of a combination is a compound as defined in group P, L-dopa, and entacapone.

Another example of a combination is a compound as defined in group P, L-dopa, entacapone, and carbidopa; an example of such a combination is a combination of a compound as defined in group P and Stalevo®.

An example of a combination is the first compound as defined in group P, i.e. (3aR,4S,7aR)-4-(2-Dimethylamino-acetoxy)-4-m-tolylethynyl-octahydro-indole-1-carboxylic acid methyl ester, L-dopa, and the dopa decarboxylase inhibitor carbidopa.

Another example of a combination is the first compound as defined in group P, i.e. (3aR,4S,7aR)-4-(2-Dimethylamino-acetoxy)-4-m-tolylethynyl-octahydro-indole-1-carboxylic acid methyl ester, L-dopa, and entacapone.

Another example of a combination is the first compound as defined in group P, i.e. (3aR,4S,7aR)-4-(2-Dimethylamino-acetoxy)-4-m-tolylethynyl-octahydro-indole-1-carboxylic acid methyl ester, L-dopa, entacapone, and carbidopa; an example of such a combination is a combination of the first compound as defined in group P, i.e. (3aR,4S,7aR)-4-(2-Dimethylamino-acetoxy)-4-m-tolylethynyl-octahydro-indole-1-carboxylic acid methyl ester, and Stalevo®.

The agents of the present invention may also be useful for treating or preventing migraine.

The agents of the present invention may also be useful for inflammatory diseases, such as pain, inflammation and/or oedema consequential to trauma, for example associated with burns, sprains, fractures or the like, inflammatory airways diseases, such as COPD, asthma, rhinitis, inflammatory bowel disease, cystitis, uveitis, inflammatory skin disorders, such as psoriasis or eczema, rheumatoid arthritis, use as a smooth muscle relaxant, for example for the treatment of spasms of the gastro-intestinal tract or uterus, for example in the therapy of Crohn's disease, ulcerative collitis or pancreatitis, or for the treatment of muscle spasticity and tremor, for example in multiple sclerosis, teno-synovitis, gout, ocular disorders, for example glaucoma, cough.

The agents of the present invention may also be useful for treating cognitive impairment and/or attention deficit disorder.

Cognitive dysfunction include deficits and abnormalities in attention and vigilance, executive functions and memory (for instance working memory and episodic memory). Other disorders relating to cognitive dysfunction include sleep related breathing disorders (SRBD), behavioral impairments, information processing deficits and age-related disorders. Further examples falling of cognitive impairment and/or attention deficit disorders include: Attention-deficit hyperactivity disorder (ADHD), childhood ADHD, adult ADHD, excess daytime somnolence, sleep apnea, shift-worker's sleep-wake cycle disruption, traumatic brain injury, neurodegenerative disorders with associated memory and cognitive problems (such as Alzheimer's disease, Lewy body dementia, senile dementia, vascular dementia, Parkinson's disease), chronic fatigue syndrome, fatigue associated with sleep deprivation or prolonged wakefulness, age-related decline in memory and cognitive function (such as mild cognitive impairment), cognitive impairment associated with mood disorders (such as depression) and anxiety, schizophrenia, day time sleepiness associated with narcolepsy.

Furthermore, the agents of the present invention may provide treatment for or improve of the cognitive enhancement of a subject. The term "cognitive enhancement" includes, but is not limited to, cognition enhancement, vigilance, counteracting effects of fatigue, enhancing alertness, attention, memory (working, episodic), learning ability, reaction time, cognitive performance enhancement, excess daytime somnolence, reversal of information processing deficits, improvement of disorganization, i.e. improving organizational skills/level of organizational ability.

The agents of the present invention may also be useful for treating pervasive developmental disorders (PDD). PDD is a group of diseases characterized by a delay in the developement of socialization and communications skills. The following diseases are part of the PDD: Autism, Asperger's syndrome, childhood disintegrative disorder, and Rett's syndrome, and fragile X. The main symptomatology are: Autistic-like behavior, repetitive behavior (OCD), in some cases irritability, and ADHS. Fragile X Syndrome have two diferent genotype-phenotype: Full mutation (mental retardation, ADHD, autism, and anxiety), partial mutation (tremor-ataxia, parkinsonism, anxiety). A disorder of particular interest is fragile X syndrome.

The compounds of the invention may be useful for the prevention of the above-mentioned conditions and disorders.

The compounds of the invention may be useful for the treatment of the above-mentioned conditions and disorders.

The compounds of the invention may be useful for the delay of progression of the above-mentioned conditions and disorders.

Compounds of the invention may be especially useful in the treatment of an indication selected from: L-dopa induced dyskinesias in Parkinsons Disease and fragile X syndrome.

Thus, as a further embodiment, the invention provides the use of a compound of formula (I) or a pharmaceutically acceptable salt thereof as a medicament.

As a further embodiment, the invention provides the use of a compound of formula (I) or a pharmaceutically acceptable salt thereof in therapy.

In a further embodiment, the therapy is selected from a disease which is ameliorated by inhibition of mGluR5. In another embodiment, the disease is selected from the aforementioned list, e.g. L-dopa induced dyskinesias in Parkinsons Disease and fragile X syndrome.

In another embodiment, the invention provides a method of treating a disease which is ameliorated by inhibition of mGluR5 comprising administration of a therapeutically acceptable amount of a compound of formula (I) or a pharmaceutically acceptable salt thereof. In a further embodiment, the disease is selected from the afore-mentioned list, suitably L-dopa induced dyskinesias in Parkinsons Disease and fragile X syndrome.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound of the invention can be assessed by in vitro & in vivo methods described herein.

The compound of the invention may be administered either simultaneously with, or before or after, at least one other therapeutic agent. The compound of the invention may be administered separately, by the same or different route of administration, or together in the same pharmaceutical composition.

The following Examples illustrate the invention, but do not limit it.

ABBREVIATIONS

AcOH acetic acid
Boc tert-butoxycarbonyl
d day(s)
DCM dichloromethane
DCC dicyclohexylcarbodiimide
DMF dimethylformamide
DMSO dimethylsulfoxide
ED50 50% effect-dose
EDC 1-(3-dimethylaminopropyl)-3-ethylcarbodlimide
ESIMS electrospray ionization mass spectrometry
EtOAc ethyl acetate
$Et_2O$ diethyl ether
h hour(s)
Hex hexane
HOBt 1-Hydroxybenzotriazole trihydrate
HPLC high pressure liquid chromatography
i.p. intra-peritoneal (administration)
LCMS liquid chromatography mass spectroscopy
min minute(s)
NBoc Nitrogen-bound tert-butyloxycarbonyl group
NMR nuclear magnetic resonance spectrometry
p.o. per os (oral administration)
quant. quantitative
Rt retention time
rt room temperature
s.c. sub-cutaneous (administration)
THF tetrahydrofuran
TFA trifluoroacetic acid
Ts Tosyl
UPLC ultra performance liquid chromatography
Chromatography and LC/MS Methods:
1. Flash Chromatography System
ISCO System, CombiFlash Companion; IG Instrumenten-Gesellschaft AG. Cartusch System.
ISCO System, CombiFlash Rf; IG Instrumenten-Gesellschaft AG. Cartusch System.
2. HPLC Preparative Chromatography System
Gilson System, Configuration: 331 Pump, 332 Pump, UVIVlS-155 and GX281 FC.
3. UPLC-MS System (Analytical)
Waters Acquity UPLC
UPLC/MS—Method I
Column: Water Acquity HSS T3 1.8 um, 2.1×50 mm;
Eluent: Water (+0.05% formic acid+3.75 mM ammonium acetate):acetonitrile (+0.04% formic acid) from 98:2 to 2:98 in 1.4 min, hold for 0.75 min
Flow rate 1.2 ml/min; temperature 50° C.
UPLC/MS—Method II
Column: Water Acquity HSS T3 1.8 um, 2.1×50 mm;
Eluent: Water (+0.05% formic acid+3.75 mM ammonium acetate):acetonitrile (+0.04% formic acid) from 98:2 to 2:98 in 2.8 min, hold for 1.70 min, re-equilibrate for 0.5 min Flow rate 1.2 ml/min temperarure 50° C.
4. LC-MS System (Analytical)
Agilent 1100 Series
LC/MS—Method I
Column: PHENOMENEX Gemini C 18; 100 A, 3.0 um, 2.0×100 mm;
Eluent: Water (+0.1% TFA):acetonitrile (+0.1% TFA) from 95:5 to 5:95 in 8.0 min, hold 95% B for 1.5 min, re-equilibrate for 0.5 min;
Flow rate 0.6 ml/min; temperature 50° C.
LC/MS—Method II
Column: VWR Chromolith Performance RP-18e, 3.5 um, 3.0×100 mm;

Eluent: Water (+0.05% TFA):acetonitrile from 95:5 to 5:95 in 8.0 min, hold 95% B for 1.5 min, re-equilibrate for 0.5 min;
Flow rate 1.0 ml/min; temperature 37° C.
LC/MS—Method III
Column: VWR Chromolith SpeedRod RP-18e, 3.5 um, 4.6×50 mm;
Eluent: Water (+0.05% TFA):acetonitrile from 95:5 to 5:95 in 8.5 min, hold 95% B for 1.0 min, re-equilibrate for 2.0 min;
Flow rate 1.0 ml/min; temperature 37° C.
LC/MS—Method IV
Column: WATERS Xselect CSH C18, 3.5 um, 4.6×50 mm;
Eluent: Water:acetonitrile:0.1% formic acid from 90:5:5 to 0:95:5 in 6.0 min, hold 95% B for 3.5 min, re-equilibrate for 1.0 min;
Flow rate 1.0 ml/min; temperature 37° C.
LC/MS—Method V
Column: VWR Chromolith SpeedRod RP-18e, 3.5 um, 4.6×50 mm;
Eluent: Water (+0.05% TFA):acetonitrile from 95:5 to 5:95 in 4.0 min, hold 95% B for 6.0 min, re-equilibrate for 2.0 min;
Flow rate 1.0 ml/min; temperature 37° C.
5. HPLC System (Analytical)
VWR LaChrom Elite
HPLC—Method I
Column: VWR Chromolith SpeedRod RP-18e, 3.5 um, 4.6×50 mm;
Eluent: Water (+0.1% formic acid):acetonitrile (0.08% formic acid) from 95:5 to 5:95 in 8.5 min, hold 95% B for 1.5 min, re-equilibrate for 2.0 min;
Flow rate 1.0 ml/min; temperature 37° C.
HPLC—Method II
Column: VWR Chromolith SpeedRod RP-18e, 3.5 um, 4.6×50 mm;
Eluent: Water (+0.05% TFA):acetonitrile from 95:5 to 5:95 in 4.0 min, hold 95% B for 1.5 min, re-equilibrate for 0.5 min;
Flow rate 1.0 ml/min; temperature 37° C.
HPLC—Method III
Column: VWR Chromolith SpeedRod RP-18e, 3.5 um, 4.6×50 mm;
Eluent: Water (+0.1% formic acid):acetonitrile (0.08% formic acid) from 95:5 to 5:95 in 3.5 min, hold 95% B for 1.5 min, re-equilibrate for 2.0 min;
Flow rate 1.0 ml/min; temperature 37° C.
General Method 1:

Scheme 1:

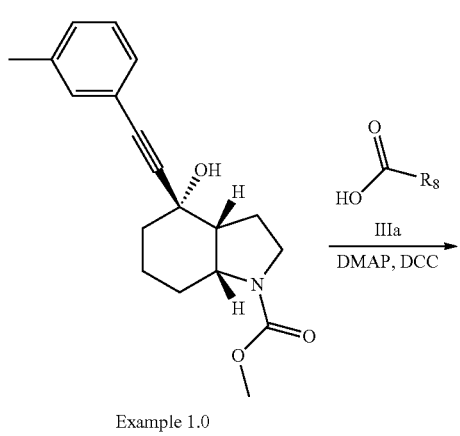

Example 1.0

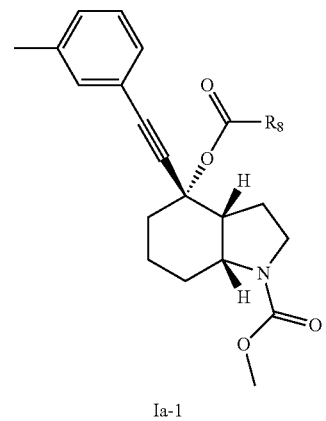

Ia-1

General Method 1 (an embodiment of Process 1) is illustrated using parent compound Example 1.0. A compound of formula IIa, in which $R_8$ is as defined under formula I (0.75 mol equiv.) and dicyclohexylcarbodiimide (DCC; 0.75 mol equiv.) is dissolved in dichloromethane (4 mL/mmol). Subsequently, 4-dimethylaminopyridine (DMAP; 0.5 mol equiv.) and 4-hydroxy-4-m-tolylethynyl-octahydro-indole-1-carboxylic acid methyl ester (Example 1.0; 0.5 mol equiv.) is added. The resulting suspension is stirred at room temperature (22° C.) for 18 h. The precipitation is removed by filtration and the clear filtrate is subjected to silica gel flash chromatography (ISCO CombiFlash) using the appropriate eluent (e.g. heptan/ethyl acetate; 90/10 to 50/50).

In an alternative General Method 1, compounds of formula IIIa may further contain N- or O-protecting groups which can be cleaved in an additional step to yield compounds of formula Ia-1.

EXAMPLE 1

(3aR,4S,7aR)-4-(2-Dimethylamino-acetoxy)-4-m-tolylethynyl-octahydro-indole-1-carboxylic acid methyl ester

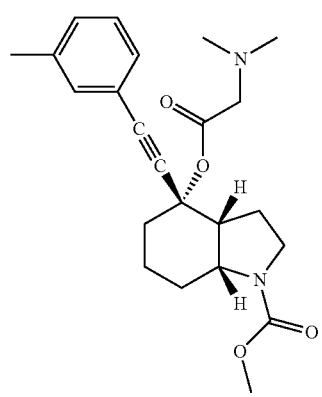 [SMILES: COC(=O)N1CC[C@@H]2[C@H]1CCC[C@]2(C#Cc1cccc(C)c1)OC(=O)CN(C)C]

Synthesis in analogy to the General Method 1 starting from (3aS,4R,7aS)-4-hydroxy-4-m-tolylethynyl-octahydro-indole-1-carboxylic acid methyl ester and dimethylamino acetic acid to yield (3aR,4S,7aR)-4-(2-dimethylamino-acetoxy)-4-m-tolylethynyl-octahydro-indole-1-carboxylic acid methyl ester. MS [M+H] 296 (ester elimination ion); Rt 4.592 min; LC-MS Method II

EXAMPLE 2

(3aR,4S,7aR)-4-(3-Dimethylamino-propionyloxy)-4-m-tolylethynyl-octahydro-indole-1-carboxylic acid methyl ester

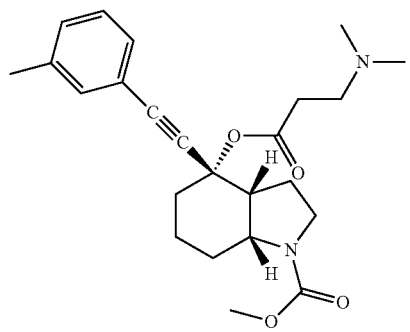

Synthesis in analogy to the General Method 1 starting from (3aS,4R,7aS)-4-hydroxy-4-m-tolylethynyl-octahydro-indole-1-carboxylic acid methyl ester and 3-dimethylamino propionic acid to yield (3aR,4S,7aR)-4-(3-dimethylamino-propionyloxy)-4-m-tolylethynyl-octahydro-indole-1-carboxylic acid methyl ester. MS [M+H] 413; RT 4.968 min; LC-MS Method ii

EXAMPLE 3

(3aR,4S,7aR)-4-(4-Dimethylamino-butyryloxy)-4-m-tolylethynyl-octahydro-indole-1-carboxylic acid methyl ester

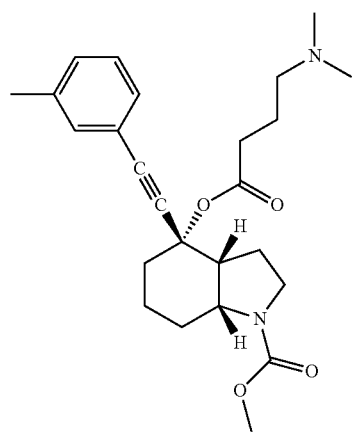

Synthesis in analogy to the General Method 1 starting from (3aS,4R,7aS)-4-hydroxy-4-m-tolylethynyl-octahydro-indole-1-carboxylic acid methyl ester and 4-dimethylamino butyric acid to yield (3aR,4S,7aR)-4-(4-dimethylamino-butyryloxy)-4-m-tolylethynyl-octahydro-indole-1-carboxylic acid methyl ester. MS [M+H] 427; RT 5.026 min; LC-MS Method II

EXAMPLE 4

(3aR,4S,7aR)-4-((S,R)-2-Amino-3-methyl-butyryloxy)-4-m-tolylethynyl-octahydro-indole-1-carboxylic acid methyl ester

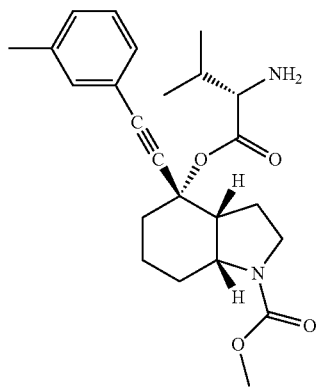 [SMILES: COC(=O)N1CC[C@@H]2[C@H]1CCC[C@]2(C#Cc1cccc(C)c1)OC(=O)[C@@H](N)C(C)C]

Synthesis in analogy to the General Method 1 starting from (3aS,4R,7aS)-4-hydroxy-4-m-tolylethynyl-octahydro-indole-1-carboxylic acid methyl ester and NBoc-valine to yield (3aR,4S,7aR)-4-((S,R)-2-tert-butoxycarbnylamino-3-methyl-butyryloxy)-4-m-tolylethynyl-octahydro-indole-1-carboxylic acid methyl ester. This NBoc-protected product was stirred in hydrochloric acid dioxane solution (4M, 10 equiv.) at room temperature for 6 hrs, Subsequently the solvent was removed to yield (3aR,4S,7aR)-4-((S,R)-2-amino-3-methyl-butyryloxy)-4-m-tolylethynyl-octahydro-indole-1-carboxylic acid methyl ester. MS [M+H] 296 (ester elimination ion); HPLC double peaks with RT=4.383/4.555 min; LC-MS Method IV

EXAMPLE 5

(3aR,4S,7aR)-4-((S)-2-Amino-4-methyl-pentanoyloxy)-4-m-tolylethynyl-octahydro-indole-1-carboxylic acid methyl ester

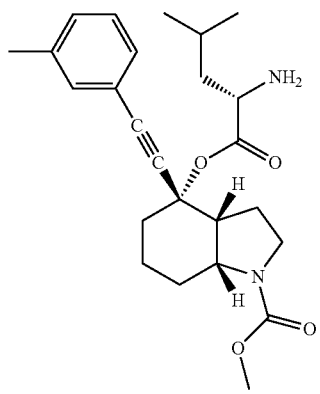 [SMILES: COC(=O)N1CC[C@@H]2[C@H]1CCC[C@]2(C#Cc1cccc(C)c1)OC(=O)[C@@H](N)CC(C)C]

Synthesis in analogy to the General Method 1 starting from (3aS,4R,7aS)-4-hydroxy-4-m-tolylethynyl-octahydro-indole-1-carboxylic acid methyl ester and NBoc-(S)-leucine to yield (3aR,4S,7aR)-4-((S)-2-tert-butoxycarbonylamino-4-methyl-pentanoyloxy)-4-m-tolylethynyl-octahydro-indole-1-carboxylic acid methyl ester. This NBoc-protected product was stirred in hydrochloric acid dioxane solution (4M, 10 equiv.) at room temperature for 6 hrs.

Subsequently the solvent was removed to yield (3aR,4S,7aR)-4-((S)-2-amino-4-methyl-pentanoyloxy)-4-m-tolylethynyl-octahydro-indole-1-carboxylic acid methyl ester. MS [M+H]427; RT 5.023 min; HPLC Method I

EXAMPLE 6

(3aR,4S,7aR)-4-((S)-2-Amino-4-methylsulfanyl-butyryloxy)-4-m-tolylethynyl-octahydro-indole-1-carboxylic acid methyl ester

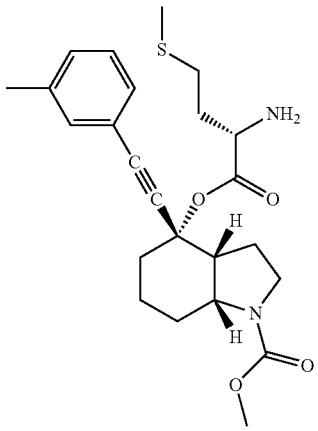 [SMILES: COC(=O)N1CC[C@@H]2[C@H]1CCC[C@]2(C#Cc1cccc(C)c1)OC(=O)[C@@H](N)CCSC]

Synthesis in analogy to the General Method 1 starting from (3aS,4R,7aS)-4-hydroxy-4-m-tolylethynyl-octahydro-indole-1-carboxylic acid methyl ester and NBoc-(S)-methionine to yield (3aR,4S,7aR)-4-((S)-2-tert-butoxycarbonylamino-4-methylsulfanyl-butyryloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((S)-2-amino-4-methylsulfanyl-butyryloxy)-4-m-tolylethynyl-octahydro-indole-1-carboxylic acid methyl ester. MS [M+H] 445; RT 4.883 min; HPLC Method I

EXAMPLE 7

(3aR,4S,7aR)-4-(2-Methylamino-acetoxy)-4-m-tolylethynyl-octahydro-indole-1-carboxylic acid methyl ester

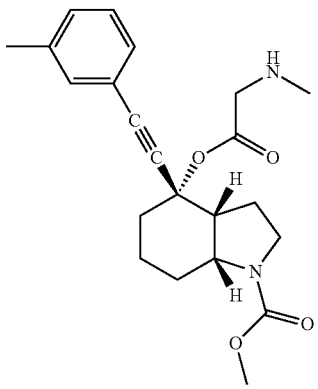

Synthesis in analogy to the General Method 1 starting from (3aS,4R,7aS)-4-hydroxy-4-m-tolylethynyl-octahydro-indole-1-carboxylic acid methyl ester and NBoc-sarcosine to yield (3aR,4S,7aR)-4-[2-(tert-butoxycarbonyl-methyl-amino)-acetoxy]-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-(2-methylamino-acetoxy)-4-m-tolylethynyl-octahydro-indole-1-carboxylic acid methyl ester. MS [M+H] 385; RT=4.510 min; HPLC Method I

EXAMPLE 8

(3aR,4S,7aR)-4-(2-Amino-acetoxy)-4-m-tolylethynyl-octahydro-indole-1-carboxylic acid methyl ester

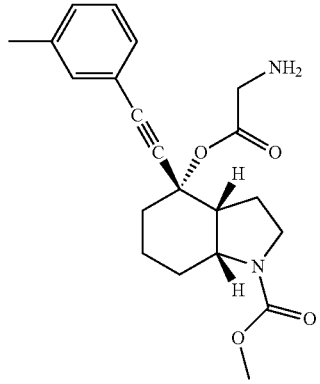 [SMILES: COC(=O)N1CC[C@@H]2[C@H]1CCC[C@]2(C#Cc1cccc(C)c1)OC(=O)CN]

Synthesis in analogy to the General Method 1 starting from (3aS,4R,7aS)-4-hydroxy-4-m-tolylethynyl-octahydro-indole-1-carboxylic acid methyl ester and NBoc-glycine to yield (3aR,4S,7aR)-4-(2-tert-butoxycarbonylamino-acetoxy)-4-m-tolylethynyl-octahydro-indole-1-carboxylic acid methyl ester. This NBoc-protected product was then stirred in hydrochloric acid dioxane solution (4M, mol 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-(2-amino-acetoxy)-4-m-tolylethynyl-octahydro-indole-1-carboxylic acid methyl ester. MS [M–H] 369; RT=4.470 min; HPLC Method I

EXAMPLE 9

(3aR,4S,7aR)-4-((S)-2-Amino-propionyloxy)-4-m-tolylethynyl-octahydro-indole-1-carboxylic acid methyl ester

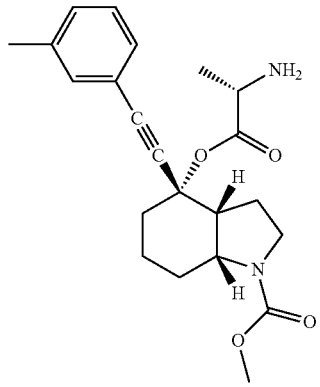 [SMILES: COC(=O)N1CC[C@@H]2[C@H]1CCC[C@]2(C#Cc1cccc(C)c1)OC(=O)[C@H](C)N]

NBoc-(S)-alanine (237 mg, 1.25 mmol) and dicyclohexylcarbodiimide (309 mg, 1.50 mmol) were dissolved in dichloromethane (4 mL). Subsequently, 4-dimethylaminopyridine (122 mg, 1.0 mmol) and (3aS,4R,7aS)-4-hydroxy-4-m-tolylethynyl-octahydro-indole-1-carboxylic acid methyl ester (313 mg, 1 mmol) were added. The resulting suspension was stirred at room temperature (22° C.) for 18 h. The precipitation was then removed by filtration and the clear filtrate was subjected to silica gel flash chromatography (ISCO CombiFlash Rf; 40 g silica gold, A=heptane, B=ethylacetate; A:B 100:0 to 0:100 in 20 min) and the solvent was evaporated to yield (3aR,4S,7aR)-4-((S)-2-tert-butoxycarbonylamino-propionyloxy)-4-m-tolylethynyl-octahydro-indole-1-carboxylic acid methyl ester (312 mg, 0.58 mmol, 58% yield). RT=6.772 (LC/MS Method II). This NBoc-protected product was then stirred in 4M-hydrochloric acid dioxane solution (1.45 mL, 5.8 mmol) at room temperature for 6 hrs. Subsequently the solvent was removed, the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash Rf; 40 g silica gel; dichloromethane/methanol; 100:0 to 95:5 in 18 min) and the solvents were evaporated to yield (3aR,4S,7aR)-4-((S)-2-amino-propionyloxy)-4-m-tolylethynyl-octahydro-indole-1-carboxylic acid methyl ester (144 mg, 0.38 mmol, 65% yield). MS [M−H]=383; RT=4.547 min (HPLC Method I). $^1$H-NMR (600 MHz; DMSO-d) δ ppm 1.20 (d, 3H), 1.21 (broad s, 1H), 1.55 to 2.12 (m, 7H), 2.30 (s, 3H), 3.17 (m, 1H), 3.35 (m, 2H), 3.44 (m, 1H), 3.57 (s, 3H), 3.88 (m, 1H), 7.23 (m, 2H) and 7.28 (m, 2H).

EXAMPLE 10

(3aR,4S,7aR)-4-(2-Methoxy-acetoxy)-4-m-tolylethynyl-octahydro-indole-1-carboxylic acid methyl ester

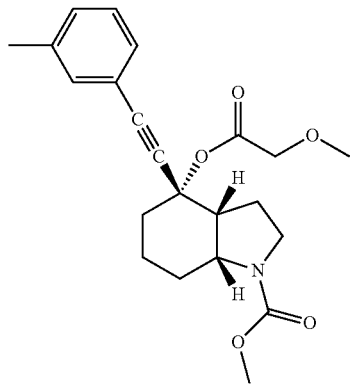

Synthesis in analogy to the General Method 1 starting from (3aS,4R,7aS)-4-hydroxy-4-m-tolylethynyl-octahydro-indole-1-carboxylic acid methyl ester and methoxy-acetic acid to yield (3aR,4S,7aR)-4-(2-methoxy-acetoxy)-4-m-tolylethynyl-octahydro-indole-1-carboxylic acid methyl ester. MS [M+H] 296 (ester elimination ion); RT=7.930 min; HPLC Method I

EXAMPLE 11

(3aR,4S,7aR)-4-[2-(2-Methoxy-ethoxy)-acetoxy]-4-m-tolylethynyl-octahydro-indole-1-carboxylic acid methyl ester

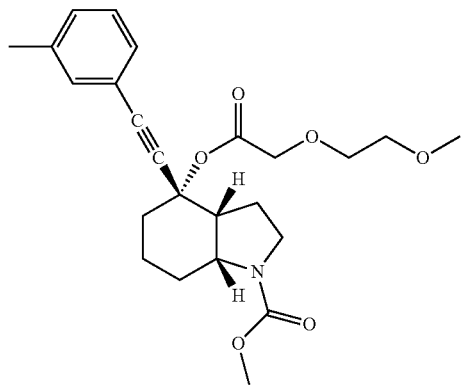

Synthesis in analogy to the General Method 1 starting from (3aS,4R,7aS)-4-hydroxy-4-m-tolylethynyl-octahydro-indole-1-carboxylic acid methyl ester and (2-methoxy-ethoxy)-acetic acid to yield (3aR,4S,7aR)-4-[2-(2-methoxy-ethoxy)-acetoxy]-4-m-tolylethynyl-octahydro-indole-1-carboxylic acid methyl ester. MS [M+H] 430; RT=7.850 min; HPLC Method I

EXAMPLE 12

(3aR,4S,7aR)-4-{2-[2-(2-Methoxy-ethoxy)-ethoxy]-acetoxy}-4-m-tolylethynyl-octahydro-indole-1-carboxylic acid methyl ester

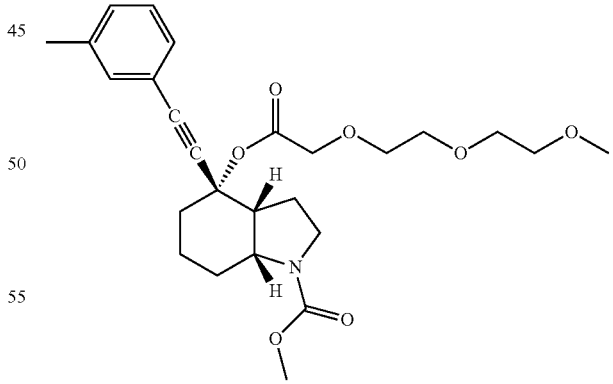

Synthesis in analogy to the General Method 1 starting from (3aS,4R,7aS)-4-hydroxy-4-m-tolylethynyl-octahydro-indole-1-carboxylic acid methyl ester and [2-(2-methoxy-ethoxy)-ethoxy]-acetic acid to yield (3aR,4S,7aR)-4-{2-[2-(2-methoxy-ethoxy)-ethoxy]-acetoxy}-4-m-tolylethynyl-octahydro-indole-1-carboxylic acid methyl ester. MS [M+H] 474; RT=7.747 min; HPLC Method I

EXAMPLE 13

(3aR,4S,7aR)-4-Acetoxy-4-m-tolylethynyl-octahydro-indole-1-carboxylic acid methyl ester

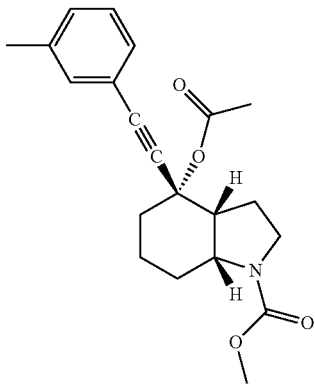 [SMILES: COC(=O)N1CC[C@@H]2[C@H]1CCC[C@]2(C#Cc1cccc(C)c1)OC(C)=O]

Synthesis in analogy to the General Method 1 starting from (3aS,4R,7aS)-4-hydroxy-4-m-tolylethynyl-octahydro-indole-1-carboxylic acid methyl ester and acetic acid to yield (3aR,4S,7aR)-4-acetoxy-4-m-tolylethynyl-octahydro-indole-1-carboxylic acid methyl ester. MS [M+H] 296 (ester elimination ion); =6.041 min; LC-MS Method II

EXAMPLE 14

(3aR,4S,7aR)-4-Propionyloxy-4-m-tolylethynyl-octahydro-indole-1-carboxylic acid methyl ester

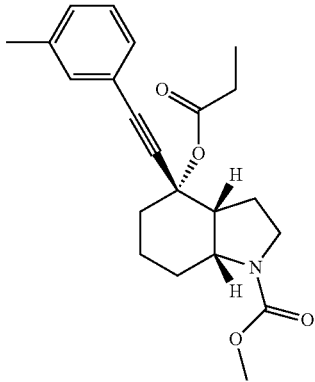 [SMILES: CCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and propionic acid to yield (3aR,4S,7aR)-4-propionyloxy-4-m-tolylethynyl-octahydro-indole-1-carboxylic acid methyl ester. MS [M+H] 296 (ester elimination ion); RT=1.34 min; UPLC Method I

EXAMPLE 15

(3aR,4S,7aR)-4-Butyryloxy-4-m-tolylethynyl-octahydro-indole-1-carboxylic acid methyl ester

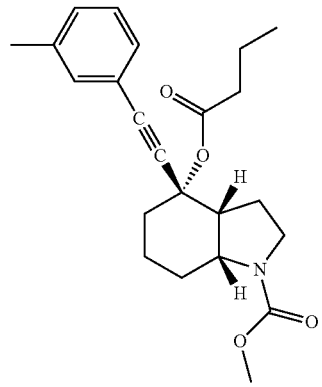 [SMILES: CCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and butyric acid to yield (3aR,4S,7aR)-4-butyryloxy-4-m-tolylethynyl-octahydro-indole-1-carboxylic acid methyl ester. MS [M+H] 296 (ester elimination ion); RT=1.40 min; UPLC Method I

EXAMPLE 16

(3aR,4S,7aR)-4-Tetradecanoyloxy-4-m-tolylethynyl-octahydro-indole-1-carboxylic acid methyl ester

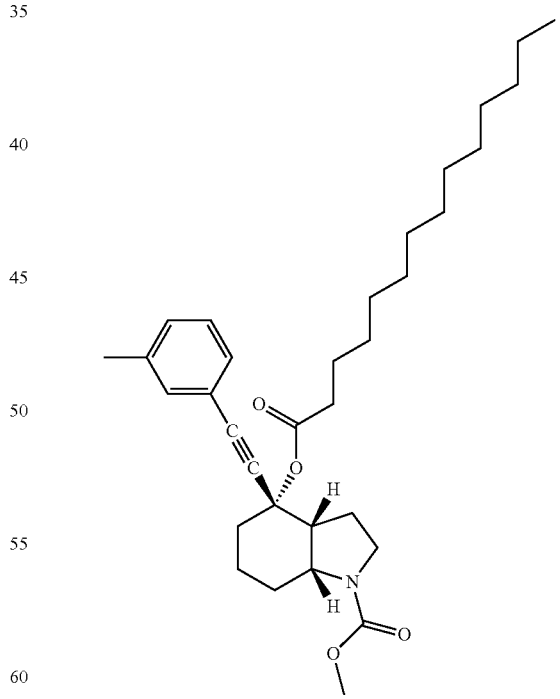

Synthesis in analogy to the General Method 1 starting from (3aS,4R,7aS)-4-hydroxy-4-m-tolylethynyl-octahydro-indole-1-carboxylic acid methyl ester and tetradecanoic acid to yield (3aR,4S,7aR)-4-tetradecanoyloxy-4-m-tolylethynyl-octahydro-indole-1-carboxylic acid methyl ester. MS [M+H] 296 (ester elimination ion); RT=2.01 min; UPLC Method I

EXAMPLE 17

(3aR,4S,7aR)-4-Hexanoyloxy-4-m-tolylethynyl-octahydro-indole-1-carboxylic acid methyl ester

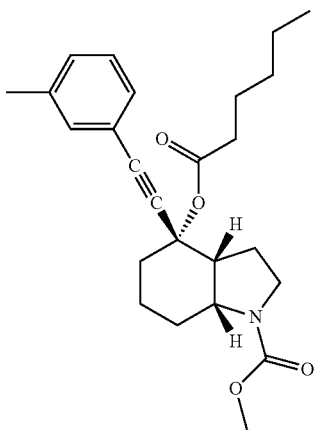 [SMILES: CCCCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and hexanoic acid to yield (3aR,4S,7aR)-4-hexanoyloxy-4-m-tolylethynyl-octahydro-indole-1-carboxylic acid methyl ester. MS [M+H] 296 (ester elimination ion); RT=1.53 min; UPLC Method I

EXAMPLE 18

3aR,4S,7aR)-4-Octanoyloxy-4-m-tolylethynyl-octahydro-indole-1-carboxylic acid methyl ester

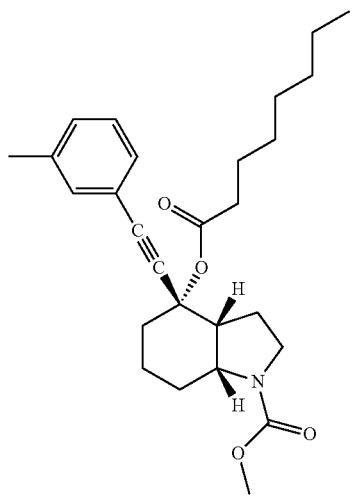 [SMILES: CCCCCCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and octanoic acid to yield (3aR,4S,7aR)-4-octanoyloxy-4-m-tolylethynyl-octahydro-indole-1-carboxylic acid methyl ester. MS [M+H] 296 (ester elimination ion); RT=1.60 min; UPLC Method I

EXAMPLE 19

(3aR,4S,7aR)-4-Dodecanoyloxy-4-m-tolylethynyl-octahydro-indole-1-carboxylic acid methyl ester

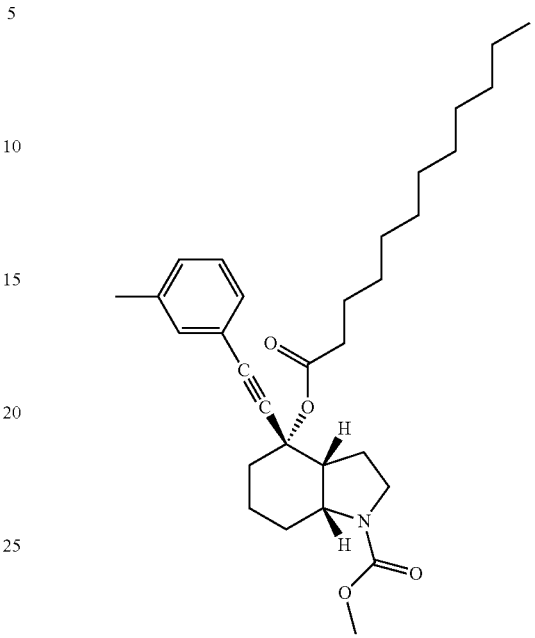

Synthesis in analogy to the General Method 1 starting from (3aS,4R,7aS)-4-hydroxy-4-m-tolylethynyl-octahydro-indole-1-carboxylic acid methyl ester and dodecanoic acid to yield (3aR,4S,7aR)-4-dodecanoyloxy-4-m-tolylethynyl-octahydro-indole-1-carboxylic acid methyl ester. MS [M+H] 296 (ester elimination ion); RT=1.80 min; UPLC Method I

EXAMPLE 20

(3aR,4S,7aR)-4-Decanoyloxy-4-m-tolylethynyl-octahydro-indole-1-carboxylic acid methyl ester

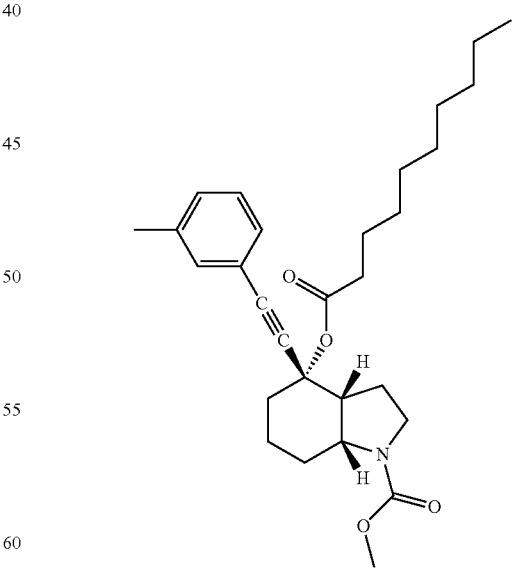

Synthesis in analogy to the General Method 1 starting from (3aS,4R,7aS)-4-hydroxy-4-m-tolylethynyl-octahydro-indole-1-carboxylic acid methyl ester and decanoic acid to yield (3aR,4S,7aR)-4-decanoyloxy-4-m-tolylethynyl-octahydro-indole-1-carboxylic acid methyl ester. MS [M+H] 296 (ester elimination ion); RT1.70 min; UPLC Method I

EXAMPLE 21

(3aR,4S,7aR)-4-(Dimethoxy-phosphanyloxy)-4-m-tolylethynyl-octahydro-ndole-1-carboxylic acid methyl ester

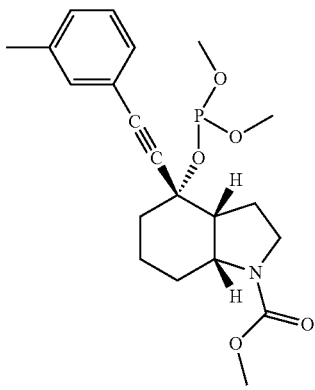 [SMILES: COC(=O)N1CC[C@@H]2[C@H]1CCC[C@]2(C#Cc1cccc(C)c1)OP(OC)OC]

(3aS,4R,7aS)-4-hydroxy-4-m-tolylethynyl-octahydro-indole-1-carboxylic acid methyl ester (1 mol equiv) and dimethyl diisopropyl phosphoramidite (1.5 mol equiv) in tetrazole (3 mol equiv.) and methylenechloride were stirred at room temperature for 1 hour. The crude product was subjected to silica gel flash chromatography (ISCO CombiFlash; hexane/ethyl acetate; gradient 80/20 to 30/70) to yield (3aR,4S,7aR)-4-(dimethoxy-phosphanyloxy)-4-m-tolylethynyl-octahydro-indole-1-carboxylic acid methyl ester. MS [M+H] 406; RT=1.02 min; UPLC Method I

EXAMPLE 22

(3aR,4S,7aR)-4-Pentanoyloxy-4-m-tolylethynyl-octahydro-indole-1-carboxylic acid methyl ester

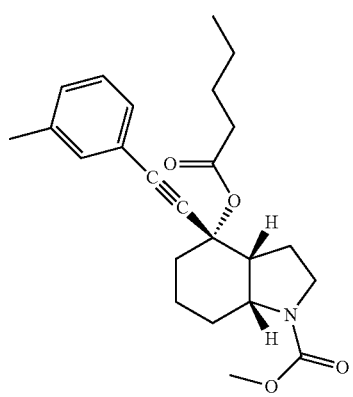 [SMILES: CCCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and pentanoic acid to yield (3aR,4S,7aR)-4-pentanoyloxy-4-m-tolylethynyl-octahydro-indole-1-carboxylic acid methyl ester. MS [M+Na]= 420; RT=8.337 min; LC-MS Method III

EXAMPLE 23

(3aR,4S,7aR)-4-Heptanoyloxy-4-m-tolylethynyl-octahydro-indole-1-carboxylic acid methyl ester

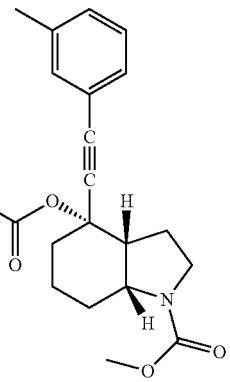

Synthesis in analogy to the General Method 1 starting from (3aS,4R,7aS)-4-hydroxy-4-m-tolylethynyl-octahydro-indole-1-carboxylic acid methyl ester and heptanoic acid to yield (3aR,4S,7aR)-4-heptanoyloxy-4-m-tolylethynyl-octahydro-indole-1-carboxylic acid methyl ester. MS [M+Na]= 448; RT=9.098 min; LC-MS Method III

EXAMPLE 24

(3aR,4S,7aR)-4-Nonanoyloxy-4-m-tolylethynyl-octahydro-indole-1-carboxylic acid methyl ester

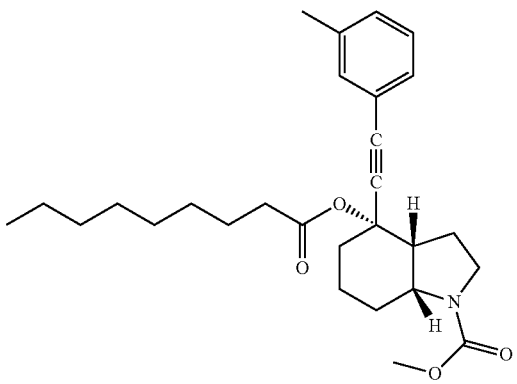 [SMILES: CCCCCCCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and nonanoic acid to yield (3aR,4S,7aR)-4-nonanoyloxy-4-m-tolylethynyl-octahydro-indole-1-carboxylic acid methyl ester. MS [M+Na]= 476; RT 9.818 min; LC-MS Method III

EXAMPLE 25

(3aR,4S,7aR)-4-m-Tolylethynyl-4-tridecanoyloxy-octahydro-indole-1-carboxylic acid methyl ester

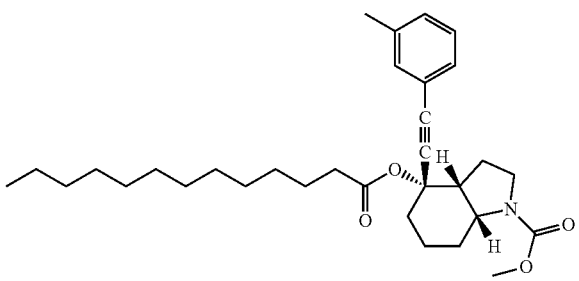 [SMILES: CCCCCCCCCCCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and tridecanoic acid to yield (3aR,4S,7aR)-4-m-tolylethynyl-4-tridecanoyloxy-octahydro-indole-1-carboxylic acid methyl ester. MS [M+Na]=532; RT=7.113 min; LC-MS Method V

EXAMPLE 26

(3aR,4S,7aR)-4-(2-Morpholin-4-yl-acetoxy)-4-m-tolylethynyl-octahydro-indole-1-carboxylic acid methyl ester

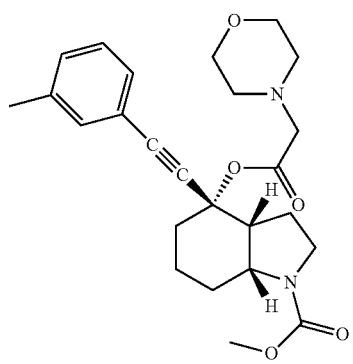 [SMILES: COC(=O)N1CC[C@@H]2[C@H]1CCC[C@]2(C#Cc1cccc(C)c1)OC(=O)CN1CCOCC1]

Synthesis in analogy to the General Method 1 starting from (3aS,4R,7aS)-4-hydroxy-4-m-tolylethynyl-octahydro-indole-1-carboxylic acid methyl ester and morpholin-4-yl-acetic acid to yield (3aR,4S,7aR)-4-(2-morpholin-4-yl-acetoxy)-4-m-tolylethynyl-octahydro-indole-1-carboxylic acid methyl ester. MS [M+H]=296 (ester elimination ion); RT=6.574 min; LC-MS Method III

EXAMPLE 27

(3aR,4S,7aR)-4-(3-Morpholin-4-yl-propionyloxy)-4-m-tolylethynyl-octahydro-indole-1-carboxylic acid methyl ester

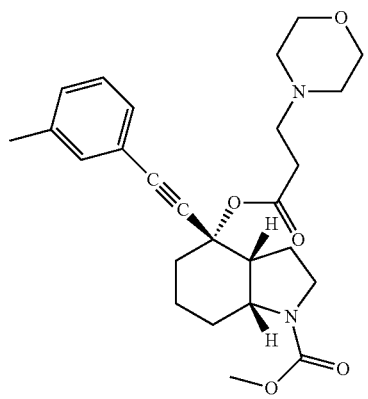 [SMILES: COC(=O)N1CC[C@@H]2[C@H]1CCC[C@]2(C#Cc1cccc(C)c1)OC(=O)CCN1CCOCC1]

Synthesis in analogy to the General Method 1 starting from (3aS,4R,7aS)-4-hydroxy-4-m-tolylethynyl-octahydro-indole-1-carboxylic acid methyl ester and 3-morpholin-4-yl-propionic acid to yield (3aR,4S,7aR)-4-(3-morpholin-4-yl-propionyloxy)-4-m-tolylethynyl-octahydro-indole-1-carboxylic acid methyl ester. MS [M+H]=296 (ester elimination ion); RT=4.088 min; LC-MS Method III

EXAMPLE 28

(3aR,4S,7aR)-4-(2-Imidazol-1-yl-acetoxy)-4-m-tolylethynyl-octahydro-indole-1-carboxylic acid methyl ester

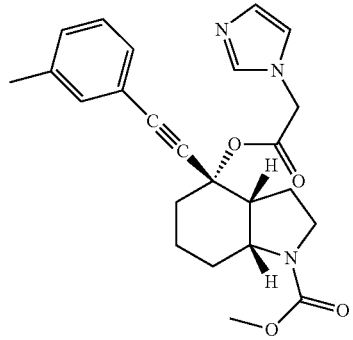 [SMILES: COC(=O)N1CC[C@@H]2[C@H]1CCC[C@]2(C#Cc1cccc(C)c1)OC(=O)Cn1ccnc1]

Synthesis in analogy to the General Method 1 starting from (3aS,4R,7aS)-4-hydroxy-4-m-tolylethynyl-octahydro-indole-1-carboxylic acid methyl ester and 2-(1H-imidazol-1-yl)acetic acid to yield (3aR,4S,7aR)-4-(2-imidazol-1-yl-acetoxy)-4-m-tolylethynyl-octahydro-indole-1-carboxylic acid methyl ester. MS [M+H]=422; RT=5.152 min; LC-MS Method III

EXAMPLE 29

(3aR,4S,7aR)-4-(3-Pyrrolidin-1-yl-propionyloxy)-4-m-tolylethynyl-octahydro-indole-1-carboxylic acid methyl ester

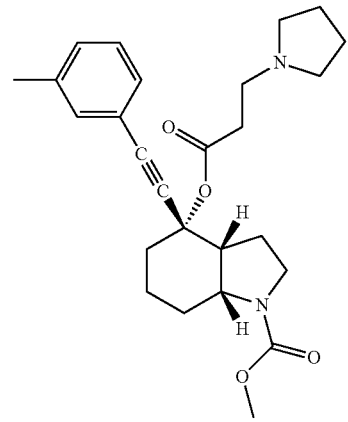 [SMILES: COC(=O)N1CC[C@@H]2[C@H]1CCC[C@]2(C#Cc1cccc(C)c1)OC(=O)CCN1CCCC1]

3-Pyrrolidin-1-yl-propionic acid (143 mg, 1.0 mmol) and dicyclohexylcarbodiimide (247 mg, 1.2 mmol) were dissolved in dichloromethane (5 mL). Subsequently, 4-dimethylaminopyridine (97 mg, 0.8 mmol) and (3aS,4R,7aS)-4-hydroxy-4-m-tolylethynyl-octahydro-indole-1-carboxylic acid methyl ester (250 mg, 0.8 mmol) were added. The resulting suspension was stirred at room temperature (22° C.) for 50 h. The precipitation was then removed by filtration and the clear filtrate was subjected to silica gel flash chromatography [ISCO CombiFlash Companion; 40 g silica gel; methylenechloride/methanol; methanol 0% (4 min), 1% (4 min), 2% (4 min), 2-5% (2 min), 5% (5 min) and 10% (8 min)]. Then, the solvents were evaporated to yield (3aR,4S,7aR)-4-(3-pyrrolidin-1-yl-propionyloxy)-4-m-tolylethynyl-octahydro-indole-1-carboxylic acid methyl ester (123 mg, 0.28 mmol, 35% yield). MS [M+H]=439; RT=6.122 min (LC-MS Method III). $^1$H-NMR (600 MHz; DMSO-d$^6$) δ ppm 1.23 (m, 1H), 1.65 (broad s, 4H), 1.80 to 2.10 (m, 5H), 2.30 (s, 3H), 2.46 (m, 4H), 2.49 (m, 4H), 2.67 (m, 2H), 3.13 (m, 1H), 3.30 (m, 1H), 3.42 (q, 1H), 3.55 (s, 3H), 3.88 (m, 1H), 7.22 (broad s, 2H) and 7.27 (m, 2H).

EXAMPLE 30

(3aR,4S,7aR)-4-((S)-2-Amino-butyryloxy)-4-m-tolylethynyl-octahydro-indole-1-carboxylic acid methyl ester

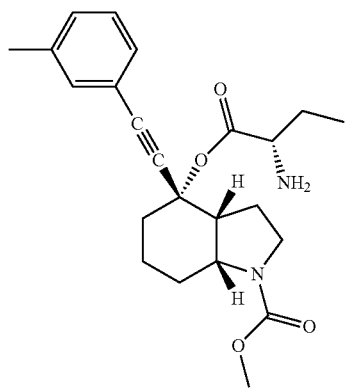 [SMILES: CC[C@H](N)C(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and N Boc-(S)-2-aminobutyric acid to yield (3aR,4S,7aR)-4-((S)-2-tert-butoxycarbonylamino-butyryloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((S)-2-amino-butyryloxy)-4-m-tolylethynyl-octahydro-indole-1-carboxylic acid methyl ester. RT=3.973 min; HPLC Method I

EXAMPLE 31

(3aR,4S,7aR)-4-((S)-2-Amino-3-phenyl-propionyloxy)-4-m-tolylethynyl-octahydro-indole-1-carboxylic acid methyl ester

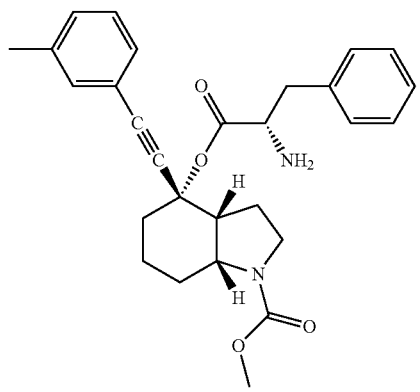 [SMILES: COC(=O)N1CC[C@@H]2[C@H]1CCC[C@]2(C#Cc1cccc(C)c1)OC(=O)[C@@H](N)Cc1ccccc1]

Synthesis in analogy to the General Method 1 starting from (3aS,4R,7aS)-4-hydroxy-4-m-tolylethynyl-octahydro-indole-1-carboxylic acid methyl ester and NBoc-(S)-phenylalanine to yield (3aR,4S,7aR)-4-((S)-2-tert-butoxycarbonylamino-3-phenyl-propionyloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((S)-2-amino-3-phenyl-propionyloxy)-4-m-tolylethynyl-octahydro-indole-1-carboxylic acid methyl ester. RT=4.400 min; HPLC Method I

EXAMPLE 32

(3aR,4S,7aR)-4-((S)-2-Amino-pentanoyloxy)-4-m-tolylethynyl-octahydro-indole-1-carboxylic acid methyl ester

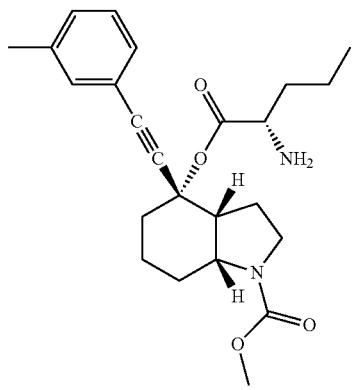 [SMILES: CCC[C@H](N)C(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and NBoc-(S)-2-aminopentanoic acid to yield (3aR,4S,7aR)-4-((S)-2-tert-butoxycarbonylamino-pentanoyloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield ((3aR,4S,7aR)-4-((S)-2-amino-pentanoyloxy)-4-m-tolylethynyl-octahydro-indole-1-carboxylic acid methyl ester. RT=4.197 min; HPLC Method I

EXAMPLE 33

(3aR,4S,7aR)-4-((2S,3S)-2-Amino-3-methyl-pentanoyloxy)-4-m-tolylethynyl-octahydro-indole-1-carboxylic acid methyl ester

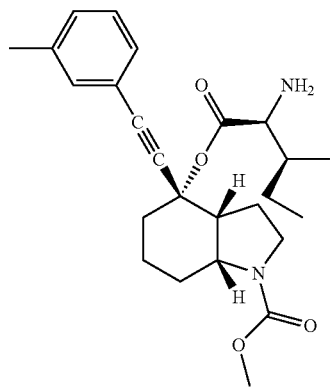 [SMILES: CC[C@H](C)[C@H](N)C(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and (2S,3S)-2-(tert-butoxycarbonylamino)-3-methylpentanoic acid to yield (3aR,4S,7aR)-4-((2S,3S)-2-tert-butoxycarbonylamino-3-methyl-pentanoyloxy)-4-m-tolylethynyl-octahydro-indole-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((2S,3S)-2-amino-3-methyl-pentanoyloxy)-4-m-tolylethynyl-octahydro-indole-1-carboxylic acid methyl ester. MS [M+H] 296 (ester elimination ion); RT=5.703 min; HPLC Method I

EXAMPLE 34

(3aR,4S,7aR)-4-((S)-2-Amino-4,4-dimethyl-pentanoyloxy)-4-m-tolylethynyl-octahydro-indole-1-carboxylic acid methyl ester

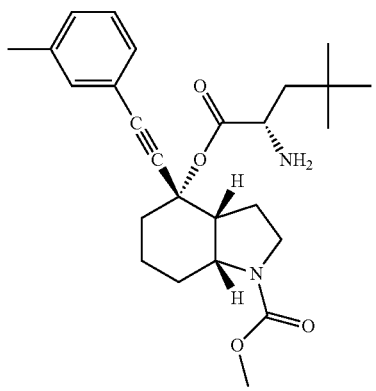 [SMILES: COC(=O)N1CC[C@@H]2[C@H]1CCC[C@]2(C#Cc1cccc(C)c1)OC(=O)[C@@H](N)CC(C)(C)C]

Synthesis in analogy to the General Method 1 starting from (3aS,4R,7aS)-4-hydroxy-4-m-tolylethynyl-octahydro-indole-1-carboxylic acid methyl ester and (S)-2-tert-butoxycarbonylamino-4,4-dimethyl-pentanoic acid to yield (3aR,4S,7aR)-4-((S)-2-tert-butoxycarbonylamino-4,4-dimethyl-pentanoyloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((S)-2-amino-4,4-dimethyl-pentanoyloxy)-4-m-tolylethynyl-octahydro-indole-1-carboxylic acid methyl ester. MS [M+H] 296 (ester elimination ion); RT=5.787 min; HPLC Method I

EXAMPLE 35

(3aR,4S,7aR)-4-((S)-2-Methylamino-propionyloxy)-4-m-tolylethynyl-octahydro-indole-1-carboxylic acid methyl ester

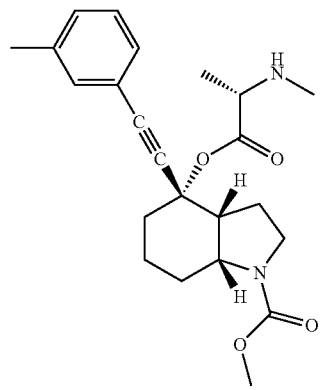

Synthesis in analogy to the General Method 1 starting from (3aS,4R,7aS)-4-hydroxy-4-m-tolylethynyl-octahydro-indole-1-carboxylic acid methyl ester and NBoc-(S)-2-methylamino-propionic acid to yield (3aR,4S,7aR)-4-[(S)-2-(tert-butoxycarbonyl-methyl-amino)-propionyloxy]-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((S)-2-methylamino-propionyloxy)-4-m-tolylethynyl-octahydro-indole-1-carboxylic acid methyl ester. MS [M+H] 296 (ester elimination ion); RT=7.658 min; HPLC Method I

EXAMPLE 36

(3aR,4S,7aR)-4-((S)-3-Methyl-2-methylamino-butyryloxy)-4-m-tolylethynyl-octahydro-indole-1-carboxylic acid methyl ester

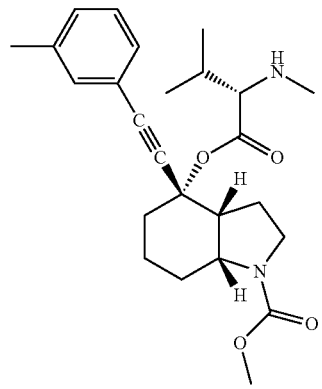

Synthesis in analogy to the General Method 1 starting from (3aS,4R,7aS)-4-hydroxy-4-m-tolylethynyl-octahydro-indole-1-carboxylic acid methyl ester and (S)-2-(tert-butoxycarbonyl-methyl-amino)-3-methyl-butyric acid to yield (3aR,4S,7aR)-4-[(S)-2-(tert-butoxycarbonyl-methyl-amino)-3-methyl-butyryloxy]-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((S)-3-methyl-2-methylamino-butyryloxy)-4-m-tolylethynyl-octahydro-indole-1-carboxylic acid methyl ester. MS [M+H]=296 (ester elimination ion); RT=5.490 min; HPLC Method I

EXAMPLE 37

(3aR,4S,7aR)-4-((2S,3S)-3-Methyl-2-methylamino-pentanoyloxy)-4-m-tolylethynyl-octahydro-indole-1-carboxylic acid methyl ester

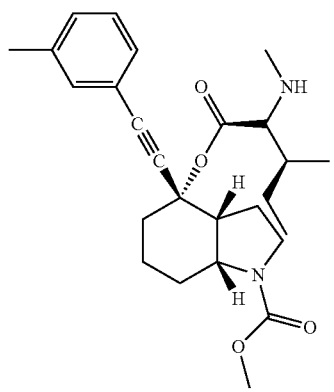

Synthesis in analogy to the General Method 1 starting from (3aS,4R,7aS)-4-hydroxy-4-m-tolylethynyl-octahydro-indole-1-carboxylic acid methyl ester and (2S,3S)-2-(tert-butoxycarbonyl-methyl-amino)-3-methyl-pentanoic acid to yield (3aR,4S,7aR)-4-[(2S,3S)-2-(tert-butoxycarbonyl-methyl-amino)-3-methyl-pentanoyloxy]-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((2S,3S)-3-methyl-2-methylamino-pentanoyloxy)-4-m-tolylethynyl-octahydro-indole-1-carboxylic acid methyl ester. MS [M+H] 296 (ester elimination ion); RT=5.213 min; HPLC Method I

EXAMPLE 38

(3aR,4S,7aR)-4-(4-Oxo-4-pyrrolidin-1-yl-butyryloxy)-4-m-tolylethynyl-octahydro-indole-1-carboxylic acid methyl ester

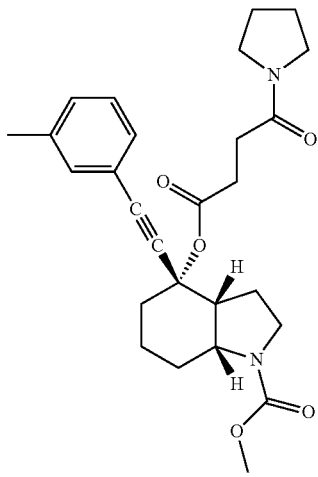 [SMILES: COC(=O)N1CC[C@@H]2[C@H]1CCC[C@]2(C#Cc1cccc(C)c1)OC(=O)CCC(=O)N1CCCC1]

Synthesis in analogy to the General Method 1 starting from (3aS,4R,7aS)-4-hydroxy-4-m-tolylethynyl-octahydro-indole-1-carboxylic acid methyl ester and 4-oxo-4-(pyrrolidin-1-yl)-butanoic acid to yield (3aR,4S,7aR)-4-(4-oxo-4-pyrrolidin-1-yl-butyryloxy)-4-m-tolylethynyl-octahydro-indole-1-carboxylic acid methyl ester. MS [M+H]=467; RT=2.88 min; UPLC Method II

EXAMPLE 39

(3aR,4S,7aR)-4-m-Tolylethynyl-4-undecanoyloxy-octahydro-indole-1-carboxylic acid methyl ester

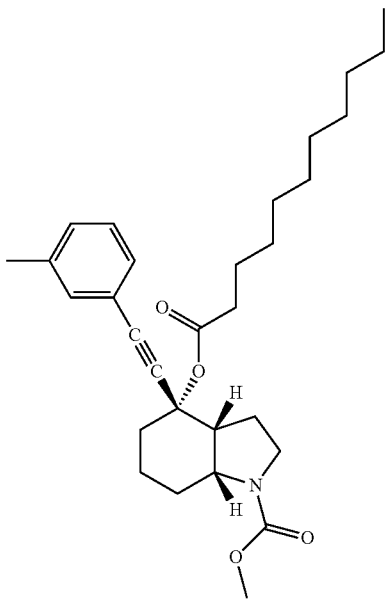 [SMILES: CCCCCCCCCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and undecanoic acid to yield (3aR,4S,7aR)-4-m-tolylethynyl-4-undecanoyloxy-octahydro-indole-1-carboxylic acid methyl ester. MS [M+H]= 296 (ester elimination ion); RT=1.77 min; UPLC Method I

EXAMPLE 40

(3aR,4S,7aR)-methyl 4-(3-aminopropanoyloxy)-4-(m-tolylethynyl)octahydro-1H-indole-1-carboxylate

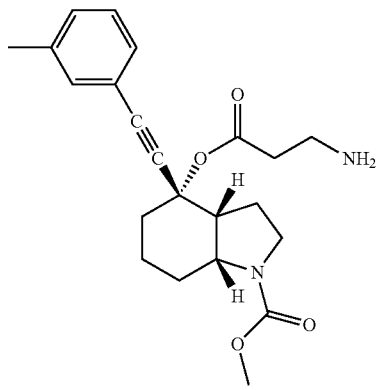 [SMILES: COC(=O)N1CC[C@@H]2[C@H]1CCC[C@]2(C#Cc1cccc(C)c1)OC(=O)CCN]

Synthesis in analogy to the General Method 1 starting from (3aS,4R,7aS)-4-hydroxy-4-m-tolylethynyl-octahydro-indole-1-carboxylic acid methyl ester and 3-tert-butoxycarbonylamino-propionic acid to yield (3aR,4S,7aR)-4-(3-tert-butoxycarbonylamino-propionyloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-methyl 4-(3-aminopropanoyloxy)-4-(m-tolylethynyl)octahydro-1H-indole-1-carboxylate. MS [M+Na]=407; RT=4.395 min; LC-MS Method II

EXAMPLE 41

(3aR,4S,7aR)-methyl 4-((S)-2-amino-2-phenylacetoxy)-4-(m-tolylethynyl)octahydro-1H-indole-1-carboxylate

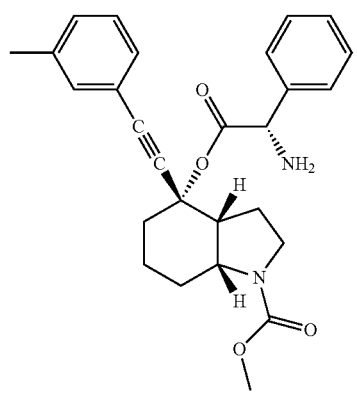 [SMILES: COC(=O)N1CC[C@@H]2[C@H]1CCC[C@]2(C#Cc1cccc(C)c1)OC(=O)[C@@H](N)c1ccccc1]

Synthesis in analogy to the General Method 1 starting from (3aS,4R,7aS)-4-hydroxy-4-m-tolylethynyl-octahydro-indole-1-carboxylic acid methyl ester and Nboc-(S)-phenylglycine to yield (3aR,4S,7aR)-4-((S)-2-tert-butoxycarbonylamino-2-phenyl-acetoxy)-4-m-tolyethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-methyl 4-((S)-2-amino-2-phenylacetoxy)-4-(m-tolylethynyl)octahydro-1H-indole-1-carboxylate. MS [M+H]=447; RT=5.698 min; LC-MS Method II

EXAMPLE 42

(3aR,4S,7aR)-methyl 4-(benzoyloxy)-4-(m-tolylethynyl)octahydro-1H-indole-1-carboxylate

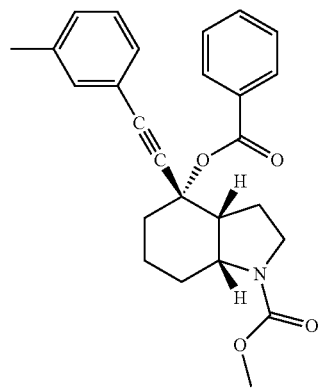 [SMILES: COC(=O)N1CC[C@@H]2[C@H]1CCC[C@]2(C#Cc1cccc(C)c1)OC(=O)c1ccccc1]

Synthesis in analogy to the General Method 1 starting from (3aS,4R,7aS)-4-hydroxy-4-m-tolylethynyl-octahydro-indole-1-carboxylic acid methyl ester and benzoic acid to yield (3aR,4S,7aR)-methyl 4-(benzoyloxy)-4-(m-tolylethynyl)octahydro-1H-indole-1-carboxylate. MS [M+H]=296 (ester elimination ion); RT=6.370 min; LC-MS Method II

EXAMPLE 43

(3aR,4S,7aR)-methyl 4-(2-phenylacetoxy)-4-(m-tolylethynyl)octahydro-1H-indole-1-carboxylate

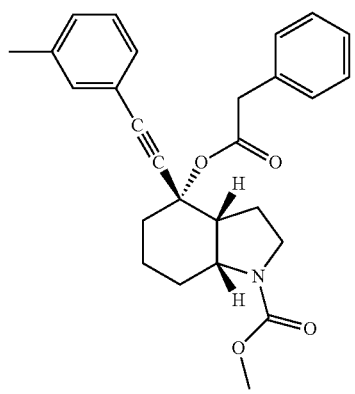 [SMILES: COC(=O)N1CC[C@@H]2[C@H]1CCC[C@]2(C#Cc1cccc(C)c1)OC(=O)Cc1ccccc1]

Synthesis in analogy to the General Method 1 starting from (3aS,4R,7aS)-4-hydroxy-4-m-tolylethynyl-octahydro-indole-1-carboxylic acid methyl ester and phenyl-acetic acid to yield (3aR,4S,7aR)-methyl 4-(2-phenylacetoxy)-4-(m-tolylethynyl)octahydro-1H-indole-1-carboxylate. MS [M+H]= 296 (ester elimination ion); RT=7.221 min; LC-MS Method II

EXAMPLE 44

(3aR,4S,7aR)-methyl 4-(3-phenylpropanoyloxy)-4-(m-tolylethynyl)octahydro-1H-indole-1-carboxylate

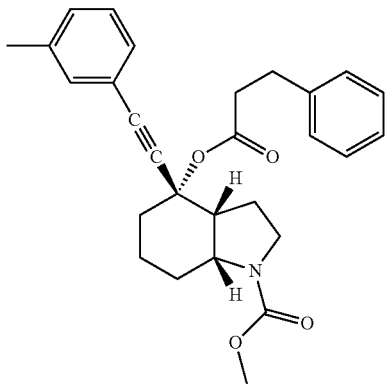 [SMILES: COC(=O)N1CC[C@@H]2[C@H]1CCC[C@]2(C#Cc1cccc(C)c1)OC(=O)CCc1ccccc1]

Synthesis in analogy to the General Method 1 starting from (3aS,4R,7aS)-4-hydroxy-4-m-tolylethynyl-octahydro-indole-1-carboxylic acid methyl ester and 3-phenyl-propionic acid to yield (3aR,4S,7aR)-methyl 4-(3-phenylpropanoyloxy)-4-(m-tolylethynyl)octahydro-1H-indole-1-carboxylate. MS [M+H]=296 (ester elimination ion); RT=7.957 min; LC-MS Method II

EXAMPLE 45

(3aR,4S,7aR)-methyl 4-(isonicotinoyloxy)-4-(m-tolylethynyl)octahydro-1H-indole-1-carboxylate

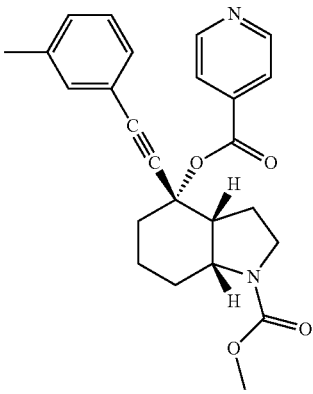 [SMILES: COC(=O)N1CC[C@@H]2[C@H]1CCC[C@]2(C#Cc1cccc(C)c1)OC(=O)c1ccncc1]

Synthesis in analogy to the General Method 1 starting from (3aS,4R,7aS)-4-hydroxy-4-m-tolylethynyl-octahydro-indole-1-carboxylic acid methyl ester and isonicotinic acid to yield (3aR,4S,7aR)-methyl 4-(isonicotinoyloxy)-4-(m-tolylethynyl)octahydro-1H-indole-1-carboxylate. MS [M+H]= 391; RT=6.510 min; LC-MS Method II

EXAMPLE 46

(3aR,4S,7aR)-methyl 4-(3-methylbenzoyloxy)-4-(m-tolylethynyl)octahydro-1H-indole-1-carboxylate

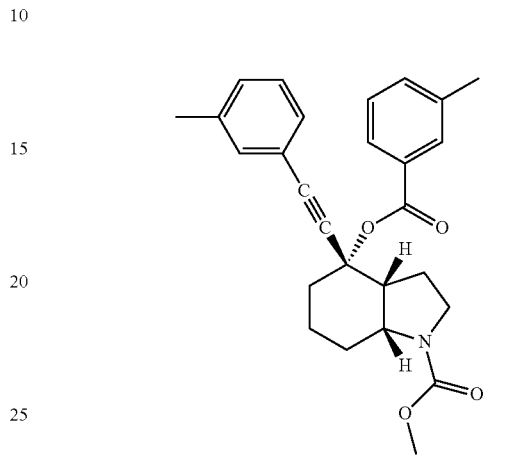

Synthesis in analogy to the General Method 1 starting from (3aS,4R,7aS)-4-hydroxy-4-m-tolylethynyl-octahydro-indole-1-carboxylic acid methyl ester and 3-methyl-benzoic acid to yield (3aR,4S,7aR)-methyl 4-(3-methylbenzoyloxy)-4-(m-tolylethynyl)octahydro-1H-indole-1-carboxylate. MS [M+H]=296 (ester elimination ion); RT=7.376 min; LC-MS Method II

EXAMPLE 47

(3aR,4S,7aR)-methyl 4-(3,5-dichlorobenzoyloxy)-4-(m-tolylethynyl)octahydro-1H-indole-1-carboxylate

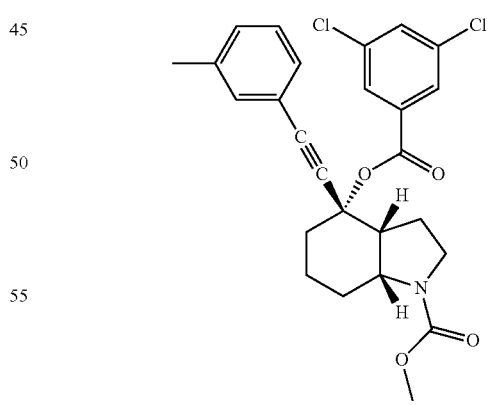

Synthesis in analogy to the General Method 1 starting from (3aS,4R,7aS)-4-hydroxy-4-m-tolylethynyl-octahydro-indole-1-carboxylic acid methyl ester and 3,5-dichloro-benzoic acid to yield (3aR,4S,7aR)-methyl 4-(3,5-dichlorobenzoyloxy)-4-(m-tolylethynyl)octahydro-1H-indole-1-carboxylate. MS [M+H]=296 (ester elimination ion); RT=8.825 min; LC-MS Method II

EXAMPLE 48

(3aR,4S,7aR)-methyl 4-(4-bromobenzoyloxy)-4-(m-tolylethynyl)octahydro-1H-indole-1-carboxylate

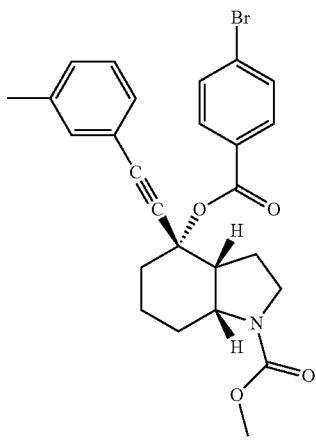 [SMILES: COC(=O)N1CC[C@@H]2[C@H]1CCC[C@]2(C#Cc1cccc(C)c1)OC(=O)c1ccc(Br)cc1]

Synthesis in analogy to the General Method 1 starting from (3aS,4R,7aS)-4-hydroxy-4-m-tolylethynyl-octahydro-indole-1-carboxylic acid methyl ester and 4-brom-benzoic acid to yield (3aR,4S,7aR)-methyl 4-(4-bromobenzoyloxy)-4-(m-tolylethynyl)octahydro-1H-indole-1-carboxylate. MS [M+H]=296 (ester elimination ion); RT=7.705 min; LC-MS Method II

EXAMPLE 49

(3aR,4S,7aR)-methyl 4-(cyclopentanecarbonyloxy)-4-(m-tolylethynyl)octahydro-1H-indole-1-carboxylate

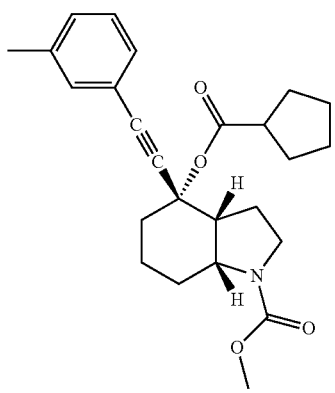 [SMILES: COC(=O)N1CC[C@@H]2[C@H]1CCC[C@]2(C#Cc1cccc(C)c1)OC(=O)C1CCCC1]

Synthesis in analogy to the General Method 1 starting from (3aS,4R,7aS)-4-hydroxy-4-m-tolylethynyl-octahydro-indole-1-carboxylic acid methyl ester and cyclopentanecarboxylic acid to yield (3aR,4S,7aR)-methyl 4-(cyclopentanecarbonyloxy)-4-(m-tolylethynyl)octahydro-1H-indole-1-carboxylate. MS [M+H]=296 (ester eliminated ion); RT=4.183 min; HPLC Method III

EXAMPLE 50

(3aR,4S,7aR)-methyl 4-(4-fluorobenzoyloxy)-4-(m-tolylethynyl)octahydro-1H-indole-1-carboxylate

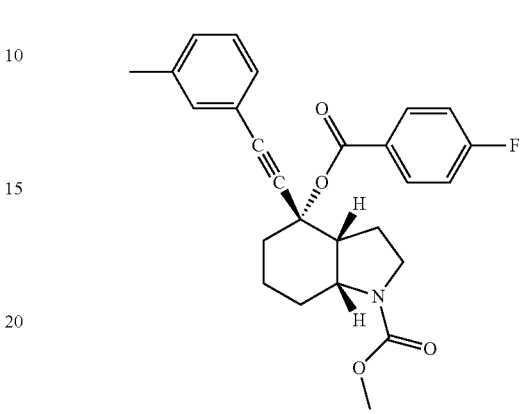

Synthesis in analogy to the General Method 1 starting from (3aS,4R,7aS)-4-hydroxy-4-m-tolylethynyl-octahydro-indole-1-carboxylic acid methyl ester and 4-fluoro-benzoic acid to yield (3aR,4S,7aR)-methyl 4-(4-fluorobenzoyloxy)-4-(m-tolylethynyl)octahydro-1H-indole-1-carboxylate. MS [M+H]=296 (ester eliminated ion); RT=4.093 min; HPLC Method III

EXAMPLE 51

(3aR,4S,7aR)-methyl 4-(nicotinoyloxy)-4-(m-tolylethynyl)octahydro-1H-indole-1-carboxylate

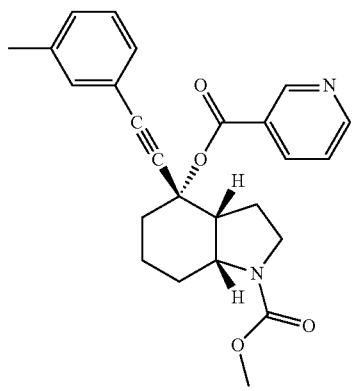 [SMILES: COC(=O)N1CC[C@@H]2[C@H]1CCC[C@]2(C#Cc1cccc(C)c1)OC(=O)c1cccnc1]

Synthesis in analogy to the General Method 1 starting from (3aS,4R,7aS)-4-hydroxy-4-m-tolylethynyl-octahydro-indole-1-carboxylic acid methyl ester and nicotinic acid to yield (3aR,4S,7aR)-methyl 4-(nicotinoyloxy)-4-(m-tolylethynyl)octahydro-1H-indole-1-carboxylate. MS [M+H]=419; RT=3.553 min; HPLC Method III

EXAMPLE 52

(3aR,4S,7aR)-methyl 4-(2-methylbenzoyloxy)-4-(m-tolylethynyl)octahydro-1H-indole-1-carboxylate

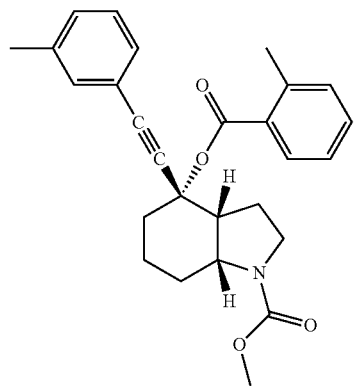 [SMILES: COC(=O)N1CC[C@@H]2[C@H]1CCC[C@]2(C#Cc1cccc(C)c1)OC(=O)c1ccccc1C]

Synthesis in analogy to the General Method 1 starting from (3aS,4R,7aS)-4-hydroxy-4-m-tolylethynyl-octahydro-indole-1-carboxylic acid methyl ester and 2-methyl-benzoic acid to yield (3aR,4S,7aR)-methyl 4-(2-methylbenzoyloxy)-4-(m-tolylethynyl)octahydro-1H-indole-1-carboxylate. MS [M+H]=296 (ester eliminated ion); RT=4.217 min; HPLC Method III

EXAMPLE 53

(3aR,4S,7aR)-methyl 4-(m-tolylethynyl)-4-(2,4,6-trimethylbenzoyloxy)octahydro-1H-indole-1-carboxylate

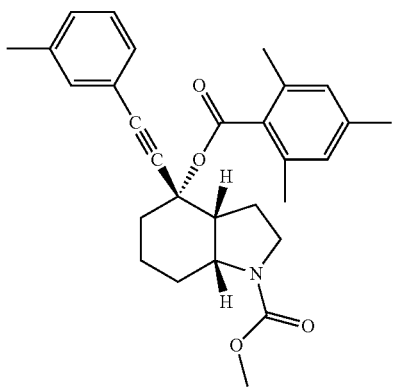

Synthesis in analogy to the General Method 1 starting from (3aS,4R,7aS)-4-hydroxy-4-m-tolylethynyl-octahydro-indole-1-carboxylic acid methyl ester and 2,4,6-trimethyl-benzoic acid to yield (3aR,4S,7aR)-methyl 4-(m-tolylethynyl)-4-(2,4,6-trimethylbenzoyloxy)octahydro-1H-indole-1-carboxylate. MS [M+H]=296 (ester eliminated ion); RT=4.280 min; HPLC Method III

EXAMPLE 54

(3aR,4S,7aR)-4-(Pyridine-2-carbonyloxy)-4-m-tolylethynyl-octahydro-indole-1-carboxylic acid methyl ester

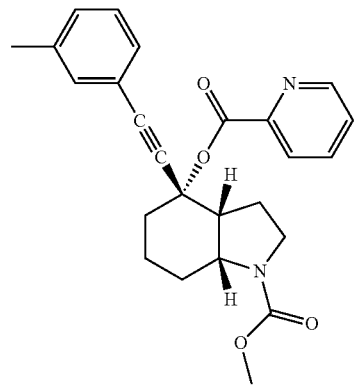 [SMILES: COC(=O)N1CC[C@@H]2[C@H]1CCC[C@]2(C#Cc1cccc(C)c1)OC(=O)c1ccccn1]

Synthesis in analogy to the General Method 1 starting from (3aS,4R,7aS)-4-hydroxy-4-m-tolylethynyl-octahydro-indole-1-carboxylic acid methyl ester and pyridine-2-carboxylic acid to yield (3aR,4S,7aR)-4-(pyridine-2-carbonyloxy)-4-m-tolylethynyl-octahydro-indole-1-carboxylic acid methyl ester. MS [M+H]=296 (ester eliminated ion); RT=3.433 min; HPLC Method III

EXAMPLE 55

(3aR,4S,7aR)-methyl 4-(5-amino-5-oxopentanoyloxy)-4-(m-tolylethynyl)octahydro-1H-indole-1-carboxylate

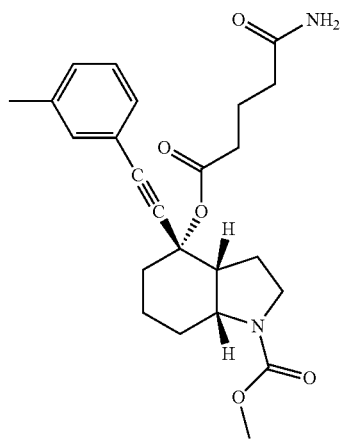 [SMILES: COC(=O)N1CC[C@@H]2[C@H]1CCC[C@]2(C#Cc1cccc(C)c1)OC(=O)CCCC(N)=O]

Synthesis in analogy to the General Method 1 starting from (3aS,4R,7aS)-4-hydroxy-4-m-tolylethyny-octahydro-indole-1-carboxylic acid methyl ester and 4-carbamoyl-butyric acid to yield (3aR,4S,7aR)-methyl 4-(5-amino-5-oxopentanoyloxy)-4-(m-tolylethynyl)octahydro-1H-indole-1-carboxylate. MS [M+H]=427; RT=1.01 min; UPLC Method I

EXAMPLE 56

(3aR,4S,7aR)-1-(methoxycarbonyl)-4-(m-tolylethynyl)octahydro-1H-indol-4-yl methyl glutarate

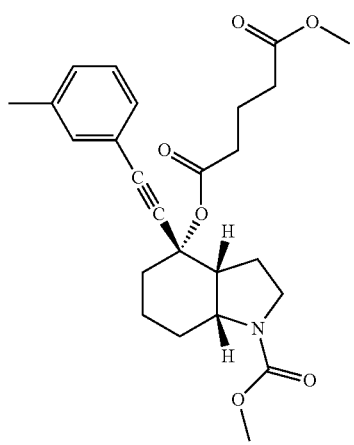

Synthesis in analogy to the General Method 1 starting from (3aS,4R,7aS)-4-hydroxy-4-m-tolylethynyl-octahydro-indole-1-carboxylic acid methyl ester and mono-methyl glutarate to yield (3aR,4S,7aR)-1-(methoxycarbonyl)-4-(m-tolylethynyl)octahydro-1H-indol-4-yl methyl glutarate. MS [M+H]=296 (ester elimination ion); RT=1.26 min; UPLC Method I

EXAMPLE 57

(3aR,4S,7aR)-methyl 4-(4-(diethylamino)-4-oxobutanoyloxy)-4-(m-tolylethynyl)octahydro-1H-indole-1-carboxylate

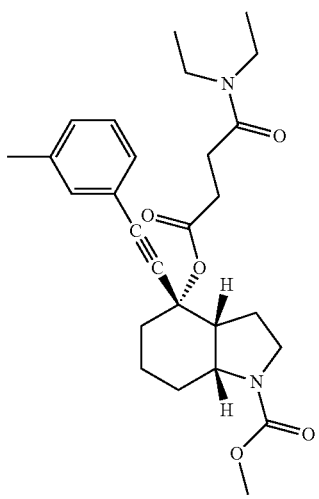 [SMILES: CCN(CC)C(=O)CCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and 4-(diethylamino)-4-oxobutanoic acid to yield (3aR,4S,7aR)-methyl 4-(4-(diethylamino)-4-oxobutanoyloxy)-4-(m-tolylethynyl)octahydro-1H-indole-1-carboxylate. MS [M+H]=296 (ester elimination ion); RT=1.22 min; UPLC Method I

EXAMPLE 58

(3aR,4S,7aR)-methyl 4-(4-(methylamino)-4-oxobutanoyloxy)-4-(m-tolylethynyl)octahydro-1H-indole-1-carboxylate

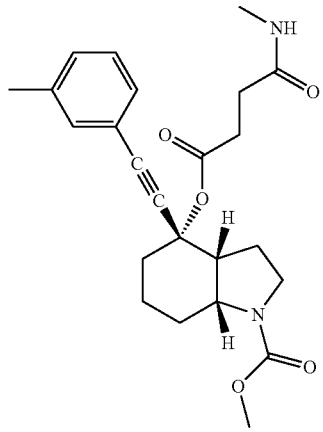 [SMILES: CNC(=O)CCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and N-methylsuccinamic acid to yield (3aR,4S,7aR)-methyl 4-(4-(methylamino)-4-oxobutanoyloxy)-4-(m-tolylethynyl)octahydro-1H-indole-1-carboxylate. MS [M+H]=427; RT=1.06 min; UPLC Method I

EXAMPLE 59

(3aR,4S,7aR)-methyl 4-(4-(dimethylamino)-4-oxobutanoyloxy)-4-(m-tolylethynyl)octa hydro-1H-indole-1-carboxylate

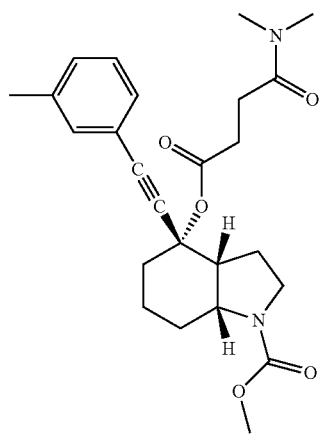

Synthesis in analogy to the General Method 1 starting from (3aS,4R,7aS)-4-hydroxy-4-m-tolylethynyl-octahydro-indole-1-carboxylic acid methyl ester and N,N-dimethylsuccinamic acid to yield (3aR,4S,7aR)-methyl 4-(4-(dimethylamino)-4-oxobutanoyloxy)-4-(m-tolylethynyl)octahydro-1H-indole-1-carboxylate. MS [2M+NH4]=898; RT=1.15 min; UPLC Method I

EXAMPLE 60

(3aR,4S,7aR)-methyl 4-(3-amino-3-oxopropanoyloxy)-4-(nm-tolylethynyl)octahydro-1H-indole-1-carboxylate

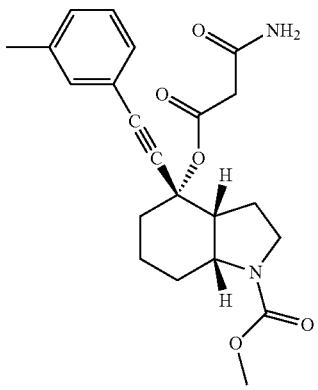 [SMILES: COC(=O)N1CC[C@@H]2[C@H]1CCC[C@]2(C#Cc1cccc(C)c1)OC(=O)CC(N)=O]

Synthesis in analogy to the General Method 1 starting from (3aS,4R,7aS)-4-hydroxy-4-m-tolylethynyl-octahydro-indole-1-carboxylic acid methyl ester and 3-amino-3-oxopropanoic acid to yield (3aR,4S,7aR)-methyl 4-(3-amino-3-oxopropanoyloxy)-4-(m-tolylethynyl)octahydro-1H-indole-1-carboxylate. MS [M+H]=296 (ester elimination ion); RT=0.96 min; UPLC Method I

EXAMPLE 61

(3aR,4S,7aR)-methyl 4-(3-(methylamino)-3-oxopropanoyloxy)-4-(m-tolylethynyl)octahydro-1H-indole-1-carboxylate

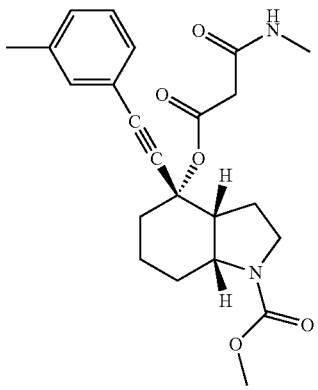

Synthesis in analogy to the General Method 1 starting from (3aS,4R,7aS)-4-hydroxy-4-m-tolylethynyl-octahydro-indole-1-carboxylic acid methyl ester and 3-(methylamino)-3-oxopropanoic acid to yield (3aR,4S,7aR)-methyl 4-(3-(methylamino)-3-oxopropanoyloxy)-4-(m-tolylethynyl) octahydro-1H-indole-1-carboxylate. MS [M+H]=296 (ester elimination ion); RT=1.01 min; UPLC Method I

EXAMPLE 62

((3aR,4S,7aR)-1-(methoxycarbonyl)-4-(m-tolylethynyl)octahydro-1H-indol-4-yl methyl succinate

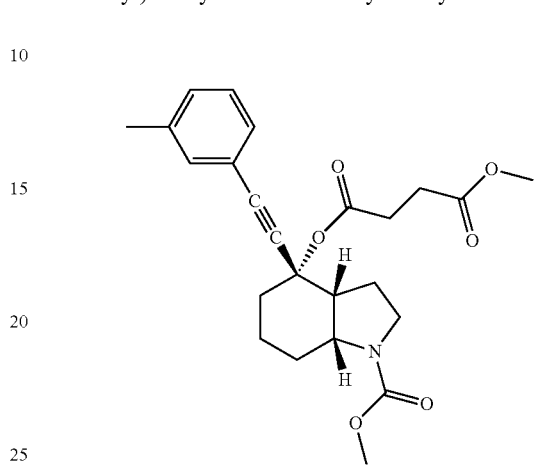

Synthesis in analogy to the General Method 1 starting from (3aS,4R,7aS)-4-hydroxy-4-m-tolylethynyl-octahydro-indole-1-carboxylic acid methyl ester and mono-methyl succinate to yield (3aR,4S,7aR)-1-(methoxycarbonyl)-4-(m-tolylethynyl)octahydro-1H-indol-4-yl methyl succinate. MS [M+H]=296 (ester elimination ion); RT=6.178 min; L-MS Method II

EXAMPLE 63

(3aR,4S,7aR)-methyl 4-(4-(dipropylamino)-4-oxobutanoyloxy)-4-(m-tolylethynyl)octahydro-1H-indole-1-carboxylate

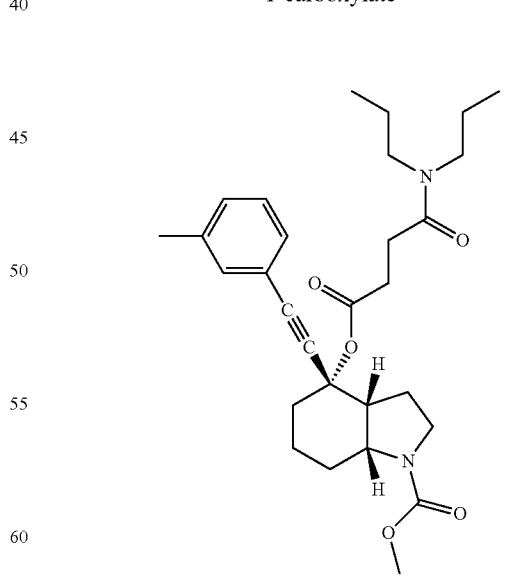

Synthesis in analogy to the General Method 1 starting from (3aS,4R,7aS)-4-hydroxy-4-m-tolylethynyl-octahydro-indole-1-carboxylic acid methyl ester and 4-(dipropylamino)-4-oxobutanoic acid to yield (3aR,4S,7aR)-methyl 4-(4-(dipropylamino)-4-oxobutanoyloxy)-4-(m-tolylethynyl)

octahydro-1H-indole-1-carboxylate. MS [M+H]=296 (ester elimination ion); RT=7.771 min; LC/MS LC-MS Method III

EXAMPLE 64

(3aR,4S,7aR)-methyl 4-(4-oxo-4-(propylamino)butanoyloxy)-4-(m-tolylethynyl)octahydro-1H-indole-1-carboxylate

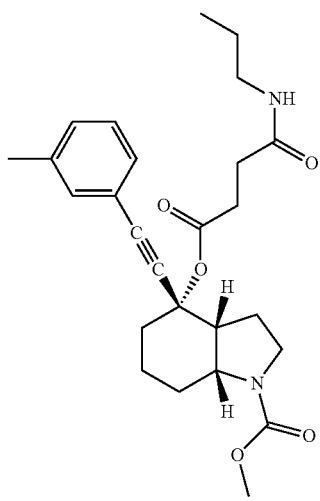 [SMILES: CCCNC(=O)CCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and N-propyl-succinamic acid to yield (3aR,4S,7aR)-methyl 4-(4-oxo-4-(propylamino)butanoyloxy)-4-(m-tolylethynyl)octahydro-1H-indole-1-carboxylate. MS [M+H]=455; RT=1.18 min; UPLC Method I

EXAMPLE 65

(3aR,4S,7aR)-methyl 4-(4-(pyrrolidin-1-yl)butanoyloxy)-4-(m-tolylethynyl)octahydro-1H-indole-1-carboxylate

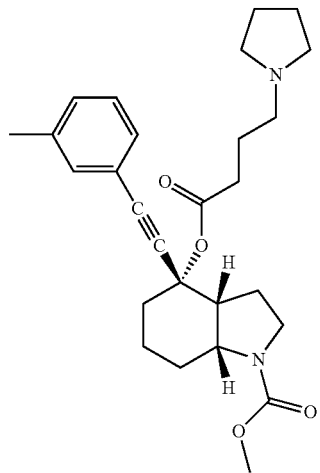 [SMILES: COC(=O)N1CC[C@@H]2[C@H]1CCC[C@]2(C#Cc1cccc(C)c1)OC(=O)CCCN1CCCC1]

Synthesis in analogy to the General Method 1 starting from (3aS,4R,7aS)-4-hydroxy-4-m-tolylethynyl-octahydro-indole-1-carboxylic acid methyl ester and 4-pyrrolidin-1-yl-butyric acid to yield (3aR,4S,7aR)-methyl 4-(4-(pyrrolidin-1-yl)butanoyloxy)-4-(m-tolylethynyl)octahydro-1H-indole-1-carboxylate. MS [M+H]=453; RT=0.96 min; UPLC Method I

EXAMPLE 66

(3aR,4S,7aR)-1-(methoxycarbonyl)-4-(m-tolylethynyl)octahydro-1H-indol-4-yl methyl malonate

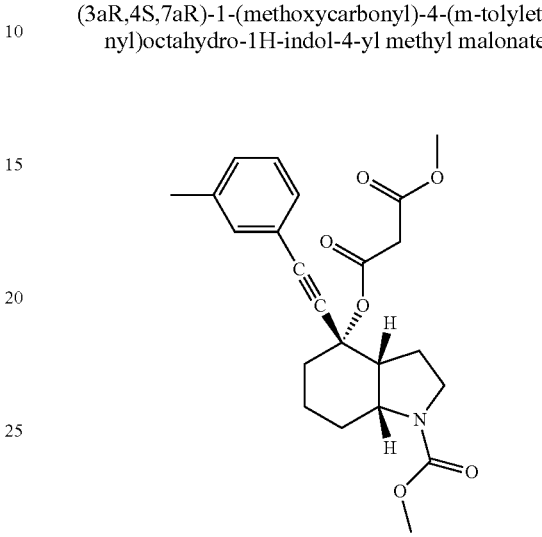

Synthesis in analogy to the General Method 1 starting from (3aS,4R,7aS)-4-hydroxy-4-m-tolylethyny-octahydro-indole-1-carboxylic acid methyl ester and malonic acid monomethyl ester to yield (3aR,4S,7aR)-1-(methoxycarbonyl)-4-(m-tolylethynyl)octahydro-1H-indol-4-yl methyl malonate. MS [M+H]=414; RT=1.24 min; UPLC Method I

EXAMPLE 67

(3aR,4S,7aR)-methyl 4-(4-(ethylamino)-4-oxobutanoyloxy)-4-(m-tolylethynyl)octahydro-1H-indole-1-carboxylate

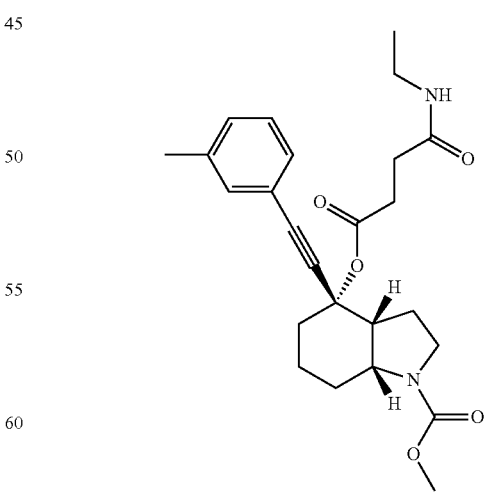

Synthesis in analogy to the General Method 1 starting from (3aS,4R,7aS)-4-hydroxy-4-m-tolylethynyl-octahydro-indole-1-carboxylic acid methyl ester and N-ethyl-succinamic acid to yield (3aR,4S,7aR)-methyl 4-(4-(ethylamino)-4-oxobutanoyloxy)-4-(m-tolylethynyl)octahydro-1H-indole-1-carboxylate. MS [M+H]=441; RT=1.13 min; UPLC Method I

EXAMPLE 68

(3aR,4S,7aR)-methyl 4-(5-(ethylamino)-5-oxopentanoyloxy)-4-(m-tolylethynyl)octahydro-1H-indole-1-carboxylate

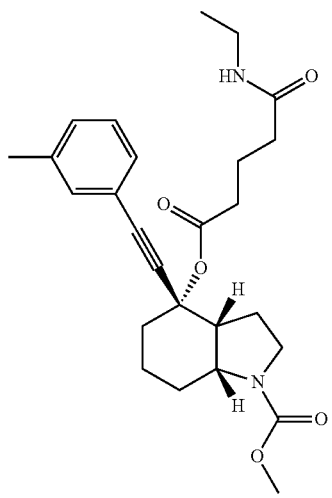 [SMILES: CCNC(=O)CCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and 4-ethylcarbamoyl-butyric acid to yield (3aR,4S,7aR)-methyl 4-(5-(ethylamino)-5-oxopentanoyloxy)-4-(m-tolylethynyl)octahydro-1H-indole-1-carboxylate. MS [2M+H]=910; RT=1.13 min; UPLC Method I

EXAMPLE 69

(3aR,4S,7aR)-methyl 4-(5-(isopropylamino)-5-oxopentanoyloxy)-4-(m-tolylethynyl)octahydro-1H-indole-1-carboxylate

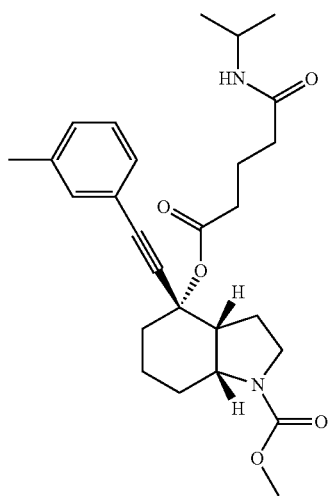 [SMILES: COC(=O)N1CC[C@@H]2[C@H]1CCC[C@]2(C#Cc1cccc(C)c1)OC(=O)CCCC(=O)NC(C)C]

Synthesis in analogy to the General Method 1 starting from (3aS,4R,7aS)-4-hydroxy-4-m-tolylethynyl-octahydro-indole-1-carboxylic acid methyl ester and 4-isopropylcarbamoyl-butyric acid to yield (3aR,4S,7aR)-methyl 4-(5-(isopropylamino)-5-oxopentanoyloxy)-4-(m-tolylethynyl)octahydro-1H-indole-1-carboxylate. MS [2M+H]=938; RT=1.18 min; UPLC Method I

EXAMPLE 70

(3aR,4S,7aS)-methyl 4-(5-oxo-5-(propylamino)pentanoyloxy)-4-(m-tolylethynyl)octahydro-1H-indole-1-carboxylate

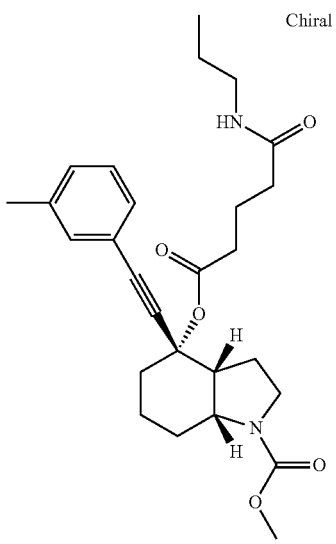 [SMILES: CCCNC(=O)CCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and 4-propylcarbamoyl-butyric acid to yield (3aR,4S,7aR)-methyl 4-(5-oxo-5-(propylamino)pentanoyloxy)-4-(m-tolylethynyl)octahydro-1H-indole-1-carboxylate. MS [2M+H]=938; RT=1.19 min; UPLC Method I

EXAMPLE 71

(3aR,4S,7aR)-methyl 4-(5-(dimethylamino)-5-oxopentanoyloxy)-4-(m-tolylethynyl)octahydro-1H-indole-1-carboxylate

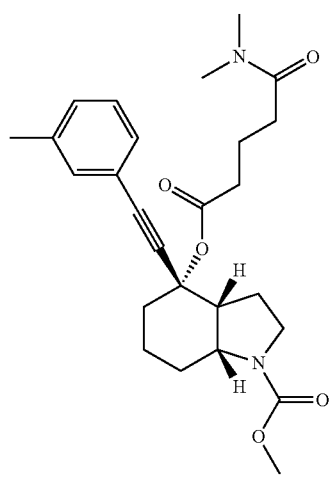 [SMILES: COC(=O)N1CC[C@@H]2[C@H]1CCC[C@]2(C#Cc1cccc(C)c1)OC(=O)CCCC(=O)N(C)C]

Synthesis in analogy to the General Method 1 starting from (3aS,4R,7aS)-4-hydroxy-4-m-tolylethynyl-octahydro-indole-1-carboxylic acid methyl ester and 4-dimethylcarbamoyl-butyric acid to yield (3aR,4S,7aR)-methyl 4-(5-(dimethylamino)-5-oxopentanoyloxy)-4-(m-tolylethynyl) octahydro-1H-indole-1-carboxylate. MS [2M+NH4]=927; RT=1.16 min; UPLC Method I

EXAMPLE 72

(3aR,4S,7aR)-methyl 4-(5-(diethylamino)-5-oxopentanoyloxy)-4-(m-tolylethynyl)octahydro-1H-indole-1-carboxylate

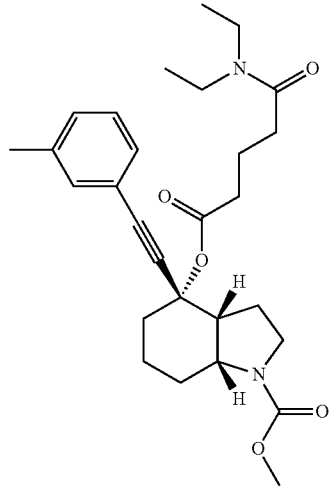 [SMILES: CCN(CC)C(=O)CCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and 4-diethylcarbamoyl-butyric acid to yield (3aR,4S,7aR)-methyl 4-(5-(diethylamino)-5-oxopentanoyloxy)-4-(m-tolylethynyl)octahydro-1H-indole-1-carboxylate. MS [2M+NH4]=982; RT=1.23 min; UPLC Method I

EXAMPLE 73

(3aR,4S,7aR)-methyl 4-(5-(dipropylamino)-5-oxopentanoyloxy)-4-(m-tolylethynyl)octahydro-1H-indole-1-carboxylate

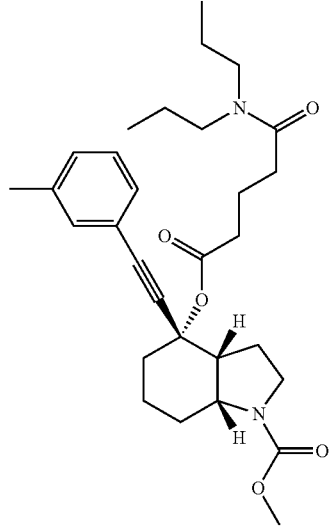 [SMILES: CCCN(CCC)C(=O)CCCC(=O)O[C@@]1(C#Cc2cccc(C)c2)CCC[C@@H]2[C@H]1CCN2C(=O)OC]

Synthesis in analogy to the General Method 1 starting from (3aS,4R,7aS)-4-hydroxy-4-m-tolylethynyl-octahydro-indole-1-carboxylic acid methyl ester and 4-dipropylcarbamoyl-butyric acid to yield (3aR,4S,7aR)-methyl 4-(5-(dipropylamino)-5-oxopentanoyloxy)-4-(m-tolylethynyl)octahydro-1H-indole-1-carboxylate. MS [2M+H+NH4]=1039; RT=1.41 min; UPLC Method I

EXAMPLE 74

(3aR,4S,7aR)-4-(3-Methoxy-benzoyloxy)-4-m-tolylethynyl-octahydro-indole-1-carboxylic acid methyl ester

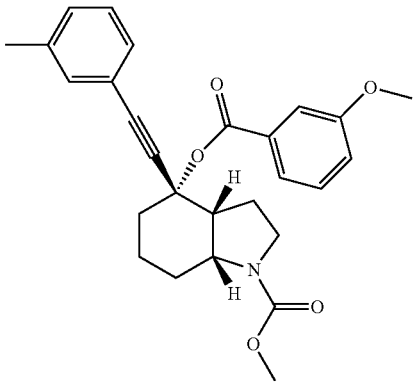

Synthesis in analogy to the General Method 1 starting from (3aS,4R,7aS)-4-hydroxy-4-m-tolylethynyl-octahydro-indole-1-carboxylic acid methyl ester and 3-methoxy-benzoic acid to yield (3aR,4S,7aR)-4-(3-methoxy-benzoyloxy)-4-m-tolyethynyl-octahydro-indole-1-carboxylic acid methyl ester. MS [M+H]=296 (ester elimination ion); RT=9.087 min; HPLC Method I

EXAMPLE 75

(3aR,4S,7aR)-4-m-Tolylethynyl-4-(2,3,4-trimethoxy-benzoyloxy)-octahydro-indole-1-carboxylic acid methyl ester

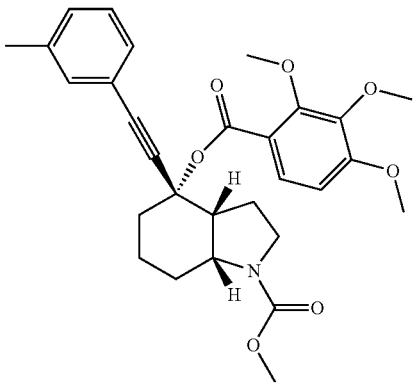

Synthesis in analogy to the General Method 1 starting from (3aS,4R,7aS)-4-hydroxy-4-m-tolylethynyl-octahydro-indole-1-carboxylic acid methyl ester and 2,3,4-trimethoxy-benzoic acid to yield (3aR,4S,7aR)-4-m-tolylethynyl-4-(2,3,4-trimethoxy-benzoyloxy)-octahydro-indole-1-carboxylic acid methyl ester. MS [M+H]=296 (ester elimination ion); RT=8.527 min; HPLC Method I

EXAMPLE 76

(3aR,4S,7aR)-4-[2-(3-Methoxy-phenyl)-acetoxy]-4-m-tolylethynyl-octahydro-indole-1-carboxylic acid methylester

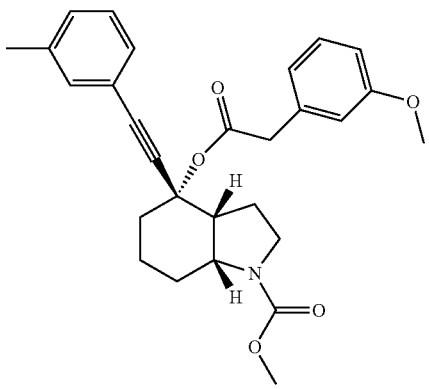

Synthesis in analogy to the General Method 1 starting from (3aS,4R,7aS)-4-hydroxy-4-m-tolylethynyl-octahydro-indole-1-carboxylic acid methyl ester and 3-methoxy-benzoic acid to yield (3aR,4S,7aR)-4-[2-(3-methoxy-phenyl)-acetoxy]-4-m-tolylethynyl-octahydro-indole-1-carboxylic acid methylester. MS [M+H]=296 (ester elimination ion); RT=8.743 min; HPLC Method I

EXAMPLE 77

(3aR,4S,7aR)-4-(3,5-Dimethyl-benzoyloxy)-4-m-tolylethynyl-octahydro-indole-1-carboxylic acid methyl ester

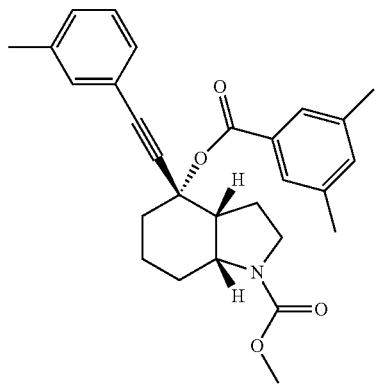

Synthesis in analogy to the General Method 1 starting from (3aS,4R,7aS)-4-hydroxy-4-m-tolylethynyl-octahydro-indole-1-carboxylic acid methyl ester and 3,5-dimethyl-benzoic acid to yield (3aR,4S,7aR)-4-(3,5-dimethyl-benzoyloxy)-4-m-tolylethynyl-octahydro-indole-1-carboxylic acid methyl ester. MS [M+H]=296 (ester elimination ion); RT=8.590 min; LC/MS Method III

EXAMPLE 78

(3aR,4S,7aR)-4-m-Tolylethynyl-4-(3-trifluoromethyl-benzoyloxy)-octahydro-indole-1-carboxylic acid methyl ester

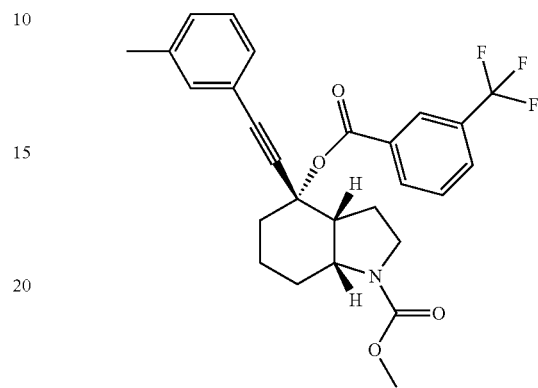

Synthesis in analogy to the General Method 1 starting from (3aS,4R,7aS)-4-hydroxy-4-m-tolylethynyl-octahydro-indole-1-carboxylic acid methyl ester and 3-Trifluoromethyl-benzoic acid to yield (3aR,4S,7aR)-4-m-tolylethynyl-4-(3-trifluoromethyl-benzoyloxy)-octahydro-indole-1-carboxylic acid methyl ester. MS [M+H]=296 (ester elimination ion); RT=8.705 min; LC-MS Method III

EXAMPLE 79

(3aR,4S,7aR)-4-(2-Fluoro-benzoyloxy)-4-m-tolylethynyl-octahydro-indole-1-carboxylic acid methyl ester

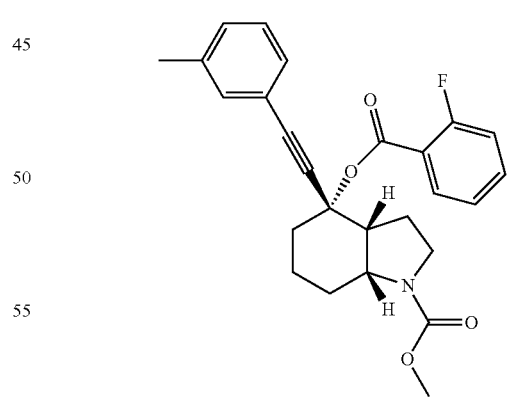

Synthesis in analogy to the General Method 1 starting from (3aS,4R,7aS)-4-hydroxy-4-m-tolylethynyl-octahydro-indole-1-carboxylic acid methyl ester and 2-fluoro-benzoic acid to yield (3aR,4S,7aR)-4-(2-fluoro-benzoyloxy)-4-m-tolylethynyl-octahydro-indole-1-carboxylic acid methyl ester. MS [M+H]=296 (ester elimination ion); RT=8.923 min; HPLC Method I

EXAMPLE 80

(3aR,4S,7aR)-4-(2,5-Dimethyl-benzoyloxy)-4-m-tolylethynyl-octahydro-indole-1-carboxylic acid methyl ester

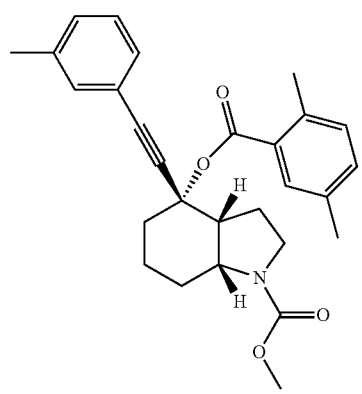 [SMILES: COC(=O)N1CC[C@@H]2[C@H]1CCC[C@]2(C#Cc1cccc(C)c1)OC(=O)c1cc(C)ccc1C]

Synthesis in analogy to the General Method 1 starting from (3aS,4R,7aS)-4-hydroxy-4-m-tolylethynyl-octahydro-indole-1-carboxylic acid methyl ester and 2,5-dimethyl-benzoic acid to yield (3aR,4S,7aR)-4-(2,5-dimethyl-benzoyloxy)-4-m-tolylethynyl-octahydro-indole-carboxylic acid methyl ester. MS [M+H]=296 (ester elimination ion); RT=9.860 min; HPLC Method I

EXAMPLE 81

(3aR,4S,7aR)-4-[2-(2,6-Dichloro-phenyl)-acetoxy]-4-m-tolylethynyl-octahydro-indole-1-carboxylic acid methyl ester

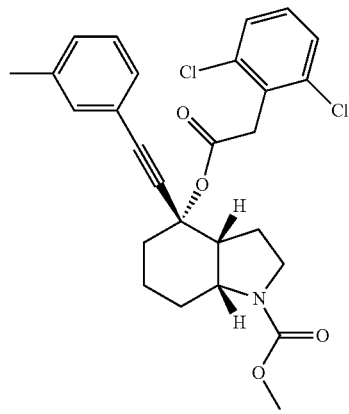 [SMILES: COC(=O)N1CC[C@@H]2[C@H]1CCC[C@]2(C#Cc1cccc(C)c1)OC(=O)Cc1c(Cl)cccc1Cl]

Synthesis in analogy to the General Method 1 starting from (3aS,4R,7aS)-4-hydroxy-4-m-tolylethynyl-octahydro-indole-1-carboxylic acid methyl ester and (2,6-dichloro-phenyl)-acetic acid to yield (3aR,4S,7aR)-4-[2-(2,6-dichloro-phenyl)-acetoxy]-4-m-tolylethynyl-octahydro-indole-1-carboxylic acid methyl ester. MS [M+H]=296 (ester elimination ion); RT=9.620 min; HPLC Method I

EXAMPLE 82

(3aR,4S,7aR)-4-(2-Acetylamino-pyridine-4-carbonyloxy)-4-m-tolylethyny-octahydro-indole-1-carboxylic acidmethyl ester

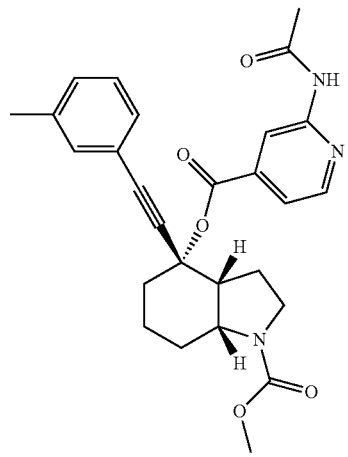 [SMILES: COC(=O)N1CC[C@@H]2[C@H]1CCC[C@]2(C#Cc1cccc(C)c1)OC(=O)c1ccnc(NC(C)=O)c1]

Synthesis in analogy to the General Method 1 starting from (3aS,4R,7aS)-4-hydroxy-4-m-tolylethynyl-octahydro-indole-1-carboxylic acid methyl ester and 2-acetylamino-isonicotinic acid to yield (3aR,4S,7aR)-4-(2-acetylamino-pyridine-4-carbonyloxy)-4-m-tolylethynyl-octahydro-indole-1-carboxylic acid methyl ester. MS [M+H] 476; RT=7.443 min HPLC Method I

EXAMPLE 83

(3aR,4S,7aR)-Methyl 4-(m-tolylethynyl)-4-(2-(3-(trifluoromethyl)phenyl)acetoxy)octahydro-1H-indole-1-carboxylate

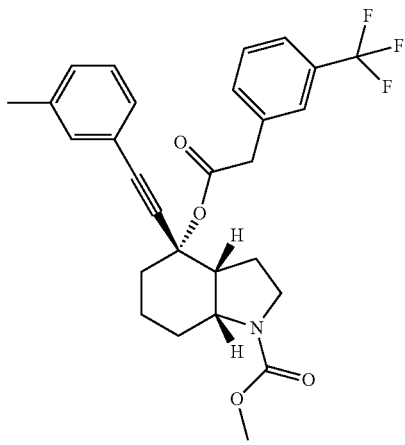 [SMILES: COC(=O)N1CC[C@@H]2[C@H]1CCC[C@]2(C#Cc1cccc(C)c1)OC(=O)Cc1cccc(C(F)(F)F)c1]

Synthesis in analogy to the General Method 1 starting from (3aS,4R,7aS)-4-hydroxy-4-m-tolylethynyl-octahydro-indole-1-carboxylic acid methyl ester and (3-trifluoromethyl-phenyl)-acetic acid to yield (3aR,4S,7aR)-methyl 4-(m-tolylethynyl)-4-(2-(3-(trifluoromethyl)phenyl)acetoxy) octahydro-1H-indole-1-carboxylate. MS [M+H]=296 (ester elimination ion); RT=8.365 min; LCMS Method III

EXAMPLE 84

(3aR,4S,7aR)-Methyl 4-(2-(4-methoxyphenyl)acetoxy)-4-(m-tolylethynyl)octahydro-1H-indole-1-carboxylate

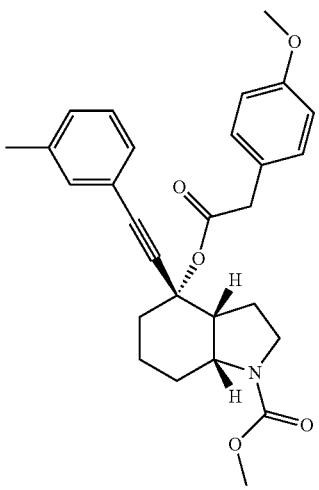 [SMILES: COC(=O)N1CC[C@@H]2[C@H]1CCC[C@]2(C#Cc1cccc(C)c1)OC(=O)Cc1ccc(OC)cc1]

Synthesis in analogy to the General Method 1 starting from (3aS,4R,7aS)-4-hydroxy-4-m-tolylethynyl-octahydro-indole-1-carboxylic acid methyl ester and (4-methoxy-phenyl)-acetic acid to yield (3aR,4S,7aR)-methyl 4-(2-(4-methoxyphenyl)acetoxy)-4-(m-tolylethynyl)octahydro-1H-indole-1-carboxylate. MS [M+H]=296 (ester elimination ion); RT==7.889 min; LCMS Method III

EXAMPLE 85

(3aR,4S,7aR)-Methyl 4-(2-(3,4-dimethoxyphenyl)acetoxy)-4-(m-tolylethynyl)octahydro-1H-indole-1-carboxylate

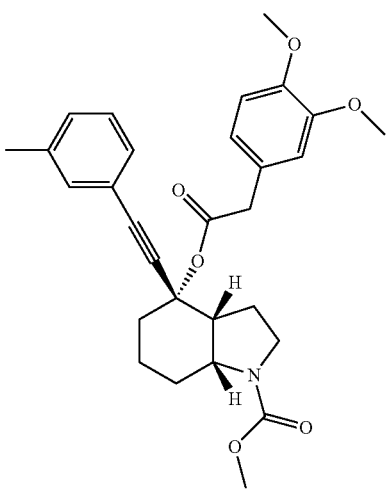

Synthesis in analogy to the General Method 1 starting from (3aS,4R,7aS)-4-hydroxy-4-m-tolylethynyl-octahydro-indole-1-carboxylic acid methyl ester and (3,4-dimethoxy-phenyl)-acetic acid to yield (3aR,4S,7aR)-methyl 4-(2-(3,4-dimethoxyphenyl)acetoxy)-4-(m-tolylethynyl)octahydro-1H-indole-1-carboxylate. MS [M+H] 296 (ester elimination ion); RT=7.486 min LCMS Method III

EXAMPLE 86

(3aR,4S,7aR)-4-((S)-Pyrrolidine-2-carbonyloxy)-4-m-tolylethynyl-octahydro-indole-1-carboxylic acid methyl ester

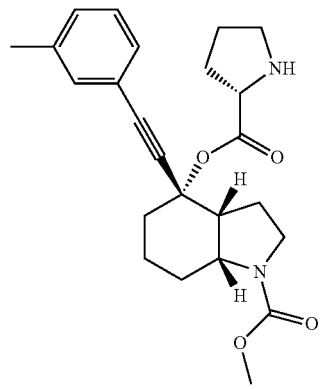 [SMILES: COC(=O)N1CC[C@@H]2[C@H]1CCC[C@]2(C#Cc1cccc(C)c1)OC(=O)[C@@H]1CCCN1]

Synthesis in analogy to the General Method 1 starting from (3aS,4R,7aS)-4-hydroxy-4-m-tolylethynyl-octahydro-indole-1-carboxylic acid methyl ester and Nboc-(S)-proline to yield (S)-pyrrolidine-1,2-dicarboxylic acid 1-tert-butyl ester 2-((3aR,4S,7aR)-1-methoxycarbonyl-4-m-tolylethynyl-octahydro-indol-4-yl) ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-4-((S)-pyrrolidine-2-carbonyloxy)-4-m-tolylethynyl-octahydro-indole-1-carboxylic acid methyl ester. MS [M+H] 411; RT=4.853 min LCMS Method III

EXAMPLE 87

(3aR,4S,7aR)-Methyl 4-(2-(piperazin-1-yl)acetoxy)-4-(m-tolylethynyl)octahydro-1H-indole-1-carboxylate

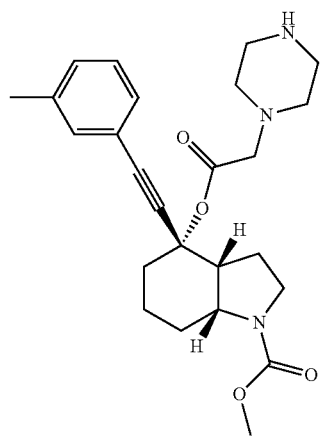 [SMILES: COC(=O)N1CC[C@@H]2[C@H]1CCC[C@]2(C#Cc1cccc(C)c1)OC(=O)CN1CCNCC1]

Synthesis in analogy to the General Method 1 starting from (3aS,4R,7aS)-4-hydroxy-4-m-tolylethynyl-octahydro-indole-1-carboxylic acid methyl ester and 4-carboxymethyl-piperazine-1-carboxylic acid tert-butyl ester to yield (3aR,4S,7aR)-4-[2-(4-tert-butoxycarbonyl-piperazin-1-yl)-acetoxy]-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-methyl 4-(2-(piperazin-1-yl)acetoxy)-4-(m-tolylethynyl)octahydro-1H-indole-1-carboxylate. MS [M+H] 440; RT=4.882 min; LCMS Method III

EXAMPLE 88

(3aR,4S,7aR)-Methyl 4-(2-(pyrrolidin-1-yl)acetoxy)-4-(m-tolylethynyl)octahydro-1H-indole-1-carboxylate

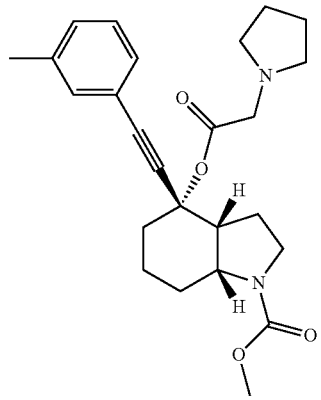 [SMILES: COC(=O)N1CC[C@@H]2[C@H]1CCC[C@]2(C#Cc1cccc(C)c1)OC(=O)CN1CCCC1]

Synthesis in analogy to the General Method 1 starting from (3aS,4R,7aS)-4-hydroxy-4-m-tolylethynyl-octahydro-indole-1-carboxylic acid methyl ester and pyrrolidin-1-yl-acetic acid to yield (3aR,4S,7aR)-methyl 4-(2-(pyrrolidin-1-yl)acetoxy)-4-(m-tolylethynyl)octahydro-1H-indole-1-carboxylate. MS [M+H] 425; RT=4.954 min; LCMS Method III

EXAMPLE 89

(3aR,4S,7aR)-Methyl 4-((S)-2,6-diaminohexanoyloxy)-4-(m-tolylethynyl)octahydro-1H-indole-1-carboxylate

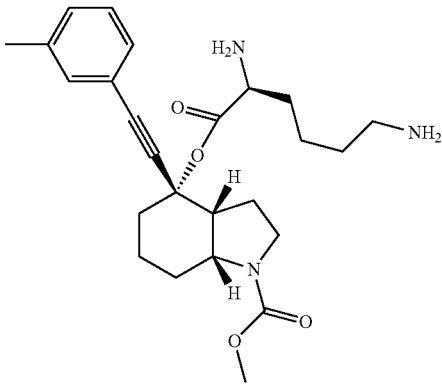 [SMILES: COC(=O)N1CC[C@@H]2[C@H]1CCC[C@]2(C#Cc1cccc(C)c1)OC(=O)[C@@H](N)CCCCN]

Synthesis in analogy to the General Method 1 starting from (3aS,4R,7aS)-4-hydroxy-4-m-tolylethynyl-octahydro-indole-1-carboxylic acid methyl ester and (S)-2,6-bis-tert-butoxycarbonylamino-hexanoic acid to yield (3aR,4S,7aR)-4-((S)-2,6-bis-tert-butoxycarbonylamino-hexanoyloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-methyl 4-((S)-2,6-diaminohexanoyloxy)-4-(m-tolylethynyl)octahydro-1H-indole-1-carboxylate. MS [M+H] 442; RT=3.992 min; LCMS Method III

EXAMPLE 90

(3aR,4S,7aR)-Methyl 4-((S)-2-amino-5-guanidinopentanoyloxy)-4-(m-tolylethynyl)octahydro-1H-indole-1-carboxylate

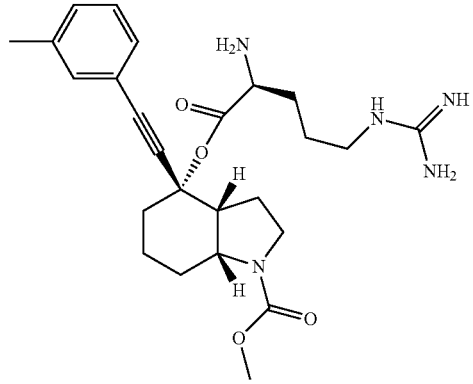 [SMILES: COC(=O)N1CC[C@@H]2[C@H]1CCC[C@]2(C#Cc1cccc(C)c1)OC(=O)[C@@H](N)CCCNC(=N)N]

Synthesis in analogy to the General Method 1 starting from (3aS,4R,7aS)-4-hydroxy-4-m-tolylethynyoctahydro-indole-1-carboxylic acid methyl ester and (S)-2,5-bis-tert-butoxycarbonylamino-5-guanidino-pentanoic acid to yield (3aR,4S,7aR)-4-((S)-2,5-bis-tert-butoxycarbonylamino-5-guanidinopentanoyloxy)-4-m-tolylethynyl-octahydro-indole-1-carboxylic acid methyl ester. This NBoc-protected product was then stirred in hydrochloric acid dioxane solution (4M, 10 equiv.) at room temperature for 6 hrs. Subsequently the solvent was removed the residue dissolved in dichloromethane and washed with saturated sodium hydrogencarbonate solution. The organic layer was tried with sodium sulfate, filtrated and evaporated. The crude product was subjected to silica gel flash chromatography (ISCO CombiFlash; dichloromethane/methanol; 100/0 to 95/5) to yield (3aR,4S,7aR)-methyl 4-((S)-2-amino-5-guanidinopentanoyloxy)-4-(m-tolylethynyl)octahydro-1H-indole-1-carboxylate. MS [M+H] 470; RT=3.963 min LCMS Method III

EXAMPLE 91

(3aR,4S,7aR)-4-Methoxy-4-m-tolylethynyl-octahydro-indole-1-carboxylic acid methyl ester

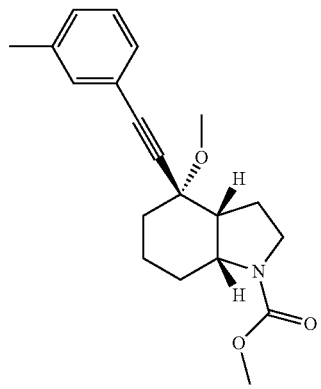 [SMILES: COC(=O)N1CC[C@@H]2[C@H]1CCC[C@]2(C#Cc1cccc(C)c1)OC]

(3aS,4R,7aS)-4-hydroxy-4-m-tolylethynyl-octahydro-indole-1-carboxylic acid methyl ester (100 mg, 0.32 mmol) was dissolved in DMF (3 mL). Then, molecular sieves (4 A), silver(I)oxide (355 mg, 1.53 mmol) and methyl iodide (0.40 ml, 6.38 mmol) was added and the black suspension stirred at room temperature for 48 hour. The reaction mixture was filtrated through celite and the filtrate evaporated. The crude yellow residue was subjected to silica gel flash chromatography (ISCO Companion CombiFlash; 40 g Gold silica gel cartridge, heptane/ethyl acetate gradient; ethyl acetate: 2% (2 min), 2-20% (3 min), 20% (8 min), 20-30% (2 min), 30% (8 min), 30-50% (3 min) and 50% (8 min) to yield (3aR,4S,7aR)-4-methoxy-4-m-tolylethynyl-octahydro-indole-1-carboxylic acid methyl ester (15 mg, 0.04 mmol, 14% yield) as colorless oil. MS [2M+Na]677; RT=8.147 min HPLC Method III

TABLE 1 mGluR5 antagonists (parent compounds)

The invention provides prodrugs of mGluR5 antagonists of formula (IIA) listed below in Table 1.

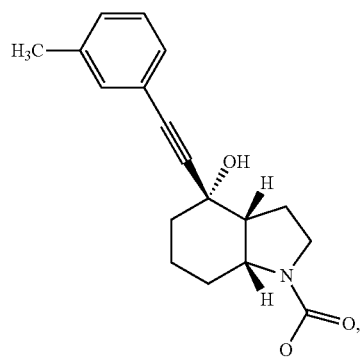
(IIA)

| Example No | R₁ |
|---|---|
| 1.0 | methyl |
| 2.0 | ethyl | wherein R₁ is as defined in Table 1.
The synthesis of Examples 1.0 and 2.0 is described in WO2003047581 and/or WO2010018154.

TABLE 2

In-vitro activity of mGluR5 antagonists (parent compounds)

| Example | IC50[nM] mGluR5 |
|---|---|
| 1.0 | 15 |
| 2.0 | 42 |

Parent compounds exhibit an antagonistic action at human metabotropic glutamate receptor 5 (human mGluR5). This can be determined in vitro, for example, at recombinant human mGluR5, using different procedures like, for example, measurement of the inhibition of the agonist induced elevation of intracellular $Ca^{2+}$ concentration in accordance with L. P. Daggett et al., Neuropharm. Vol. 34, pages 871-886 (1995), P. J. Flor et al., J. Neurochem. Vol. 67, pages 58-63 (1996) or by determination to what extent the agonist induced elevation of the inositol phosphate turnover is inhibited as described by T. Knoepfel et al., Eur. J. Pharmacol. Vol. 288, pages 389-392 (1994), L. P. Daggett et al., Neuropharm. Vol. 67, pages 58-63 (1996) and references cited therein. Isolation and expression of human mGluR subtypes are described in U.S. Pat. No. 5,521,297.

TABLE 3

PK/PD comparison of Prodrug versus Parent in an in-vivo exposure assay

| Example | Rat plasma exposure of parent compound [pmol/mL] | Rat brain exposure of parent compound [pmol/g] |
|---|---|---|
| Example 9 | 90 | 338 |
| Example 28 | 52 | 155 |
| Example 1.0 | 150 | 690 |

Examples 9 and 28 were administered to male Sprague-Dawley rats (n = 3 for each substance) orally at the dose of 3 mg-base/kg as a suspension in Carboxymethylcellulose 0.5% in water/Tween 80, 99.5/0.5, v/v. One hour after oral dosage, the animals were sacrificed and blood and the brain samples were collected and rapidly deep-frozen on dry-ice. The levels of the parent compound, Example 1.0, were determined by LC-MS-MS analysis. The data obtained after administration of the prodrugs of the invention were compared with those obtained after oral administration of the parent compound itself (same experimental design: example 1.0 suspended in Carboxymethylcellulose 0.5% in water/Tween 80, 99.5/0.5, v/v and orally dosed at 3 mg/kg to 3 male Sprague-Dawley rats. Blood and brain were collected at 1 h post-dose).

TABLE 4

In-vitro clearance (CL) of parent compounds compared to prodrugs in liver microsomes (determination of metabolic stability using rat liver microsomes)

| Example | CL (rat) [µL/min × mg] | CL (human) [µL/min × mg] | Example | CL (rat) [µL/min × mg] | CL (human) [µL/min × mg] |
|---|---|---|---|---|---|
| 1.0 | 277 | 113 | 30 | 375 | n.d. |
| 1 | 195 | 14 | 31 | 262 | n.d. |
| 3 | 730 | 283 | 32 | 420 | n.d. |
| 4 | 478 | 630 | 33 | 660 | n.d. |
| 5 | 48 | n.d. | 34 | 495 | n.d. |
| 6 | 51 | n.d. | 35 | 50 | n.d. |
| 7 | 346 | 433 | 36 | 815 | n.d. |
| 8 | 87 | 187 | 37 | 693 | n.d. |
| 9 | 355 | 315 | 40 | 302 | 36 |
| 14 | 3.4 | n.d. | 41 | 579 | 693 |
| 16 | 26 | 33 | 43 | 36 | n.d. |
| 19 | 32 | n.d | 45 | 385 | n.d. |
| 20 | 5.4 | n.d. | 46 | 4.4 | n.d. |
| 23 | 3.4 | n.d. | 48 | 26 | n.d. |
| 24 | 32 | n.d. | 51 | 478 | n.d. |
| 25 | 32 | n.d. | 53 | 3.4 | n.d. |
| 26 | 533 | 770 | 54 | 167 | n.d. |

TABLE 4-continued

In-vitro clearance (CL) of parent compounds compared to prodrugs in liver microsomes (determination of metabolic stability using rat liver microsomes)

| Example | CL (rat) [μL/min × mg] | CL (human) [μL/min × mg] | Example | CL (rat) [μL/min × mg] | CL (human) [μL/min × mg] |
|---|---|---|---|---|---|
| 27 | 533 | 94 | 63 | 26 | n.d. |
| 29 | 730 | 660 | | | |

Metabolic stability of new chemical entities (1 μM final concentration) was determined in rat and/or human liver microsomes (0.5 mg protein/mL) by an automated method in 96-well format using the compound depletion approach, quantified by LC-MS/MS. The liver microsome preparations was reconstituted for assessment of cytochrome P450-mediated metabolism by the addition of 1 mM NADPH cofactor. In vitro metabolic half-life (t½, min) and intrinsic clearance (CLint, μL/min/mg) are based on the rate and extent of metabolism of the test article (TA) as determined by the disappearance of the parent compound from the reaction mixture [Obach 1999]. These values may be scaled to predict hepatic metabolic clearance rate (CLh, mL/min/kg). More detailed, a typical experiment is performed in 96-well format with shaking incubation at 37° C. The in vitro metabolic clearance rate is derived from data collected at four time points (eg. 0, 5, 15 and 30 minutes) in a reaction including cofactor(s) (NADPH and/or UDPGA). A 30 minutes negative control incubation (minus cofactor) is also performed to assess CYP-unrelated stability issues (eg, chemical instability, CYP-independent metabolism). In general, TA's in 10 mM DMSO are diluted 1:1000 into 0.6% ACN (v/v) in DiH2O to 10 μM. Immediately prior to the start of the experiment, 1.25 mg/mL of microsomal protein is suspended in 50 mM KPi [Obach 1999, Kalvass 2001, Pearce 1996, Yan 2003]. TA (35 μL) is added to 140 μL of the microsomal suspensions for 175 μLenzyme-substrate mixture. This enzyme · substrate mixture is pre-incubated for 15 min at 37° C. The 30 min negative control incubation is processed by combining 25 μL of enzyme · substrate mixture with an equal volume of 50 mM KPi containing 4 mM MgCl2. Following a 30 minute incubation at 37° C., the mix is quenched by adding 50 μL of ACN containing the MS internal standard (2 μM alprenolol). The T = 0 min time point is processed by combining 25 μL of enzyme · substrate mixture directly with 50 μL of ACN containing the MS internal standard (2 μM alprenolol). 25 μL of the cofactor solution is added (2 mM NADPH in 50 mM KPi plus 4 mM MgCl2) to simulate the complete quenched reaction mixture. The bulk reactions for the remaining time points are initiated by addition of 125 μL of cofactor solution (2 mM NADPH in 50 mM KPi plus 4 mM MgCl2) to the remaining 125 μL. At specific reaction time points (eg. 5, 15, 30 minutes), reaction aliquots (50 μL) are removed and reactions are terminated by addition of acetonitrile (50 μL) containing mass spectrometry internal standard (2 μM alprenolol). All the samples are centrifuged at 5000 × g at 4° C. for 30 min and the supernatants are analyzed by LC-MS/MS for quantitation of remaining TA. The percentage of TA remaining, relative to 0 minutes, is used to estimate in vitro elimination-rate constant (kmic) which can be used to calculate in vitro metabolic clearance rates. [Kalvass J C , Tess D A , Giragossian C, Linhares M C , Maurer T S (2001)] Influence of microsomal concentration on apparent intrinsic clearance: implications for scaling in vitro data. Drug Metab Dispos; 29: 1332-1336. [Obach R S (1999)] Prediction of human clearance of twenty-nine drugs from hepatic microsomal intrinsic clearance data: An examination of in vitro half-life approach and nonspecific binding to microsomes. Drug Metab Dispos; 27: 1350-1359. [Pearce R E , McIntyre C J , Madan A, Sanzgiri U, Draper A J , Bullock P L , Cook D C , Burton L A , Latham J, Nevins C, Parkinson A (1996)] Effects of freezing, thawing, and storing human liver microsomes on cytochrome P450 activity. Arch Biochem Biophys; 331: 145-169. [Yan Z, Caldwell G W (2003)] Metabolic assessment in liver microsomes by co-activating cytochrome P450s and UDP-glycosyltransferases. Eur J Drug Metab Pharmacokinet; 28: 223-232.

TABLE 5

Physico-chemical properties of parent compounds compared to prodrugs-solubility

| Example | Solubility (g/l) | Example | Solubility (g/l) | Example | Solubility (g/l) |
|---|---|---|---|---|---|
| 1.0 | 0.051 | 25 | <0.002 | 60 | 0.110 |
| 8 | 0.125 | 26 | 0.138 | 61 | 0.011 |
| 10 | 0.047 | 27 | 0.108 | 62 | 0.164 |
| 13 | 0.012 | 29 | 0.439 | 63 | 0.043 |
| 14 | 0.009 | 38 | 0.027 | 64 | 0.033 |
| 15 | 0.002 | 41 | 0.003 | 66 | 0.100 |
| 16 | <0.002 | 45 | <0.002 | 67 | 0.123 |
| 17 | <0.002 | 51 | <0.002 | 68 | 0.386 |
| 18 | <0.002 | 54 | 0.002 | 69 | 0.028 |
| 19 | <0.002 | 55 | 0.093 | 70 | 0.032 |
| 20 | <0.002 | 56 | 0.097 | | |
| 22 | <0.002 | 57 | 0.019 | | |
| 23 | <0.002 | 58 | 0.087 | | |
| 24 | <0.002 | 59 | <0.002 | | |

Solubility was determined in the following buffer: Cl free phosphate buffer (0.067 M.) is made from KH2PO4 solution and titrated to pH 6.8 with NaOH. The table below represents solubility values of compounds in the above buffer.

The following are further embodiments of the invention:
Embodiment 1: A compound of the formula I

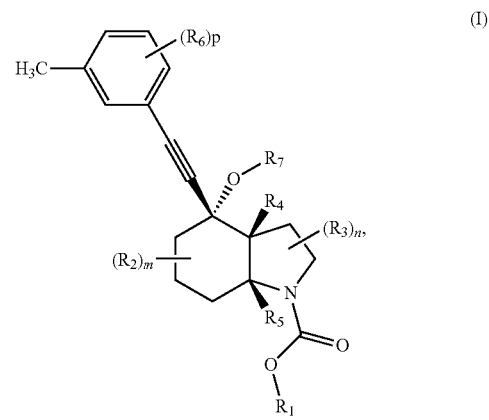

(I)

wherein
$R_1$ is $C_{1-4}$alkyl, $C_3$ cycloalkyl or $C_{3-6}$cycloalkyl-$C_{1-4}$alkyl;
$R_2$ and $R_3$ independently are halogen, cyano, hydroxy, amino, $C_{1-4}$alkyl; $C_{1-4}$halogenalkyl; $C_{1-4}$hydroxyalkyl; $C_{1-4}$aminoalkyl; $C_{1-4}$alkylamino-$C_{1-4}$alkyl; di-($C_{1-4}$alkyl)amino-$C_{1-4}$alkyl; $C_{1-4}$alkoxy-$C_{1-4}$alkyl; $C_{2-4}$alkenyl $C_{2-4}$halogenalkenyl; $C_{2-4}$alkinyl; $C_{2-4}$halogenalkinyl; $C_{1-4}$alkoxy; $C_{1-4}$halogenalkoxy; $C_{1-4}$alkyl-amino; di-($C_{1-4}$alkyl)amino or $C_{3-6}$cycloalkyl, wherein one carbon atom of the $C_{3-6}$cycloalkyl may be replaced by an oxygen atom and wherein the $C_{3-6}$cycloalkyl may be attached directly to the ring system or via a $C_{1-2}$alkylene or an oxygen;
m is 0, 1, 2, 3, 4, 5 or 6;
n is 0, 1, 2, 3 or 4;
$R_4$ and $R_5$ independently are hydrogen, halogen or methyl;
$R_6$ is halogen, hydroxy, amino, cyano, methyl or methoxy;
p is 0, 1, 2, 3 or 4;
$R_7$ is —C(O)$R_8$; —$R_9$; —P(O$R_{10}$)(O$R_{11}$), —Z, —C(O)—(CH$_2$)$_q$—O—Z, —(CH$_2$)$_r$—O—Z or —(CH$_2$)$_s$—O—(CH$_2$)$_t$—O—Z;
$R_8$ is $C_{1-20}$alkyl which may be substituted once or more than once by $R_{12}$; $C_{2-20}$alkenyl which may be substituted once or more than once by $R_{13}$; $C_{2-20}$alkinyl which may be substituted once or more than once by $R_{14}$; or a three- to seven-membered monocyclic ring system which may be aromatic, saturated or unsaturated non-aromatic, which may contain from 1 to 4 hetero atoms selected from nitrogen, oxygen and sulfur, and which may be substituted once or more than once by $R_{15}$;
$R_9$ is $C_{1-10}$alkyl which may be substituted once or more than once by $R_{16}$; $C_{2-10}$alkenyl which may be substituted once or more than once by $R_{17}$; $C_{2-10}$alkinyl which may be substituted once or more than once by $R_{18}$; or a three- to seven-membered monocyclic ring system which may be aromatic, saturated or unsaturated non-aromatic, which may contain from 1 to 4 hetero atoms selected from nitrogen, oxygen and sulfur, and which may be substituted once or more than once by $R_{19}$;
$R_{10}$ and $R_{11}$ independently are $C_{1-6}$alkyl;
each $R_{12}$, $R_{13}$, $R_{14}$, $R_{16}$, $R_{17}$ and $R_{18}$ independently is halogen, cyano, hydroxy, —SH, amino, $C_{1-6}$alkoxy, $C_{1-4}$alkoxy-$C_{1-4}$alkoxy, $C_{1-4}$alkoxy-$C_{1-4}$alkoxy-$C_{1-4}$alkoxy, $C_{1-6}$alkylthio, —C(O)OH, $C_{1-6}$alkylamino, di($C_{1-6}$alkyl)amino, aminocarbonyl, $C_{1-6}$alkylaminocarbonyl, di($C_{1-6}$alkyl)aminocarbonyl, $C_{1-6}$alkylcarbonylamino, ($C_{1-6}$alkyl)($C_{1-6}$alkylcarbonyl)amino, —N(H)—C(NH (NH$_2$), C$_{1-6}$alkylcarbonyloxy, C$_{1-6}$alkoxycarbonyl, or a three- to seven-membered monocyclic ring system which may be aromatic, saturated or unsaturated non-aromatic, which may contain from 1 to 4 hetero atoms selected from nitrogen, oxygen and sulfur, which may be attached directly or via bivalent oxygen or carbonyl, and which may in turn be substituted once or more than once by halogen, cyano, hydroxy, C$_{1-4}$alkyl, C$_{1-4}$alkoxy or C$_{1-4}$halogenalkyl;

each R$_{15}$ and R$_{19}$ independently is halogen, cyano, hydroxy, —SH, amino, C$_{1-6}$alkoxy, C$_{1-4}$alkoxy-C$_{1-4}$alkoxy, C$_{1-4}$alkoxy-C$_{14}$alkoxy-C$_{1-4}$alkoxy, C$_{1-6}$alkylthio, —C(O)OH, C$_{1-6}$alkylamino, di(C-alkyl)amino, C$_{1-6}$alkylaminocarbonyl, di(C$_{1-6}$alkyl)aminocarbonyl, C$_{1-6}$alkylcarbonylamino, (C$_{1-6}$alkyl)(C$_{1-6}$alkylcarbonyl)amino, C$_{1-6}$alkylcarbonyloxy, C$_{1-6}$alkoxycarbonyl; C$_{1-6}$alkyl, C$_{1-6}$halogenalkyl, C$_{1-6}$cyanoalkyl, C$_{1-6}$hydroxyalkyl, C$_{1-4}$alkoxy-C$_{1-4}$ q is an integer from 1 to 10;
r is an integer from 1 to 10;
s is an integer from 1 to 6;
t is an integer from 1 to 6;
Z is a saccharide moiety selected from the group consisting of a monosaccharide moiety and an oligosaccharide moiety, wherein Z is attached through a hydroxyl oxygen atom of Z; in free form or in salt form.

Embodiment 2: A compound of the formula I according to embodiment 1 wherein R$_7$ is —C(O)R$_5$.

Embodiment 3: A compound of formula I according to embodiment 1, wherein R$_7$ is —C(O)R$_8$; and R$_8$ is a natural amino acid, wherein said natural amino acid is attached through a —C(O)OH carbonyl of said natural amino acid.

Embodiment 4: A compound of formula I according to embodiment 1, wherein R$_7$ is —Z.

Embodiment 5:
A compound of formula I according to embodiment 1, wherein R$_7$ is —Z; and Z is a monosaccharide moiety, wherein Z is attached through a hydroxyl oxygen atom of Z.

Embodiment 6: A compound of formula I according to embodiment 1, wherein R$_1$ is methyl or ethyl; m, n and p are all 0; and R$_4$ and R$_5$ are both hydrogen.

Embodiment 7: Further examples of suitable compounds of the invention are compounds selected from the following group P:

Group P: Suitable Compounds of the Invention:

(3aR,4S,7aR)-4-(2-Dimethylamino-acetoxy)-4-m-tolylethynyl-octahydro-indole-1-carboxylic acid methyl ester;
(3aR,4S,7aR)-4-(3-Dimethylamino-propionyloxy)-4-m-tolylethynyl-octahydro-indole-1-carboxylic acid methyl ester;
(3aR,4S,7aR)-4-(4-Dimethylamino-butyryloxy)-4-m-tolylethynyl-octahydro-indole-1-carboxylic acid methyl ester;
(3aR,4S,7aR)-4-((S,R)-2-Amino-3-methyl-butyryloxy)-4-m-tolylethynyl-octahydro-indole-1-carboxylic acid methyl ester;
(3aR,4S,7aR)-4-((S)-2-Amino-4-methyl-pentanoyloxy)-4-m-tolylethynyl-octahydro-indole-1-carboxylic acid methyl ester;
(3aR,4S,7aR)-4-((S)-2-Amino-4-methylsulfanyl-butyryloxy)-4-m-tolylethynyl-octahydro-indole-1-carboxylic acid methyl ester;
(3aR,4S,7aR)-4-(2-Methylamino-acetoxy)-4-m-tolylethyny-octahydro-indole-1-carboxylic acid methyl ester;
(3aR,4S,7aR)-4-(2-Amino-acetoxy)-4-m-tolylethynyl-octahydro-indole-1-carboxylic acid methyl ester;
(3aR,4S,7aR)-4-((S)-2-Amino-propionyloxy)-4-m-tolylethynyl-octahydro-indole-1-carboxylic acid methyl ester;
(3aR,4S,7aR)-4-(2-Methoxy-acetoxy)-4-m-tolylethynyl-octahydro-indole-1-carboxylic acid methyl ester;
(3aR,4S,7aR)-4-[2-(2-Methoxy-ethoxy)-acetoxy]-4-m-tolylethynyl-octahydro-indole-1-carboxylic acid methyl ester;
(3aR,4S,7aR)-4-{2-[2-(2-Methoxy-ethoxy)-ethoxy]-acetoxy}-4-m-tolylethynyl-octahydro-indole-1-carboxylic acid methyl ester;
(3aR,4S,7aR)-4-Acetoxy-4-m-tolylethynyl-octahydro-indole-1-carboxylic acid methyl ester;
(3aR,4S,7aR)-4-Propionyloxy-4-m-tolylethynyl-octahydro-indole-1-carboxylic acid methyl ester;
(3aR,4S,7aR)-4-Butyryloxy-4-m-tolylethynyl-octahydro-indole-1-carboxylic acid methyl ester;
(3aR,4S,7aR)-4-Tetradecanoyloxy-4-m-tolylethynyl-octahydro-indole-1-carboxylic acid methyl ester;
(3aR,4S,7aR)-4-Hexanoyloxy-4-m-tolylethynyl-octahydro-indole-1-carboxylic acid methyl ester;
(3aR,4S,7aR)-4-Octanoyloxy-4-m-tolylethynyl-octahydro-indole-1-carboxylic acid methyl ester;
(3aR,4S,7aR)-4-Dodecanoyloxy-4-m-tolylethynyl-octahydro-indole-1-carboxylic acid methyl ester;
(3aR,4S,7aR)-4-Decanoyloxy-4-m-tolylethynyl-octahydro-indole-1-carboxylic acid methyl ester;
(3aR,4S,7aR)-4-(Dimethoxy-phosphanyloxy)-4-m-tolyethynyl-octahydro-indole-1-carboxylic acid methyl ester;
(3aR,4S,7aR)-4-Pentanoyloxy-4-m-tolylethynyl-octahydro-indole-1-carboxylic acid methyl ester;
(3aR,4S,7aR)-4-Heptanoyloxy-4-m-tolylethynyl-octahydro-indole-1-carboxylic acid methyl ester;
(3aR,4S,7aR)-4-Nonanoyloxy-4-m-tolylethynyl-octahydro-indole-1-carboxylic acid methyl ester;
(3aR,4S,7aR)-4-m-Tolylethynyl-4-tridecanoyloxy-octahydro-indole-1-carboxylic acid methyl ester;
(3aR,4S,7aR)-4-(2-Morpholin-4-yl-acetoxy)-4-m-tolylethynyl-octahydro-indole-1-carboxylic acid methyl ester;
(3aR,4S,7aR)-4-(3-Morpholin-4-yl-propionyloxy)-4-m-tolylethynyl-octahydro-indole-1-carboxylic acid methyl ester;
(3aR,4S,7aR)-4-(2-Imidazol-1-yl-acetoxy)-4-m-tolylethynyl-octahydro-indole-1-carboxylic acid methyl ester;
(3aR,4S,7aR)-4-(3-Pyrrolidin-1-yl-propionyloxy)-4-m-tolylethynyl-octahydro-indole-1-carboxylic acid methyl ester;
(3aR,4S,7aR)-4-((S)-2-Amino-butyryloxy)-4-m-tolylethynyl-octahydro-indole-1-carboxylic acid methyl ester;
(3aR,4S,7aR)-4-((S)-2-Amino-3-phenyl-propionyloxy)-4-m-tolylethynyl-octahydro-indole-1-carboxylic acid methyl ester;
(3aR,4S,7aR)-4-((S)-2-Amino-pentanoyloxy)-4-m-tolylethynyl-octahydro-indole-1-carboxylic acid methyl ester;
(3aR,4S,7aR)-4-((2S,3S)-2-Amino-3-methyl-pentanoyloxy)-4-m-tolylethynyl-octahydro-indole-1-carboxylic acid methyl ester;
(3aR,4S,7aR)-4-((S)-2-Amino-4,4-dimethyl-pentanoyloxy)-4-m-tolylethynyl-octahydro-indole-1-carboxylic acid methyl ester;
(3aR,4S,7aR)-4-((S)-2-Methylamino-propionyloxy)-4-m-tolylethynyl-octahydro-indole-1-carboxylic acid methyl ester;
(3aR,4S,7aR)-4-((S)-3-Methyl-2-methylamino-butyryloxy)-4-m-tolylethyny-octahydro-indole-1-carboxylic acid methyl ester;
(3aR,4S,7aR)-4-((2S,3S)-3-Methyl-2-methylamino-pentanoyloxy)-4-m-tolylethynyl-octahydro-indole-1-carboxylic acid methyl ester;

(3aR,4S,7aR)-4-(4-Oxo-4-pyrrolidin-1-yl-butyryloxy)-4-m-tolylethyny-octahydro-indole-1-carboxylic acid methyl ester;

(3aR,4S,7aR)-4-m-Tolylethynyl-4-undecanoyloxy-octahydro-indole-1-carboxylic acid methyl ester;

(3aR,4S,7aR)-methyl 4-(3-aminopropanoyloxy)-4-(m-tolylethynyl)octahydro-1H-indole-1-carboxylate;

(3aR,4S,7aR)-methyl 4-((S)-2-amino-2-phenylacetoxy)-4-(m-tolylethynyl)octahydro-1H-indole-1-carboxylate;

(3aR,4S,7aR)-methyl 4-(benzoyloxy)-4-(m-tolylethynyl)octahydro-1H-indole-1-carboxylate;

(3aR,4S,7aR)-methyl 4-(2-phenylacetoxy)-4-(m-tolylethynyl)octahydro-1H-indole-1-carboxylate;

(3aR,4S,7aR)-methyl 4-(3-phenylpropanoyloxy)-4-(m-tolylethynyl)octahydro-1H-indole-1-carboxylate;

(3aR,4S,7aR)-methyl 4-(isonicotinoyloxy)-4-(m-tolylethynyl)octahydro-1H-indole-1-carboxylate;

(3aR,4S,7aR)-methyl 4-(3-methylbenzoyloxy)-4-(m-tolylethynyl)octahydro-1H-indole-1-carboxylate;

(3aR,4S,7aR)-methyl 4-(3,5-dichlorobenzoyloxy)-4-(m-tolylethynyl)octahydro-1H-indole-1-carboxylate;

(3aR,4S,7aR)-methyl 4-(4-bromobenzoyloxy)-4-(m-tolylethynyl)octahydro-1H-indole-1-carboxylate;

(3aR,4S,7aR)-methyl 4-(cyclopentanecarbonyloxy)-4-(m-tolylethynyl)octahydro-1H-indole-1-carboxylate;

(3aR,4S,7aR)-methyl 4-(4-fluorobenzoyloxy)-4-(m-tolylethynyl)octahydro-1H-indole-1-carboxylate;

(3aR,4S,7aR)-methyl 4-(nicotinoyloxy)-4-(m-tolylethynyl)octahydro-1H-indole-1-carboxylate;

(3aR,4S,7aR)-methyl 4-(2-methylbenzoyloxy)-4-(m-tolylethynyl)octahydro-1H-indole-1-carboxylate;

(3aR,4S,7aR)-methyl 4-(m-tolylethynyl)-4-(2,4,6-trimethylbenzoyloxy)octahydro-1H-indole-1-carboxylate;

(3aR,4S,7aR)-4-(Pyridine-2-carbonyloxy)-4-m-tolylethynyl-octahydro-indole-1-carboxylic acid methyl ester;

(3aR,4S,7aR)-methyl 4-(5-amino-5-oxopentanoyloxy)-4-(m-tolylethynyl)octahydro-1H-indole-1-carboxylate;

(3aR,4S,7aR)-1-(methoxycarbonyl)-4-(m-tolylethynyl)octahydro-1H-inol-4-yl methyate glutarate;

(3aR,4S,7aR)-methyl 4-(4-(diethylamino)-4-oxobutanoyloxy)-4-(m-tolylethynyl)octahydro-1H-indole-1-carboxylate;

(3aR,4S,7aR)-methyl 4-(4-(methylamino)-4-oxobutanoyloxy)-4-(m-tolylethynyl)octahydro-1H-indole-1-carboxylate;

(3aR,4S,7aR)-methyl 4-(4-(dimethylamino)-4-oxobutanoyloxy)-4-(m-tolylethynyl)octahydro-1H-indole-1-carboxylate;

(3aR,4S,7aR)-methyl 4-(3-amino-3-oxopropanoyloxy)-4-(m-tolylethynyl)octahydro-1H-indole-1-carboxylate;

(3aR,4S,7aR)-methyl 4-(3-(methylamino)-3-oxopropanoyloxy)-4-(m-tolylethynyl)octahydro-1H-indole-1-carboxylate;

((3aR,4S,7aR)-1-(methoxycarbonyl)-4-(m-tolylethynyl)octahydro-1H-indol-4-yl methyl succinate;

(3aR,4S,7aR)-methyl 4-(4-(dipropylamino)-4-oxobutanoyloxy)-4-(m-tolylethynyl)octahydro-1H-indole-1-carboxylate;

(3aR,4S,7aR)-methyl 4-(4-oxo-4-(propylamino)butanoyloxy)-4-(m-tolylethynyl)octahydro-1H-indole-1-carboxylate;

(3aR,4S,7aR)-methyl 4-(4-(pyrrolidin-1-yl)butanoyloxy)-4-(m-tolylethynyl)octahydro-1H-indole-1-carboxylate;

(3aR,4S,7aR)-1-(methoxycarbonyl)-4-(m-tolylethynyl)octahydro-1H-indol-4-yl methyl malonate;

(3aR,4S,7aR)-methyl 4-(4-(ethylamino)-4-oxobutanoyloxy)-4-(m-tolylethynyl)octahydro-1H-indole-1-carboxylate;

(3aR,4S,7aR)-methyl 4-(5-(ethylamino)-5-oxopentanoyloxy)-4-(m-tolylethynyl)octahydro-1H-indole-1-carboxylate;

(3aR,4S,7aR)-methyl 4-(5-(isopropylamino)-5-oxopentanoyloxy)-4-(m-tolylethynyl)octahydro-1H-indole-1-carboxylate;

(3aR,4S,7aR)-methyl 4-(5-oxo-5-(propylamino)pentanoyloxy)-4-(m-tolylethynyl)octahydro-1H-indole-1-carboxylate;

(3aR,4S,7aR) methyl 4-(5-(dimethylamino)-5-oxopentanoyloxy)-4-(m-tolylethynyl)octahydro-1H-indole-1-carboxylate;

(3aR,4S,7aR)-methyl 4-(5-(diethylamino)-5-oxopentanoyloxy)-4-(m-tolylethynyl)octahydro-1H-indole-1-carboxylate;

(3a 4S,7aR)-methyl 4-(5-(dipropylamino)-5-oxopentanoyloxy)-4-(m-tolylethynyl)octahydro-1H-indole-1-carboxylate;

(3aR,4S,7aR)-4-(3-Methoxy-benzoyloxy)-4-m-tolylethynyl-octahydro-indole-1-carboxylic acid methyl ester;

(3aR,4S,7aR)-4-m-Tolylethynyl-4-(2,3,4-trimethoxy-benzoyloxy)-octahydro-indole-1-carboxylic acid methyl ester;

(3aR,4S,7aR)-4-[2-(3-Methoxy-phenyl)-acetoxy]-4-m-tolylethynyl-octahydro-indole-1-carboxylic acid methyl ester;

(3aR,4S,7aR)-4-(3,5-Dimethyl-benzoyloxy)-4-m-tolylethynyl-octahydro-indole-1-carboxylic acid methyl ester;

(3aR,4S,7aR)-4-m-Tolyethynyl-4-(3-trifluoromethyl-benzoyloxy)-octahydro-indole-1-carboxylic acid methyl ester;

(3aR,4S,7aR)-4-(2-Fluoro-benzoyloxy)-4-m-tolylethynyl-octahydro-indole-1-carboxylic acid methyl ester;

(3aR,4S,7aR)-4-(2,5-Dimethyl-benzoyloxy)-4-m-tolylethynyl-octahydro-indole-1-carboxylic acid methyl ester;

(3aR,4S,7aR)-4-[2-(2,6-Dichloro-phenyl)-acetoxy]-4-m-tolylethynyl-octahydro-indole-1-carboxylic acid methyl ester;

(3aR,4S,7aR)-4-(2-Acetylamino-pyridine-4-carbonyloxy)-4-m-tolylethynyl-octahydro-indole-1-carboxylic acidmethyl ester;

(3aR,4S,7aR)-Methyl 4-(m-tolylethyl)-4-(2-(3-(trifluoromethyl)phenyl)acetoxy)octahydro-1H-indole-1-carboxylate;

(3aR,4S,7aR)-Methyl 4-(2-(4-methoxyphenyl)acetoxy)-4-(m-tolyethynyl)octahydro-1H-indole-1-carboxylate;

(3aR,4S,7aR)-Methyl 4-(2-(3,4-dimethoxyphenyl)acetoxy)-4-(m-tolylethynyl)octahydro-1H-indole-1-carboxylate;

(3aR,4S,7aR)-4-((S)-Pyrrolidine-2-carbonyloxy-4-m-tolyethynyl-octahydro-indole-1-carboxylic acid methyl ester;

(3aR,4S,7aR)-Methyl 4-(2-(piperazin-1-yl)acetoxy)-4-(m-tolylethynyl)octahydro-1H-indole-1-carboxylate;

(3aR,4S,7aR)-Methyl 4-(2-(pyrrolidin-1-yl)acetoxy)-4-(m-tolylethynyl)octahydro-1H-indole-1-carboxylate;

(3aR,4S,7aR)-Methyl 4-((S)-2,6-diaminohexanoyloxy)-4-(m-tolylethyny)octahydro-1H-indole-1-carboxylate;

(3aR,4S,7aR)-Methyl 4-((S)-2-amino-5-guanidinopentanoyloxy)-4-(m-tolylethynyl)octahydro-1H-indole-1-carboxylate;

(3aR,4S,7aR)-4-Methoxy-4-m-tolylethynyl-octahydro-indole-1-carboxylic acid methyl ester;

(3aR,4S,7aR)-4-m-Tolylethynyl-4-((2R,3R,4S,5S,6R)-3,4,5-trihydroxy-6-hydroxymethyl-tetrahydro-pyran-2-yloxy)-octahydro-indole-1-carboxylic acid methyl ester;

(3aR,4S,7aR)-4-m-Tolylethynyl-4-[2-((2S,3R,4S,5S,6R)-3,4,5-trihydroxy-6-hydroxymethyl-tetrahydro-pyran-2-yloxy)-acetoxy]-octahydro-indole-1-carboxylic acid methyl ester; or (3aR,4S,7aR)-4-m-Tolylethynyl-4-[2-((2S,3R,4S,5S,6R)-3,4,5-trihydroxy-6-hydroxymethyl-tetrahydro-pyran-2-yloxy)-ethoxy]-octahydro-indole-1-carboxylic acid methyl; in free form or in salt form.

Embodiment 8: A process for the production of a compound of the formula Ia

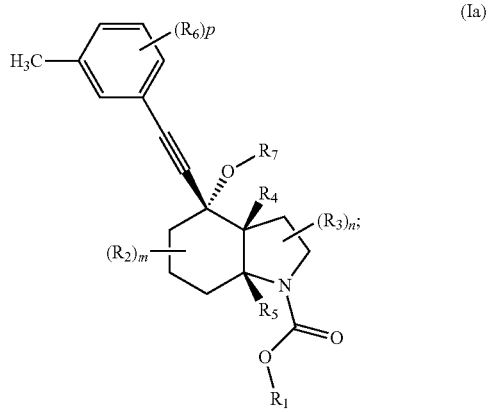

in which $R_1$, $R_2$, $R_3$, $R_4$, $R_5$, $R_6$, m, n and p are as defined under formula I in embodiment 1, and $R_7$ is —C(O)$R_8$, in which $R_8$ is as defined under formula I in embodiment 1, or a salt thereof, which comprises reacting a compound of formula IIa

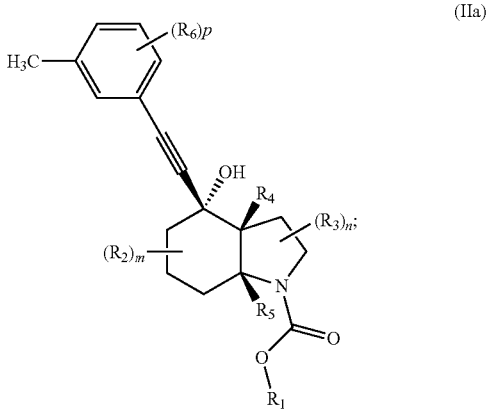

in which $R_1$, $R_2$, $R_3$, $R_4$, $R_5$, $R_6$, m, n and p are as defined under formula I in embodiment 1, or a salt thereof,
with a compound of formula IIIa

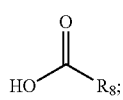

in which $R_8$ is as defined under formula I in embodiment 1, or a salt thereof, in the presence of dicyclohexylcarbodiimide or 1-ethyl-3-(3-dimethylaminopropyl)carbodiimide, a dialkyl-amino-pyridine, and a suitable solvent, to form the compound of formula Ia;

and optionally converting the compound of formula Ia to a salt thereof.

Embodiment 9: A pharmaceutical composition comprising a therapeutically effective amount of a compound according to any one of embodiments 1 to 7 and one or more pharmaceutically acceptable carriers.

Embodiment 10: A combination comprising a therapeutically effective amount of the compound according to any one of embodiments 1 to 7 and one or more therapeutically active agents.

Embodiment 11: A method of inhibiting mGluR5 activity in a subject, wherein the method comprises administering to the subject a therapeutically effective amount of the compound according to any one of embodiments 1 to 7.

Embodiment 12: A method of treating a disorder or a disease in a subject mediated by mGluR5, wherein the method comprises administering to the subject a therapeutically effective amount of the compound according to any one of embodiments 1 to 7.

Embodiment 13: A compound according to any one of embodiments 1 to 7, for use as a medicament.

Embodiment 14: Use of a compound according to any one of embodiments 1 to 7, for the treatment of a disorder or disease in a subject mediated by mGluR5.

Embodiment 15: Use of a compound according to any one of embodiments 1 to 7, for the treatment of a disorder or disease in a subject characterized by an abnormal activity of mGluR5.

Embodiment 16: A method of inhibiting mGluR5 activity in a subject, wherein the method comprises administering to the subject a therapeutically effective amount of a compound according to any one of embodiments 1 to 7.

Embodiment 17: A method of treating a disorder or a disease in a subject mediated by mGluR5, wherein the method comprises administering to the subject a therapeutically effective amount of a compound according to any one of embodiments 1 to 7. Preferably said disorder or said disease is selected from FXS, PD-LID and GERD.

Embodiment 18: Use of a compound according to any one of embodiments 1 to 7 for the manufacture of a medicament for the treatment of a disorder or disease in a subject mediated by mGluR5.

Embodiment 19: Use of a compound according to any one of embodiments 1 to 7 for the treatment of a disorder or disease in a subject mediated by mGluR5.

Embodiment 20: Use of a compound according to any one of embodiments 1 to 7 for the treatment of a disorder or disease in a subject characterized by an abnormal activity of mGluR5. Preferably said disorder or said disease is selected from FXS, PD-LID and GERD.

Embodiment 21: A compound of the formula I according to embodiment 1 wherein $R_7$ is —C(O)$R_8$; $R_8$ is a natural amino acid, wherein said natural amino acid is attached through a —C(O)OH carbonyl of said natural amino acid; $R_1$ is methyl or ethyl; m, n and p are all 0; and $R_4$ and $R_5$ are both hydrogen.

Embodiment 22: A compound of formula I according to embodiment 1, wherein $R_7$ is —Z; Z is a monosaccharide moiety, wherein Z is attached through a hydroxyl oxygen atom of Z; $R_1$ is methyl or ethyl; m, n and p are all 0; and $R_4$ and $R_5$ are both hydrogen.

The invention claimed is:
1. A compound of formula I

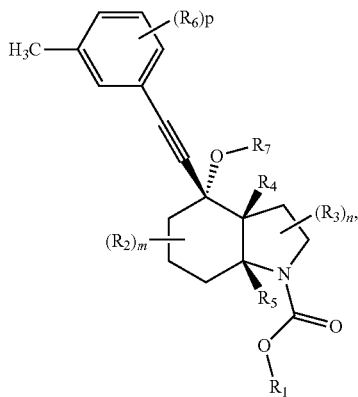

wherein
R$_1$ is C$_{1-4}$alkyl, C$_{3-6}$cycloalkyl or C$_{3-6}$cycloalkyl-C$_{1-4}$alkyl;
R$_2$ and R$_3$ independently are halogen, cyano, hydroxy, amino, C$_{1-4}$alkyl; C$_{1-4}$halogenalkyl; C$_{1-4}$hydroxyalkyl; C$_{1-4}$aminoalkyl; C$_{1-4}$alkylamino-C$_{1-4}$alkyl; di-(C$_{1-4}$alkyl)amino-C$_{1-4}$alkyl; C$_{1-4}$alkoxy-C$_{1-4}$alkyl; C$_{2-4}$alkenyl; C$_{2-4}$halogenalkenyl; C$_{2-4}$alkinyl; C$_{2-4}$halogenalkinyl; C$_{1-4}$alkoxy; C$_{1-4}$halogenalkoxy; C$_{1-4}$alkyl-amino; di-(C$_{1-4}$alkyl)amino or C$_{3-6}$cycloalkyl, wherein one carbon atom of the C$_{3-6}$cycloalkyl may be replaced by an oxygen atom and wherein the C$_{3-6}$cycloalkyl may be attached directly to the ring system or via a C$_{1-2}$alkylene or an oxygen;
m is 0, 1, 2, 3, 4, 5 or 6;
n is 0, 1, 2, 3 or 4;
R$_4$ and R$_5$ independently are hydrogen, halogen or methyl;
R$_6$ is halogen, hydroxy, amino, cyano, methyl or methoxy;
p is 0, 1, 2, 3 or 4;
R$_7$ is —C(O)R$_8$; and
R$_8$ is C$_{1-6}$alkyl which is substituted once or more than once by R$_{12}$; and wherein each R$_{12}$ is amino, morpholino, pyrrolidino, C$_{1-6}$alkylamino or aminocarbonyl;
in free form or in salt form.
2. A compound of formula I according to claim 1, wherein R$_1$ is methyl or ethyl; m, n and p are all 0; and R$_4$ and R$_5$ are both hydrogen.
3. A compound of formula I according to claim 1, wherein said compound is selected from the group consisting of
(3aR,4S,7aR)-4-(3-Dimethylamino-propionyloxy)-4-m-tolylethynyl-octahydro-indole-1-carboxylic acid methyl ester;
(3aR,4S,7aR)-4-(4-Dimethylamino-butyryloxy)-4-m-tolylethynyl-octahydro-indole-1-carboxylic acid methyl ester;
(3aR,4S,7aR)-4-((S,R)-2-Amino-3-methyl-butyryloxy)-4-m-tolylethynyl-octahydro-indole-1-carboxylic acid methyl ester;
(3aR,4S,7aR)-4-(2-Amino-acetoxy)-4-m-tolylethynyl-octahydro-indole-1-carboxylic acid methyl ester;
(3aR,4S,7aR)-4-((S)-2-Amino-propionyloxy)-4-m-tolyl-ethynyl-octahydro-indole-1-carboxylic acid methyl ester;
(3aR,4S,7aR)-4-(2-Morpholin-4-yl-acetoxy)-4-m-tolyl-ethynyl-octahydro-indole-1-carboxylic acid methyl ester;
(3aR,4S,7aR)-4-(3-Morpholin-4-yl-propionyloxy)-4-m-tolylethynyl-octahydro-indole-1-carboxylic acid methyl ester;
(3aR,4S,7aR)-4-(3-Pyrrolidin-1-yl-propionyloxy)-4-m-tolylethynyl-octahydro-indole-1-carboxylic acid methyl ester;
(3aR,4S,7aR)-4-((S)-2-Amino-butyryloxy)-4-m-tolyl-ethynyl-octahydro-indole-1-carboxylic acid methyl ester;
(3aR,4S,7aR)-4-((S)-2-Amino-pentanoyloxy)-4-m-tolyl-ethynyl-octahydro-indole-1-carboxylic acid methyl ester;
(3aR,4S,7aR)-4-((2S,3S)-2-Amino-3-methyl-pentanoyloxy)-4-m-tolylethynyl-octahydro-indole-1-carboxylic acid methyl ester;
(3aR,4S,7aR)-4-((S)-2-Amino-4,4-dimethyl-pentanoyloxy)-4-m-tolylethynyl-octahydro-indole-1-carboxylic acid methyl ester;
(3aR,4S,7aR)-4-((S)-3-Methyl-2-methylamino-butyryloxy)-4-m-tolylethynyl-octahydro-indole-1-carboxylic acid methyl ester;
(3aR,4S,7aR)-methyl 4-(3-aminopropanoyloxy)-4-(m-tolylethynyl)octahydro-1H-indole-1-carboxylate;
(3aR,4S,7aR)-methyl 4-(5-amino-5-oxopentanoyloxy)-4-(m-tolylethynyl)octahydro-1H-indole-1-carboxylate;
(3aR,4S,7aR)-1-(methoxycarbonyl)-4-(m-tolylethynyl) octahydro-1H-indol-4-yl methyl glutarate;
(3aR,4S,7aR)-methyl 4-(4-(methylamino)-4-oxobutanoyloxy)-4-(m-tolylethynyl)octahydro-1H-indole-1-carboxylate;
(3aR,4S,7aR)-methyl 4-(3-amino-3-oxopropanoyloxy)-4-(m-tolylethynyl)octahydro-1H-indole-1-carboxylate;
((3aR,4S,7aR)-1-(methoxycarbonyl)-4-(m-tolylethynyl) octahydro-1H-indol-4-yl methyl succinate;
(3aR,4S,7aR)-methyl 4-(4-(pyrrolidin-1-yl)butanoyloxy)-4-(m-tolylethynyl)octahydro-1H-indole-1-carboxylate;
(3aR,4S,7aR)-1-(methoxycarbonyl)-4-(m-tolylethynyl) octahydro-1H-indol-4-yl malonate;
(3aR,4S,7aR)-methyl 4-(4-(ethylamino)-4-oxobutanoyloxy)-4-(m-tolylethynyl)octahydro-1H-indole-1-carboxylate;
(3aR,4S,7aR)-methyl 4-(5-(ethylamino)-5-oxopentanoyloxy)-4-(m-tolylethynyl)octahydro-1H-indole-1-carboxylate;
(3aR,4S,7aR)-Methyl 4-(2-pyrrolidin-1-yl)acetoxy)-4-(m-tolylethynyl)octahydro-1H-indole-1-carboxylate;
(3aR,4S,7aR)-Methyl 4-((S)-2,6-diaminohexanoyloxy)-4-(m-tolylethynyl)octahydro-1H-indole-1-carboxylate;
in free form or in salt form.
4. A pharmaceutical composition comprising a therapeutically effective amount of a compound according to claim 1 and one or more pharmaceutically acceptable carriers.
5. A method of inhibiting mGluR5 activity in a subject, wherein the method comprises administering to the subject a therapeutically effective amount of the compound according to claim 1.
6. A compound selected from the group consisting of:
(3aR,4S,7aR)-1-(methoxycarbonyl)-4-(m-tolylethynyl) octahydro-1H-indol-4-yl methyl glutarate;
(3aR,4S,7aR)-methyl 4-(4-(methylamino)-4-oxobutanoyloxy)-4-(m-tolylethynyl)octahydro-1H-indole-1-carboxylate;
((3aR,4S,7aR)-1-(methoxycarbonyl)-4-(m-tolylethynyl) octahydro-1H-indol-4-yl methyl succinate;
(3aR,4S,7aR)-1-(methoxycarbonyl)-4-(m-tolylethynyl) octahydro-1H-indol-4-yl methyl malonate;

(3aR,4S,7aR)-methyl 4-(4-(ethylamino)-4-oxobutanoyloxy)-4-(m-tolylethynyl)octahydro-1H-indole-1-carboxylate and (3aR,4S,7aR)-methyl 4-(5-(ethylamino)-5-oxopentanoyloxy)-4-(m-tolylethynyl)octahydro-1H-indole-1-carboxylate; or a pharmaceutically acceptable salt thereof.

* * * * *